US011097122B2

(12) United States Patent
Lu

(10) Patent No.: US 11,097,122 B2
(45) Date of Patent: Aug. 24, 2021

(54) MAGNETIC STIMULATION OF THE SPINAL CORD TO RESTORE CONTROL OF BLADDER AND/OR BOWEL

(71) Applicant: The Regents of the University of California, Oakland, CA (US)

(72) Inventor: Daniel C. Lu, Los Angeles, CA (US)

(73) Assignee: The Regents of the University of California, Oakland, CA (US)

(*) Notice: Subject to any disclaimer, the term of this patent is extended or adjusted under 35 U.S.C. 154(b) by 381 days.

(21) Appl. No.: 15/344,381

(22) Filed: Nov. 4, 2016

(65) Prior Publication Data

US 2017/0165497 A1 Jun. 15, 2017

Related U.S. Application Data

(60) Provisional application No. 62/250,841, filed on Nov. 4, 2015.

(51) Int. Cl.
*A61N 2/00* (2006.01)
*A61N 1/04* (2006.01)
*A61N 1/36* (2006.01)
*A61N 2/02* (2006.01)

(52) U.S. Cl.
CPC ........... *A61N 2/006* (2013.01); *A61N 1/0456* (2013.01); *A61N 1/36017* (2013.01); *A61N 1/36034* (2017.08); *A61N 2/004* (2013.01); *A61N 2/02* (2013.01)

(58) Field of Classification Search
CPC ........ A61N 2/006; A61N 2/02; A61N 1/0456; A61N 1/36014; A61N 1/36017; A61N 2/004

USPC .................................................... 600/9–15
See application file for complete search history.

(56) References Cited

U.S. PATENT DOCUMENTS

| 3,543,761 A | 12/1970 | Bradley |
| 3,662,758 A | 5/1972 | Glover |
| 3,724,467 A | 4/1973 | Avery et al. |
| 4,044,774 A | 8/1977 | Corbin et al. |
| 4,102,344 A | 7/1978 | Conway et al. |
| 4,141,365 A | 2/1979 | Fischell et al. |

(Continued)

FOREIGN PATENT DOCUMENTS

| AU | 2012204526 A1 | 7/2013 |
| CA | 2 823 592 A1 | 7/2012 |

(Continued)

OTHER PUBLICATIONS

Andersson, KE. & Pehrson, R. ,CNS Involvement in Overactive Bladder. Drugs, Dec. 2003, vol. 63, Issue 23, pp. 2595-2611 (Year: 2003).*

(Continued)

*Primary Examiner* — Navin Natnithithadha
*Assistant Examiner* — Sunita Reddy
(74) *Attorney, Agent, or Firm* — Tom Hunter; Weaver Austin Villeneuve & Sampson LLP

(57) ABSTRACT

In various embodiments methods and devices are provided for facilitating locomotor function and/or voiding of bladder and/or bowel in a subject with a neuromotor disorder. In certain embodiments the methods involve providing magnetic stimulation of the spinal cord at a location, frequency and intensity sufficient to facilitate locomotor function and/ or voiding of bladder and/or bowel.

27 Claims, 20 Drawing Sheets

(56) References Cited

U.S. PATENT DOCUMENTS

| | | |
|---|---|---|
| 4,285,347 A | 8/1981 | Hess |
| 4,340,063 A | 7/1982 | Maurer |
| 4,379,462 A | 4/1983 | Borkan et al. |
| 4,414,986 A | 11/1983 | Dickhudt et al. |
| 4,538,624 A | 9/1985 | Tarjan |
| 4,549,556 A | 10/1985 | Tajan et al. |
| 4,559,948 A | 12/1985 | Liss et al. |
| 4,573,481 A | 3/1986 | Bullara et al. |
| 4,800,898 A | 1/1989 | Hess et al. |
| 4,934,368 A | 6/1990 | Lynch |
| 4,969,452 A | 11/1990 | Petrofsky et al. |
| 5,002,053 A | 3/1991 | Garcia-Rill et al. |
| 5,031,618 A | 7/1991 | Mullett |
| 5,066,272 A * | 11/1991 | Eaton ............. A61N 2/006 600/14 |
| 5,081,989 A | 1/1992 | Graupe et al. |
| 5,121,754 A | 6/1992 | Mullett |
| 5,344,439 A | 9/1994 | Otten |
| 5,354,320 A | 10/1994 | Schaldach et al. |
| 5,374,285 A | 12/1994 | Vaiani et al. |
| 5,417,719 A | 5/1995 | Hull et al. |
| 5,476,441 A | 12/1995 | Durfee et al. |
| 5,562,718 A | 10/1996 | Palermo |
| 5,643,330 A | 7/1997 | Holsheimer et al. |
| 5,733,322 A | 3/1998 | Starkebaum |
| 5,983,141 A | 11/1999 | Sluijter et al. |
| 6,066,163 A | 5/2000 | John |
| 6,104,957 A | 8/2000 | Alo et al. |
| 6,122,548 A | 9/2000 | Starkebaum et al. |
| 6,308,103 B1 | 10/2001 | Gielen |
| 6,319,241 B1 | 11/2001 | King et al. |
| 6,463,327 B1 | 10/2002 | Lurie et al. |
| 6,470,213 B1 | 10/2002 | Alley |
| 6,500,110 B1 * | 12/2002 | Davey ............. A61N 2/02 128/DIG. 25 |
| 6,503,231 B1 | 1/2003 | Prausnitz et al. |
| 6,505,074 B2 | 1/2003 | Boveja et al. |
| 6,516,227 B1 | 2/2003 | Meadows et al. |
| 6,551,849 B1 | 4/2003 | Kenney |
| 6,587,724 B2 | 7/2003 | Mann |
| 6,662,053 B2 | 12/2003 | Borkan |
| 6,666,831 B1 | 12/2003 | Edgerton et al. |
| 6,685,729 B2 | 2/2004 | Gonzalez |
| 6,819,956 B2 | 11/2004 | DiLorenzo |
| 6,839,594 B2 | 1/2005 | Cohen et al. |
| 6,862,479 B1 | 3/2005 | Whitehurst et al. |
| 6,871,099 B1 | 3/2005 | Whitehurst et al. |
| 6,892,098 B2 | 5/2005 | Ayal et al. |
| 6,895,280 B2 | 5/2005 | Meadows et al. |
| 6,895,283 B2 | 5/2005 | Erickson et al. |
| 6,937,891 B2 | 8/2005 | Leinders et al. |
| 6,950,706 B2 | 9/2005 | Rodriguez et al. |
| 6,975,907 B2 | 12/2005 | Zanakis et al. |
| 6,988,006 B2 | 1/2006 | King et al. |
| 6,999,820 B2 | 2/2006 | Jordan |
| 7,020,521 B1 | 3/2006 | Brewer et al. |
| 7,024,247 B2 | 4/2006 | Gliner et al. |
| 7,035,690 B2 | 4/2006 | Goetz |
| 7,047,084 B2 | 5/2006 | Erickson et al. |
| 7,065,408 B2 | 6/2006 | Herman et al. |
| 7,096,070 B1 | 8/2006 | Jenkins et al. |
| 7,110,820 B2 | 9/2006 | Tcheng et al. |
| 7,127,287 B2 | 10/2006 | Duncan et al. |
| 7,127,296 B2 | 10/2006 | Bradley |
| 7,127,297 B2 | 10/2006 | Law et al. |
| 7,153,242 B2 | 12/2006 | Goffer |
| 7,184,837 B2 | 2/2007 | Goetz |
| 7,200,443 B2 | 4/2007 | Faul |
| 7,209,787 B2 | 4/2007 | DiLorenzo |
| 7,228,179 B2 | 6/2007 | Campen et al. |
| 7,239,920 B1 | 7/2007 | Thacker et al. |
| 7,251,529 B2 | 7/2007 | Greenwood-Van Meerveld |
| 7,252,090 B2 | 8/2007 | Goetz |
| 7,313,440 B2 | 12/2007 | Miesel et al. |
| 7,324,853 B2 | 1/2008 | Ayal et al. |
| 7,330,760 B2 | 2/2008 | Heruth et al. |
| 7,337,005 B2 | 2/2008 | Kim et al. |
| 7,337,006 B2 | 2/2008 | Kim et al. |
| 7,381,192 B2 | 6/2008 | Brodard et al. |
| 7,415,309 B2 | 8/2008 | Mcintyre |
| 7,463,928 B2 | 12/2008 | Lee et al. |
| 7,467,016 B2 | 12/2008 | Colborn |
| 7,493,170 B1 | 2/2009 | Segel et al. |
| 7,496,404 B2 | 2/2009 | Meadows et al. |
| 7,502,652 B2 | 3/2009 | Gaunt et al. |
| 7,536,226 B2 | 5/2009 | Williams et al. |
| 7,544,185 B2 | 6/2009 | Bengtsson |
| 7,584,000 B2 | 9/2009 | Erickson |
| 7,590,454 B2 | 9/2009 | Garabedian et al. |
| 7,603,178 B2 | 10/2009 | North et al. |
| 7,628,750 B2 | 12/2009 | Cohen et al. |
| 7,660,636 B2 | 2/2010 | Castel et al. |
| 7,697,995 B2 | 4/2010 | Cross et al. |
| 7,729,781 B2 | 6/2010 | Swoyer et al. |
| 7,734,340 B2 | 6/2010 | De Ridder |
| 7,734,351 B2 | 6/2010 | Testerman et al. |
| 7,769,463 B2 | 8/2010 | Katsnelson |
| 7,797,057 B2 | 9/2010 | Harris |
| 7,801,601 B2 | 9/2010 | Maschino et al. |
| 7,813,803 B2 | 10/2010 | Heruth et al. |
| 7,813,809 B2 | 10/2010 | Strother et al. |
| 7,856,264 B2 | 12/2010 | Firlik et al. |
| 7,877,146 B2 | 1/2011 | Rezai et al. |
| 7,890,182 B2 | 2/2011 | Parramon et al. |
| 7,949,395 B2 | 5/2011 | Kuzma |
| 7,949,403 B2 | 5/2011 | Palermo et al. |
| 7,987,000 B2 | 7/2011 | Moffitt et al. |
| 7,991,465 B2 | 8/2011 | Bartic et al. |
| 8,019,427 B2 | 9/2011 | Moffitt |
| 8,050,773 B2 | 11/2011 | Zhu |
| 8,108,052 B2 | 1/2012 | Boling |
| 8,131,358 B2 | 3/2012 | Moffitt et al. |
| 8,155,750 B2 | 4/2012 | Jaax et al. |
| 8,170,660 B2 | 5/2012 | Dacey, Jr. et al. |
| 8,190,262 B2 | 5/2012 | Gerber et al. |
| 8,195,304 B2 | 6/2012 | Strother et al. |
| 8,214,048 B1 | 7/2012 | Whitehurst et al. |
| 8,229,565 B2 | 7/2012 | Kim et al. |
| 8,239,038 B2 | 8/2012 | Wolf, II |
| 8,260,436 B2 | 9/2012 | Gerber et al. |
| 8,271,099 B1 | 9/2012 | Swanson |
| 8,295,936 B2 | 10/2012 | Wahlstrand et al. |
| 8,311,644 B2 | 11/2012 | Moffitt et al. |
| 8,332,029 B2 | 12/2012 | Glukhovsky et al. |
| 8,346,366 B2 | 1/2013 | Arle et al. |
| 8,352,036 B2 | 1/2013 | DiMarco et al. |
| 8,355,791 B2 | 1/2013 | Moffitt |
| 8,355,797 B2 | 1/2013 | Caparso et al. |
| 8,364,273 B2 | 1/2013 | De Ridder |
| 8,369,961 B2 | 2/2013 | Christman et al. |
| 8,412,345 B2 | 4/2013 | Moffitt |
| 8,428,728 B2 | 4/2013 | Sachs |
| 8,442,655 B2 | 5/2013 | Moffitt et al. |
| 8,452,406 B2 | 5/2013 | Arcot-Krishnamurthy et al. |
| 8,588,884 B2 | 11/2013 | Hegde et al. |
| 8,700,145 B2 | 4/2014 | Kilgard et al. |
| 8,712,546 B2 | 4/2014 | Kim et al. |
| 8,750,957 B2 | 6/2014 | Tang et al. |
| 8,805,542 B2 | 8/2014 | Tai et al. |
| 9,072,891 B1 * | 7/2015 | Rao ............. A61N 2/006 |
| 9,101,769 B2 | 8/2015 | Edgerton et al. |
| 9,205,259 B2 | 12/2015 | Kim et al. |
| 9,205,260 B2 | 12/2015 | Kim et al. |
| 9,205,261 B2 | 12/2015 | Kim et al. |
| 9,272,143 B2 | 3/2016 | Libbus et al. |
| 9,283,391 B2 | 3/2016 | Ahmed |
| 9,393,409 B2 | 7/2016 | Edgerton et al. |
| 9,415,218 B2 | 8/2016 | Edgerton et al. |
| 9,610,442 B2 | 4/2017 | Yoo et al. |
| 9,993,642 B2 | 6/2018 | Gerasimenko et al. |
| 10,137,299 B2 | 11/2018 | Lu et al. |
| 10,751,533 B2 | 8/2020 | Edgerton et al. |
| 10,773,074 B2 | 9/2020 | Liu et al. |
| 10,806,927 B2 | 10/2020 | Edgerton et al. |

(56) References Cited

U.S. PATENT DOCUMENTS

| | | |
|---|---|---|
| 2002/0055779 A1 | 5/2002 | Andrews |
| 2002/0111661 A1 | 8/2002 | Cross et al. |
| 2002/0115945 A1 | 8/2002 | Herman et al. |
| 2002/0193843 A1 | 12/2002 | Hill et al. |
| 2003/0032992 A1 | 2/2003 | Thacker et al. |
| 2003/0078633 A1 | 4/2003 | Firlik et al. |
| 2003/0100933 A1 | 5/2003 | Ayal et al. |
| 2003/0158583 A1* | 8/2003 | Burnett .............. A61N 1/36071 607/2 |
| 2003/0220679 A1 | 11/2003 | Han |
| 2003/0233137 A1 | 12/2003 | Paul, Jr. |
| 2004/0039425 A1 | 2/2004 | Greenwood-Van Meerveld |
| 2004/0044380 A1 | 3/2004 | Bruninga et al. |
| 2004/0111118 A1 | 6/2004 | Hill et al. |
| 2004/0111126 A1* | 6/2004 | Tanagho ............ A61N 1/36017 607/40 |
| 2004/0122483 A1 | 6/2004 | Nathan et al. |
| 2004/0127954 A1 | 7/2004 | McDonald et al. |
| 2004/0133248 A1 | 7/2004 | Frei et al. |
| 2004/0138518 A1 | 7/2004 | Rise et al. |
| 2005/0004622 A1 | 1/2005 | Cullen et al. |
| 2005/0070982 A1 | 3/2005 | Heruth et al. |
| 2005/0075669 A1 | 4/2005 | King |
| 2005/0075678 A1 | 4/2005 | Faul |
| 2005/0102007 A1 | 5/2005 | Ayal et al. |
| 2005/0113882 A1 | 5/2005 | Cameron et al. |
| 2005/0119713 A1 | 6/2005 | Whitehurst et al. |
| 2005/0125045 A1 | 6/2005 | Brighton et al. |
| 2005/0209655 A1 | 9/2005 | Bradley et al. |
| 2005/0246004 A1 | 11/2005 | Cameron et al. |
| 2005/0278000 A1* | 12/2005 | Strother ............... A61B 5/0031 607/48 |
| 2006/0003090 A1 | 1/2006 | Rodger et al. |
| 2006/0041295 A1 | 2/2006 | Osypka |
| 2006/0089696 A1 | 4/2006 | Olsen et al. |
| 2006/0100671 A1 | 5/2006 | Ridder |
| 2006/0111754 A1 | 5/2006 | Rezai et al. |
| 2006/0122678 A1 | 6/2006 | Olsen et al. |
| 2006/0142816 A1 | 6/2006 | Fruitman et al. |
| 2006/0142822 A1 | 6/2006 | Tulgar |
| 2006/0149333 A1* | 7/2006 | Tanagho ............ A61N 1/36017 607/41 |
| 2006/0149337 A1 | 7/2006 | John |
| 2006/0239482 A1 | 10/2006 | Hatoum |
| 2006/0282127 A1 | 12/2006 | Zealear |
| 2007/0016097 A1 | 1/2007 | Farquhar et al. |
| 2007/0016266 A1 | 1/2007 | Paul, Jr. |
| 2007/0049814 A1 | 3/2007 | Muccio |
| 2007/0055337 A1 | 3/2007 | Tanrisever |
| 2007/0060954 A1 | 3/2007 | Cameron et al. |
| 2007/0060980 A1 | 3/2007 | Strother et al. |
| 2007/0073357 A1 | 3/2007 | Rooney et al. |
| 2007/0083240 A1 | 4/2007 | Peterson et al. |
| 2007/0156179 A1 | 7/2007 | S.E. |
| 2007/0168008 A1 | 7/2007 | Olsen |
| 2007/0179534 A1 | 8/2007 | Firlik et al. |
| 2007/0191709 A1 | 8/2007 | Swanson |
| 2007/0208381 A1 | 9/2007 | Hill et al. |
| 2007/0233204 A1 | 10/2007 | Lima et al. |
| 2007/0255372 A1 | 11/2007 | Metzler et al. |
| 2007/0265679 A1 | 11/2007 | Bradley et al. |
| 2007/0265691 A1 | 11/2007 | Swanson |
| 2007/0276449 A1 | 11/2007 | Gunter et al. |
| 2007/0276450 A1 | 11/2007 | Meadows et al. |
| 2008/0021513 A1 | 1/2008 | Thacker et al. |
| 2008/0046049 A1 | 2/2008 | Skubitz et al. |
| 2008/0051851 A1 | 2/2008 | Lin |
| 2008/0071325 A1 | 3/2008 | Bradley |
| 2008/0103579 A1 | 5/2008 | Gerber |
| 2008/0140152 A1 | 6/2008 | Imran et al. |
| 2008/0140169 A1 | 6/2008 | Imran |
| 2008/0147143 A1 | 6/2008 | Popovic et al. |
| 2008/0154329 A1 | 6/2008 | Pyles et al. |
| 2008/0183224 A1 | 7/2008 | Barolat |
| 2008/0200749 A1* | 8/2008 | Zheng ................. A61N 2/006 600/13 |
| 2008/0202940 A1 | 8/2008 | Jiang et al. |
| 2008/0207985 A1 | 8/2008 | Farone |
| 2008/0215113 A1 | 9/2008 | Pawlowicz |
| 2008/0221653 A1 | 9/2008 | Agrawal et al. |
| 2008/0228241 A1 | 9/2008 | Sachs |
| 2008/0228250 A1 | 9/2008 | Mironer |
| 2008/0234791 A1 | 9/2008 | Arle et al. |
| 2008/0279896 A1 | 11/2008 | Heinen et al. |
| 2009/0012436 A1 | 1/2009 | Lanfermann et al. |
| 2009/0093854 A1 | 4/2009 | Leung et al. |
| 2009/0112281 A1 | 4/2009 | Miyazawa et al. |
| 2009/0118365 A1 | 5/2009 | Benson, III et al. |
| 2009/0157141 A1 | 6/2009 | Chiao et al. |
| 2009/0198305 A1 | 8/2009 | Naroditsky et al. |
| 2009/0204173 A1 | 8/2009 | Fang et al. |
| 2009/0270960 A1 | 10/2009 | Zhao et al. |
| 2009/0281599 A1 | 11/2009 | Thacker et al. |
| 2009/0299166 A1 | 12/2009 | Nishida et al. |
| 2009/0299167 A1 | 12/2009 | Seymour |
| 2009/0306491 A1 | 12/2009 | Haggers |
| 2010/0004715 A1 | 1/2010 | Fahey |
| 2010/0023103 A1 | 1/2010 | Elborno |
| 2010/0042193 A1 | 2/2010 | Slavin |
| 2010/0070007 A1 | 3/2010 | Parker et al. |
| 2010/0114239 A1 | 5/2010 | McDonald et al. |
| 2010/0125313 A1 | 5/2010 | Lee et al. |
| 2010/0137938 A1 | 6/2010 | Kishawi et al. |
| 2010/0145428 A1 | 6/2010 | Cameron et al. |
| 2010/0152811 A1 | 6/2010 | Flaherty |
| 2010/0185253 A1 | 7/2010 | Dimarco et al. |
| 2010/0198298 A1 | 8/2010 | Glukhovsky et al. |
| 2010/0217355 A1 | 8/2010 | Tass et al. |
| 2010/0228310 A1 | 9/2010 | Shuros et al. |
| 2010/0241191 A1 | 9/2010 | Testerman et al. |
| 2010/0268299 A1 | 10/2010 | Farone |
| 2010/0274312 A1 | 10/2010 | Alataris et al. |
| 2010/0305660 A1 | 12/2010 | Hegi et al. |
| 2010/0318168 A1 | 12/2010 | Bighetti |
| 2010/0331925 A1 | 12/2010 | Peterson |
| 2011/0029040 A1 | 2/2011 | Walker et al. |
| 2011/0040349 A1 | 2/2011 | Graupe |
| 2011/0054567 A1 | 3/2011 | Lane et al. |
| 2011/0054568 A1 | 3/2011 | Lane et al. |
| 2011/0054579 A1 | 3/2011 | Kumar et al. |
| 2011/0125203 A1 | 5/2011 | Simon et al. |
| 2011/0130804 A1 | 6/2011 | Lin et al. |
| 2011/0152967 A1 | 6/2011 | Simon et al. |
| 2011/0160810 A1 | 6/2011 | Griffith |
| 2011/0166546 A1 | 7/2011 | Jaax et al. |
| 2011/0184488 A1 | 7/2011 | De Ridder |
| 2011/0184489 A1 | 7/2011 | Nicolelis et al. |
| 2011/0218594 A1 | 9/2011 | Doran et al. |
| 2011/0224665 A1 | 9/2011 | Crosby et al. |
| 2011/0224752 A1 | 9/2011 | Rolston et al. |
| 2011/0224753 A1 | 9/2011 | Palermo et al. |
| 2011/0224757 A1 | 9/2011 | Zdeblick et al. |
| 2011/0230701 A1 | 9/2011 | Simon et al. |
| 2011/0230702 A1 | 9/2011 | Honour |
| 2011/0245734 A1 | 10/2011 | Wagner et al. |
| 2011/0276107 A1 | 11/2011 | Simon et al. |
| 2011/0288609 A1 | 11/2011 | Tehrani et al. |
| 2011/0295100 A1 | 12/2011 | Rolston et al. |
| 2012/0006793 A1 | 1/2012 | Swanson |
| 2012/0029528 A1 | 2/2012 | Macdonald et al. |
| 2012/0035684 A1 | 2/2012 | Thompson et al. |
| 2012/0101326 A1* | 4/2012 | Simon ............... A61N 1/36007 600/9 |
| 2012/0109251 A1 | 5/2012 | Lebedev et al. |
| 2012/0109295 A1 | 5/2012 | Fan |
| 2012/0123293 A1 | 5/2012 | Shah et al. |
| 2012/0126392 A1 | 5/2012 | Kalvesten et al. |
| 2012/0165899 A1 | 6/2012 | Gliner |
| 2012/0172946 A1 | 7/2012 | Altaris et al. |
| 2012/0179222 A1 | 7/2012 | Jaax et al. |
| 2012/0185020 A1 | 7/2012 | Simon et al. |
| 2012/0197338 A1 | 8/2012 | Su et al. |
| 2012/0221073 A1 | 8/2012 | Southwell et al. |

(56) References Cited

U.S. PATENT DOCUMENTS

| | | |
|---|---|---|
| 2012/0232615 A1 | 9/2012 | Barolat et al. |
| 2012/0252874 A1 | 10/2012 | Feinstein et al. |
| 2012/0259380 A1 | 10/2012 | Pyles |
| 2012/0277824 A1 | 11/2012 | Li |
| 2012/0277834 A1 | 11/2012 | Mercanzini et al. |
| 2012/0283697 A1 | 11/2012 | Kim et al. |
| 2012/0283797 A1 | 11/2012 | De Ridder |
| 2012/0302821 A1* | 11/2012 | Burnett ............... A61N 1/0492 600/14 |
| 2012/0310305 A1 | 12/2012 | Kaula et al. |
| 2012/0310315 A1 | 12/2012 | Savage et al. |
| 2012/0330391 A1 | 12/2012 | Bradley et al. |
| 2013/0012853 A1 | 1/2013 | Brown |
| 2013/0013041 A1 | 1/2013 | Glukhovsky et al. |
| 2013/0030319 A1 | 1/2013 | Hettrick et al. |
| 2013/0030501 A1 | 1/2013 | Feler et al. |
| 2013/0053734 A1 | 2/2013 | Barriskill et al. |
| 2013/0053922 A1 | 2/2013 | Ahmed et al. |
| 2013/0066392 A1 | 3/2013 | Simon et al. |
| 2013/0085317 A1 | 4/2013 | Feinstein |
| 2013/0110196 A1 | 5/2013 | Alataris et al. |
| 2013/0123568 A1 | 5/2013 | Hamilton et al. |
| 2013/0123659 A1 | 5/2013 | Bartol et al. |
| 2013/0165991 A1 | 6/2013 | Kim et al. |
| 2013/0197408 A1 | 8/2013 | Goldfarb et al. |
| 2013/0204324 A1 | 8/2013 | Thacker et al. |
| 2013/0253299 A1 | 9/2013 | Weber et al. |
| 2013/0253611 A1 | 9/2013 | Lee et al. |
| 2013/0268016 A1 | 10/2013 | Xi et al. |
| 2013/0268021 A1 | 10/2013 | Moffitt |
| 2013/0281890 A1 | 10/2013 | Mishelevich |
| 2013/0289446 A1 | 10/2013 | Stone et al. |
| 2013/0303873 A1 | 11/2013 | Voros et al. |
| 2013/0304159 A1 | 11/2013 | Simon et al. |
| 2013/0310911 A1 | 11/2013 | Tai et al. |
| 2014/0031893 A1 | 1/2014 | Walker et al. |
| 2014/0046407 A1 | 2/2014 | Ben-Ezra et al. |
| 2014/0058490 A1 | 2/2014 | DiMarco |
| 2014/0066950 A1 | 3/2014 | Macdonald et al. |
| 2014/0067007 A1 | 3/2014 | Drees et al. |
| 2014/0067354 A1 | 3/2014 | Kaula et al. |
| 2014/0081071 A1 | 3/2014 | Simon et al. |
| 2014/0100633 A1 | 4/2014 | Mann et al. |
| 2014/0107397 A1 | 4/2014 | Simon et al. |
| 2014/0107398 A1 | 4/2014 | Simon et al. |
| 2014/0114374 A1 | 4/2014 | Rooney et al. |
| 2014/0163640 A1 | 6/2014 | Edgerton et al. |
| 2014/0180361 A1 | 6/2014 | Burdick et al. |
| 2014/0213842 A1 | 7/2014 | Simon et al. |
| 2014/0236257 A1 | 8/2014 | Parker et al. |
| 2014/0296752 A1* | 10/2014 | Edgerton ........... A61N 1/36014 601/21 |
| 2014/0303901 A1 | 10/2014 | Sadeh |
| 2014/0316484 A1* | 10/2014 | Edgerton ........... A61N 1/36025 607/46 |
| 2014/0316503 A1 | 10/2014 | Tai et al. |
| 2014/0324118 A1 | 10/2014 | Simon et al. |
| 2014/0330067 A1* | 11/2014 | Jordan .................. A61N 2/006 600/13 |
| 2014/0330335 A1 | 11/2014 | Errico et al. |
| 2014/0336722 A1 | 11/2014 | Rocon De Lima et al. |
| 2014/0357936 A1 | 12/2014 | Simon et al. |
| 2015/0005840 A1 | 1/2015 | Pal et al. |
| 2015/0065559 A1 | 3/2015 | Feinstein et al. |
| 2015/0165226 A1 | 6/2015 | Simon et al. |
| 2015/0182784 A1 | 7/2015 | Barriskill et al. |
| 2015/0190634 A1 | 7/2015 | Rezai et al. |
| 2015/0231396 A1 | 8/2015 | Burdick et al. |
| 2015/0265830 A1 | 9/2015 | Simon et al. |
| 2016/0030737 A1 | 2/2016 | Gerasimenko et al. |
| 2016/0030748 A1 | 2/2016 | Edgerton et al. |
| 2016/0045727 A1 | 2/2016 | Rezai et al. |
| 2016/0045731 A1 | 2/2016 | Simon et al. |
| 2016/0074663 A1 | 3/2016 | De Ridder |
| 2016/0121109 A1 | 5/2016 | Edgerton et al. |
| 2016/0121114 A1 | 5/2016 | Simon et al. |
| 2016/0121116 A1 | 5/2016 | Simon et al. |
| 2016/0175586 A1 | 6/2016 | Edgerton et al. |
| 2016/0220813 A1 | 8/2016 | Edgerton et al. |
| 2016/0235977 A1 | 8/2016 | Lu et al. |
| 2016/0271413 A1 | 9/2016 | Vallejo et al. |
| 2016/0339239 A1 | 11/2016 | Yoo et al. |
| 2017/0007831 A1 | 1/2017 | Edgerton et al. |
| 2017/0157389 A1 | 6/2017 | Tai et al. |
| 2017/0161454 A1 | 6/2017 | Grill et al. |
| 2017/0246450 A1 | 8/2017 | Liu et al. |
| 2017/0246452 A1 | 8/2017 | Liu et al. |
| 2017/0274209 A1 | 9/2017 | Edgerton et al. |
| 2017/0296837 A1 | 10/2017 | Jin |
| 2018/0185642 A1 | 7/2018 | Lu |
| 2018/0256906 A1* | 9/2018 | Pivonka ................ A61N 2/006 |
| 2018/0280693 A1 | 10/2018 | Edgerton et al. |
| 2018/0361146 A1 | 12/2018 | Gerasimenko et al. |
| 2019/0022371 A1 | 1/2019 | Chang et al. |
| 2019/0167987 A1 | 6/2019 | Lu et al. |
| 2019/0381313 A1 | 12/2019 | Lu |
| 2020/0155865 A1 | 5/2020 | Lu |

FOREIGN PATENT DOCUMENTS

| | | |
|---|---|---|
| CA | 2 856 202 A1 | 5/2013 |
| CA | 2 864 473 A1 | 5/2013 |
| EP | 2661307 A2 | 11/2013 |
| EP | 2968940 A1 | 1/2016 |
| JP | H03-26620 A | 2/1991 |
| JP | 2007-526798 A | 9/2007 |
| JP | 2008-543429 A | 12/2008 |
| RU | 2130326 C1 | 5/1999 |
| RU | 2141851 C1 | 11/1999 |
| RU | 2160127 C1 | 12/2000 |
| RU | 2178319 C2 | 1/2002 |
| RU | 2192897 C2 | 11/2002 |
| RU | 2001102533 | 11/2002 |
| RU | 2226114 C1 | 3/2004 |
| RU | 2258496 C2 | 8/2005 |
| RU | 2361631 C2 | 7/2009 |
| RU | 2368401 C1 | 9/2009 |
| RU | 2387467 C1 | 4/2010 |
| RU | 2396995 C2 | 8/2010 |
| RU | 2397788 C2 | 8/2010 |
| RU | 2445990 C1 | 3/2012 |
| RU | 2471518 C2 | 1/2013 |
| RU | 2475283 C2 | 2/2013 |
| WO | WO 97/047357 A1 | 12/1997 |
| WO | WO 03/026735 A2 | 4/2003 |
| WO | WO 03/092795 A2 | 11/2003 |
| WO | WO 2004/087116 A2 | 10/2004 |
| WO | WO 2005/051306 A2 | 6/2005 |
| WO | WO 2005/065768 A1 | 7/2005 |
| WO | WO 2005/087307 A2 | 9/2005 |
| WO | WO 2006/138069 A1 | 12/2006 |
| WO | WO 2007/007058 A1 | 1/2007 |
| WO | WO 2007/107831 A2 | 9/2007 |
| WO | WO 2008/109862 A1 | 9/2008 |
| WO | WO 2008/121891 A1 | 10/2008 |
| WO | WO 2009/042217 A1 | 4/2009 |
| WO | WO 2009/111142 A2 | 9/2009 |
| WO | WO 2010/055421 A1 | 5/2010 |
| WO | WO 2010/114998 A1 | 10/2010 |
| WO | WO 2010/124128 A1 | 10/2010 |
| WO | WO 2012/094346 A2 | 7/2012 |
| WO | WO 2012/100260 A2 | 7/2012 |
| WO | WO 2012/129574 A2 | 9/2012 |
| WO | WO 2013/071307 A1 | 5/2013 |
| WO | WO 2013/071309 A1 | 5/2013 |
| WO | WO 2013/188965 A1 | 12/2013 |
| WO | WO 2014/144785 A1 | 9/2014 |
| WO | WO 2015/048563 A2 | 4/2015 |
| WO | WO 2016/029159 A2 | 2/2016 |
| WO | WO 2016/033369 A1 | 3/2016 |
| WO | WO 2016/033372 A1 | 3/2016 |
| WO | WO 2017/011410 A1 | 1/2017 |
| WO | WO 2017/024276 A1 | 2/2017 |
| WO | WO 2017/035512 A1 | 3/2017 |

(56) References Cited

FOREIGN PATENT DOCUMENTS

| WO | WO 2017/044904 A1 | 3/2017 |
|---|---|---|
| WO | WO 2018/106843 A1 | 6/2018 |
| WO | WO 2018/140531 A1 | 8/2018 |
| WO | WO 2018/217791 A1 | 11/2018 |
| WO | WO 2020/041502 A1 | 2/2020 |
| WO | WO 2020/041633 A1 | 2/2020 |
| WO | WO 2020/236946 A1 | 11/2020 |

OTHER PUBLICATIONS

U.S. Office Action dated Apr. 8, 2015 issued in U.S. Appl. No. 14/355,812.
U.S. Final Office Action dated Sep. 21, 2015 issued in U.S. Appl. No. 14/355,812.
U.S. Notice of Allowance dated Apr. 13, 2016 issued in U.S. Appl. No. 14/355,812.
U.S. Office Action dated Oct. 18, 2016 issued in U.S. Appl. No. 15/208,529.
U.S. Final Office Action dated Jul. 13, 2017 issued in U.S. Appl. No. 15/208,529.
U.S. Office Action dated Jul. 27, 2018 issued in U.S. Appl. No. 15/208,529.
U.S. Office Action dated Oct. 3, 2017 issued in U.S. Appl. No. 15/025,201.
U.S. Notice of Allowance dated Aug. 1, 2018 issued in U.S. Appl. No. 15/025,201.
U.S. Office Action dated Jul. 13, 2016 issued in U.S. Appl. No. 14/775,618.
U.S. Final Office Action dated Apr. 25, 2017 issued in U.S. Appl. No. 14/775,618.
U.S. Notice of Allowance dated Jan. 18, 2018 issued in U.S. Appl. No. 14/775,618.
PCT International Search Report dated Jul. 30, 2012 issued in PCT/US2012/020112.
PCT International Preliminary Report on Patentability and Written Opinion dated Jul. 10, 2013 issued in PCT/US2012/020112.
PCT International Search Report and Written Opinion dated Mar. 19, 2013 issued in PCT/US2012/064878.
PCT International Preliminary Report on Patentability dated May 22, 2014 issued in PCT/US2012/064878.
Australian Patent Examination Report No. 1 dated Jul. 11, 2016 issued in AU 2012334926.
Canadian Office Action dated Aug. 31, 2018 issued in CA 2,864,473.
European Communication pursuant to Rule 114(2) EPC regarding observations by a third party dated Mar. 27, 2015 issued in EP 12 847 885.6.
European Extended Search Report dated May 6, 2015 issued in EP 12 847 885.6.
European Office Action dated Apr. 15, 2016 issued in EP 12 847 885.6.
European Reply to Communication dated Apr. 15, 2016 dated Oct. 24, 2016 in EP 12 847 885.6.
European Second Office Action dated Feb. 16, 2017 issued in EP 12 847 885.6.
PCT Declaration of Non-Establishment of International Search Report and Written Opinion dated Dec. 24, 2014 issued in PCT/US2014/057886.
PCT International Preliminary Report on Patentability and Written Opinion dated Apr. 7, 2016 issued in PCT/US2014/057886.
Australian Examination report No. 1 dated Jan. 11, 2019 issued in AU 2014324660.
European Extended Search Report dated May 10, 2017 issued in EP 14849355.4.
European Office Action dated Jul. 20, 2018 issued in EP 14849355.4.
PCT International Search Report and Written Opinion dated Aug. 6, 2014 issued in PCT/US2014/029340.
PCT International Preliminary Report on Patentability dated Sep. 24, 2015 issued in PCT/US2014/029340.
Australian Patent Examination Report No. 1 dated May 11, 2018 issued in AU 2014228794.
European Extended Search Report dated Nov. 8, 2016 issued in EP 14 76 5477.6.
European Office Action dated Nov. 14, 2018 issued in EP 14 76 5477.6.
PCT International Search Report and Written Opinion dated Dec. 5, 2016 issued in PCT/US2016/045898.
PCT International Preliminary Report on Patentability and Written Opinion dated Feb. 15, 2018 issued in PCT/US2016/045898.
European Extended Search Report dated Dec. 13, 2018 issued in EP 16833973.7.
PCT International Search Report and Written Opinion dated Dec. 8, 2015 issued in PCT/US2015/047268.
PCT International Preliminary Report on Patentability and Written Opinion dated Feb. 28, 2017 issued in PCT/US2015/047268.
European Extended Search Report dated Mar. 1, 2018 issued in EP 15836927.2.
PCT International Search Report and Written Opinion dated Dec. 3, 2015 issued in PCT/US2015/047272.
PCT International Preliminary Report on Patentability and Written Opinion dated Feb. 28, 2017 issued in PCT/US2015/047272.
PCT Declaration of Non-Establishment of International Search Report and Written Opinion dated Dec. 1, 2015 issued in PCT/US2015/046378.
PCT International Preliminary Report on Patentability and Written Opinion dated Feb. 21, 2017 issued in PCT/US2015/046378.
European Extended Search Report dated Apr. 4, 2018 issued in EP 15834593.4.
PCT International Search Report and Written Opinion dated Sep. 12, 2016 issued in PCT/US2016/041802.
PCT International Preliminary Report on Patentability and Written Opinion dated Jan. 25, 2018 issued in PCT/US2016/041802.
PCT International Search Report and Written Opinion dated Dec. 5, 2016 issued in PCT/US2016/049129.
PCT International Preliminary Report on Patentability and Written Opinion dated Mar. 8, 2018 issued in PCT/US2016/049129.
PCT International Search Report and Written Opinion dated Mar. 12, 2018 issued in PCT/US2018/015098.
PCT International Search Report and Written Opinion dated Aug. 31, 2018 issued in PCT/US2018/033942.
PCT International Search Report dated Mar. 19, 2013 issued in PCT/US2012/064874.
PCT International Search Report dated Mar. 19, 2013 issued in PCT/US2012/064878.
PCT International Search Report dated Sep. 3, 2012 issued in PCT/US2012/022257.
PCT International Search Report dated Oct. 31, 2012 issued in PCT/US2012/030624.
Angeli et al. (2014) "Altering spinal cord excitability enables voluntary movements after chronic complete paralysis in humans" *Brain* 137: 1394-1409.
Courtine, Grégoire et al. (2007) "Modulation of multisegmental monosynaptic responses in a variety of leg muscles during walking and running in humans," *J. Physiol.* 582.3:1125-1139.
Danner S.M., Hofstoetter U.S., Ladenbauer J., Rattay F., and Minassian K. (Mar. 2011) "Can the human lumbar posterior columns be stimulated by transcutaneous spinal cord stimulation? A modeling study" *Europe PMC Funders Author Manuscripts, Artif Organs* 35(3):257-262, 12 pp.
DeSantana et al. (Dec. 2008) "Effectiveness of Transcutaneous Electrical Nerve Stimulation for Treatment of Hyperalgesia and Pain," *Curr Rheumatol Rep.* 10(6):492-499, 12 pp.
Dubinsky, Richard M. and Miyasaki, Janis, "Assessment: Efficacy of transcutaneous electric nerve stimulation in the treatment of pain in neurologic disorders (an evidence-based review)," Report of the Therapeutics and Technology Assessment Subcommittee of the American Academy of Neurology, (2010) *Neurology,* 74:173-176.
Fong et al. (2009) "Recovery of control of posture and locomotion after a spinal cord injury: solutions staring us in the face," *Progress in Brain Research,* Elsevier Amsterdam, NL,175:393-418.
Ganley et al., (2005) "Epidural Spinal Cord Stimulation Improves Locomotor Performance in Low ASIA C, Wheelchair-Dependent,

(56) References Cited

OTHER PUBLICATIONS

Spinal Cord-Injured Individuals: Insights from Metabolic Response," *Top. Spinal Cord Inj. Rehabil*;11(2):50-63.

Gerasimenko Y., Gorodnichev R., Machueva E., Pivovarova E., Semyenov D., Savochin A., Roy R.R., and Edgerton V.R., (Mar. 10, 2010) "Novel and Direct Access to the Human Locomotor Spinal Circuitry," *J Neurosci.* 30(10):3700-3708, PMC2847395.

Gerasimenko Y.P., Ichiyama R.M., Lavrov I.A., Courtine G., Cai L., Zhong H., Roy R.R., and Edgerton V.R. (2007) "Epidural Spinal Cord Stimulation Plus Quipazine Administration Enable Stepping in Complete Spinal Adult Rats," *J Neurophysiol.* 98:2525-2536.

Harkema et al. (2011) "Effect of Epidural stimulation of the lumbosacral spinal cord on voluntary movement, standing, and assisted stepping after motor complete paraplegia: a case study" *Lancet* 377(9781): 1938-1947; NIH Public Access Author Manuscript 17 pages [doi:10.1016/S0140-6736(11)60547-3].

Herman R., He J., D'Luzansky S., Willis W., Dilli S., (2002) "Spinal cord stimulation facilitates functional walking in a chronic, incomplete spinal cord injured," *Spinal Cord.* 40:65-68.

Hofstoetter, U.S. et al. (Aug. 2008) "Modification of Reflex Responses to Lumbar Posterior Root Stimulation by Motor Tasks in Healthy Subjects," *Artif Organs*, 32(8):644-648.

Ichiyama et al. (2005) "Hindlimb stepping movements in complete spinal rats induced by epidural spinal cord stimulation" *Neuroscience Letters*, 383:339-344.

Kitano K., Koceja D.M. (2009) "Spinal reflex in human lower leg muscles evoked by transcutaneous spinal cord stimulation," *J Neurosci Methods.* 180:111-115.

Minasian et al. (2010) "Transcutaneous stimulation of the human lumbar spinal cord: Facilitating locomotor output in spinal cord injury," *Conf. Proceedings Soc. for Neurosci.*, Abstract No. 286.19, 1 page.

Minassian et al. (Aug. 2011) "Transcutaneous spinal cord stimulation," *International Society for Restorative Neurology*, http://restorativeneurology.org/resource-center/assessments/transcutaneous-lumbar-spinal-cord-stimulation/; http://restorativeneurology.org/wp-content/uploads/2011/08/Transcutaneous-spinal-cord-stimulationiong.pdf, 6 pp.

Minassian et al. (Mar. 2007) "Posterior root-muscle reflexes elicited by transcutaneous stimulation of the human lumbosacral cord," *Muscle & Nerve* 35:327-336.

Nandra et al., (2014) "Microelectrode Implants for Spinal Cord Stimulation in Rats," *Thesis, California Institute of Technology*, Pasadena, California, Defended on Sep. 24, 2014, 104 pages.

Nandra et al., (Jan. 23, 2011) "A Parylene-Based Microelectrode Arrary Implant for Spinal Cord Stimulation in Rats," *Conf. Proc. IEEE Eng. Med. Biol. Soc.*, pp. 1007-1010.

Rodger et al., (2007) "High Density Flexible Parylene-Based Multielectrode Arrays for Retinal and Spinal Cord Stimulation," Transducers & Eurosensors, Proc. Of the 14th International Conference on Solid-State Sensors, Actuators and Microsystems, Lyon, France, Jun. 10-14, 2007, *IEEE*, pp. 1385-1388.

Seifert et al. (Nov. 1, 2002) "Restoration of Movement Using Functional Electrical Stimulation and Bayes' Theorem," *The Journal of Neuroscience*, 22(1):9465-9474.

Tanabe et al. (2008) "Effects of transcutaneous electrical stimulation combined with locomotion-like movement in the treatment of post-stroke gait disorder: a single-case study," 30(5):411-416 abstract, 1 page.

Ward, Alex R. (Feb. 2009) "Electrical Stimulation Using Kilohertz-Frequency Alternating Current ," (2009) *Phys Ther.*89(2):181-190 [published online Dec. 18, 2008].

U.S. Final Office Action dated Apr. 19, 2019 issued in U.S. Appl. No. 15/208,529.

U.S. Office Action dated Jul. 22, 2019 issued in U.S. Appl. No. 15/506,696.

U.S. Office Action dated Jun. 4, 2019 issued in U.S. Appl. No. 15/505,053.

Canadian Office Action dated Jul. 30, 2019 issued in CA 2,864,473.

European Office Action dated Sep. 27, 2019 issued in EP 14765477.6.

Australian Patent Examination Report No. 1 dated Jul. 18, 2019 issued in AU 2015308779.

Australian Patent Examination Report No. 1 dated Jun. 14, 2019 issued in AU 2015305237.

European Office Action dated Jul. 17, 2019 issued in EP 15834593.4.

European Extended Search Report dated Feb. 19, 2019 issued in EP 16825005.8.

PCT International Preliminary Report on Patentability and Written Opinion dated Jul. 30, 2019 issued in PCT/US2018/015098.

Edgerton and Harkema (2011) "Epidural stimulation of the spinal cord in spinal cord injury: current status and future challenges" *Expert Rev Neurother.* 11(10): 1351-1353. doi:10.1586/ern.11.129 [NIH Public Access—Author Manuscript—5 pages].

U.S. Office Action dated Oct. 28, 2019 issued in U.S. Appl. No. 15/208,529.

U.S. Notice of Allowance dated Jun. 17, 2020 issued in U.S. Appl. No. 15/208,529.

U.S. Office Action dated Apr. 10, 2020 issued in U.S. Appl. No. 16/200,467.

U.S. Office Action dated Jan. 8, 2020 issued in U.S. Appl. No. 15/975,678.

U.S. Office Action dated Oct. 31, 2019 issued in U.S. Appl. No. 15/750,499.

U.S. Notice of Allowance dated May 4, 2020 issued in U.S. Appl. No. 15/506,696.

U.S. Notice of Allowance dated Feb. 13, 2020 issued in U.S. Appl. No. 15/505,053.

U.S. 2nd Notice of Allowance dated Jun. 4, 2020 issued in U.S. Appl. No. 15/505,053.

U.S. Office Action dated Apr. 7, 2020 issued in U.S. Appl. No. 15/740,323.

Australian Examination report No. 2 dated Nov. 7, 2019 issued in AU 2014324660.

Australian Examination report No. 3 dated Jan. 6, 2020 issued in AU 2014324660.

Australian Patent Examination Report No. 1 dated Jan. 6, 2020 issued in AU 2019206059.

Canadian Office Action dated May 7, 2020 issued in CA 2,906,779.

Australian Patent Examination Report No. 2 dated May 20, 2020 issued in AU 2015308779.

European Extended Search Report dated Apr. 21, 2020 issued in EP 19201998.2.

Australian Patent Examination Report No. 2 dated Apr. 17, 2020 issued in AU 2015305237.

PCT International Preliminary Report on Patentability and Written Opinion dated Nov. 26, 2019 issued in PCT/US2018/033942.

PCT International Search Report and Written Opinion dated Nov. 14, 2019 issued in PCT/US2019/047777.

PCT International Search Report and Written Opinion dated Nov. 21, 2019 issued in PCT/US2019/047551.

Drummond, et al. (1996) "Thoracic impedance used for measuring chest wall movement in postoperative patients," *British Journal of Anaesthesia*, 77: 327-332.

Hovey, et al. (2006) "The Guide to Magnetic Stimulation," *The Magstim Company Ltd*, 45 pages.

Kapetanakis, et al. (2017) "Cauda Equina Syndrome Due to Lumbar Disc Herniation: a Review of Literature," *Folia Media*, 59(4): 377-86.

Kondo, et al. (1997) "Laser monitoring of chest wall displacement," *Eur Respir J.*, 10: 1865-1869.

Niu et al., (2018) "A Proof-of-Concept Study of Transcutaneous Magnetic Spinal Cord Stimulation for Neurogenic Bladder," *Scientific Reports*, 8: 12549 (12 pages).

Wang, et al. (2017) "Incidence of C5 nerve root palsy after cervical surgery," *Medicine*, 96(45), 14 pages.

U.S. Office Action dated Nov. 24, 2020 issued in U.S. Appl. No. 16/200,467.

U.S. Final Office Action dated Jul. 29, 2020 issued in U.S. Appl. No. 15/975,678.

(56) References Cited

OTHER PUBLICATIONS

U.S. Final Office Action dated Aug. 6, 2020 issued in U.S. Appl. No. 15/750,499.
U.S. Final Office Action dated Nov. 20, 2020 issued in U.S. Appl. No. 15/740,323.
U.S. Office Action dated Nov. 13, 2020 issued in U.S. Appl. No. 15/753,963.
Canadian Office Action dated Aug. 14, 2020 issued in CA 2,864,473.
Australian Examination report No. 1 dated Dec. 21, 2020 issued in AU 2020200152.
Canadian Office Action dated Nov. 27, 2020 issued in CA 2,925,754.
European Office Action dated Jul. 30, 2020 issued in EP 15834593.4.
Japanese Office Action dated Jul. 13, 2020 issued in JP 2018-501208.
European Extended Search Report dated Sep. 7, 2020 issued in EP 18744685.1.
PCT International Search Report and Written Opinion dated Oct. 14, 2020 issued in PCT/US2020/033830.
Szava et al., (Jan. 2011) "Transcutaneous electrical spinal cord stimulation: Biophysics of a new rehabilitation method after spinal cord injury", ISBN: 978-3-639-34154-6 [95 pages].

\* cited by examiner

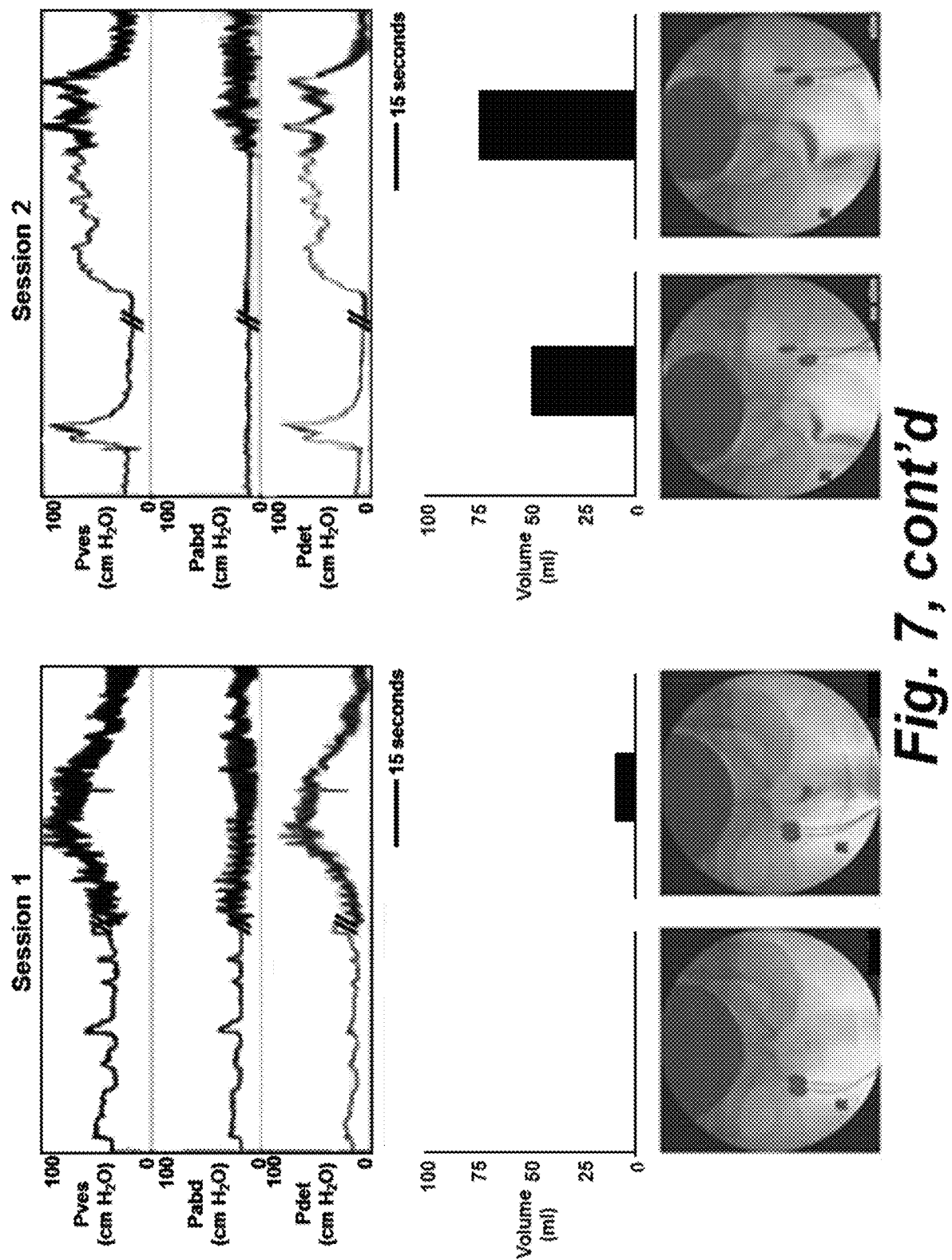
Fig. 7, cont'd

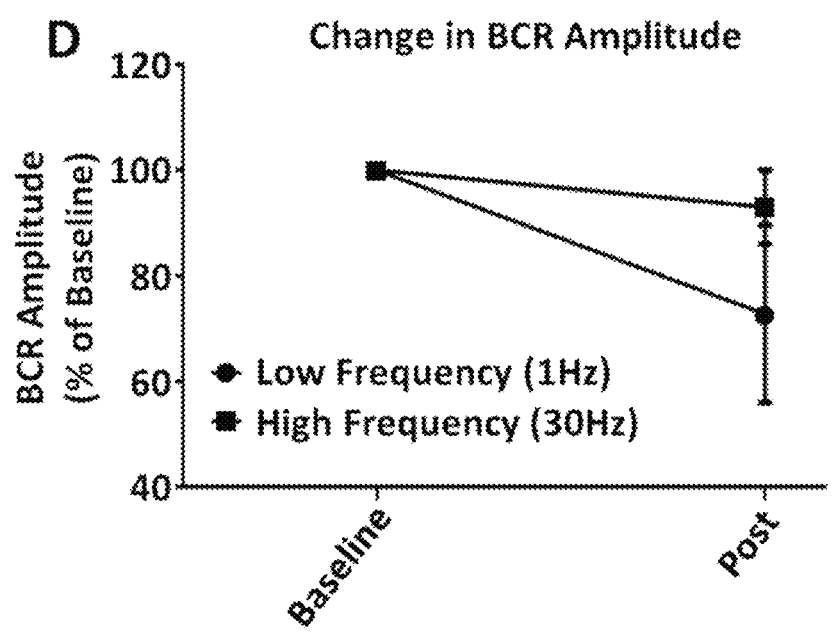
*Fig. 13, cont'd.*

MAGNETIC STIMULATION OF THE SPINAL CORD TO RESTORE CONTROL OF BLADDER AND/OR BOWEL

CROSS-REFERENCE TO RELATED APPLICATIONS

This application claims benefit of U.S. Ser. No. 62/250,841, filed on Nov. 4, 2015, which is incorporated herein by reference in its entirety for all purposes.

STATEMENT OF GOVERNMENTAL SUPPORT

This invention was made with government support under Grant Number TR000124, awarded by the National Institutes of Health, and Grant Number W81XWH-14-2-0129, awarded by the U.S. Army, Medical Research and Materiel Command. The Government has certain rights in the invention.

BACKGROUND

Spinal cord injury is a serious condition that frequently leads to long-term disabilities and significant social and economic consequences. The incidence annually is approximately 12.7 to 52.2 per 1 million (Oteir et al. (2014) *Prehospital and Disaster Med.,* 29: 399-402). The annual total cost in the US is estimated to be approximately 10 billion dollars (Ma et al. (2014) *Arch. Phys. Med. Rehab.,* 95: 986-995). Currently, there are more than 250,000 spinal cord injured individuals living in the US. Multiple studies have shown that bladder function, along with sexual function, consistently rank as the top health and quality of life priorities in these individuals (Simpson et al. (2012) *J. Neurotrauma,* 29: 1548-1555; Bloemen-Vrencken et al. (2005) *Disabil. Rehab.* 27: 1381-1389).

Individuals with spinal cord injuries must catheterize the bladder to empty it, and as a consequence, they experience high rates of urinary tract infections, obstructive uropathies and significantly reduced quality of life (Manack et al. (2011) *Neurourol. Urodynam.,* 30: 395-401; Anderson (2004) *J. Neurotrauma,* 21: 1371-1383; Nicolle (2014) *Curr. Infect. Dis. Rep.* 16: 390). Direct muscle stimulation (Bartley et al. (2013) *Nat. Rev., Urol.,* 10: 513-521) or stimulation of peripheral nerves (Brindley (1974) *J. Physiol.,* 237: 15p-16p) or rhizotomy (Van Kerrebroeck et al. (1996) *J. Neurol.,* 155: 1378-1381) to activate bladder function have been only mildly effective. Most of these interventions fail to restore the complex, orchestrated sequence of muscle contraction and relaxation that normal micturition requires (Seth et al. (2013) *Handbook Clin. Neurol.,* 117: 111-117).

Recently, we used epidural spinal cord stimulation to enhance motor function in four individuals with complete or incomplete chronic spinal cord injury. After epidural stimulation, these subjects were able to initiate voluntary movements using muscles innervated by nerves below the level of their spinal cord injury (Harkema et al. (2011) *Lancet,* 377: 1938-1947; Angeli et al. (2014) *Brain,* 137: 1394-1409). The idea behind this recovery is that spinal networks have the capacity to execute a range of complicated movements requiring detailed coordination of many motor pools with minimal or even no input from the brain. This semiautonomous capability is at the core of most of our routine movements throughout the day, which are performed with little conscious direction of the details of the patterned activity. There has already been an attempt to use this strategy to reconstruct the complex spinal cord circuitry for micturition in a rodent model (Chew et al. (2013) *Sci. Transl. Med.,* 5: 210ra155 (2013); Gad et al. (2014) *PloS One* 9: e108184). In patients with SCI, epidural stimulation of the spine seems to make these semiautonomous patterned actions accessible to volitional control.

Despite the promise that epidural stimulation has demonstrated, it still has significant limitations, foremost of which is that it is invasive. With every implantation of epidural electrodes, there is a risk of infection, inadvertent damage to the underlying neural structures, post-operative hematoma, or cerebral spinal fluid (CSF) leak. It would be ideal if we could achieve neuromodulation without invasive implants, and our lab has shown that we can activate descending motor pathways in paraplegic individuals with non-invasive transcutaneous electrical stimulation of the spine (Gerasimenko et al. (2015) *J. Neurotrauma,* 32:1968-1980). Unfortunately, even transcutaneous electrical stimulation has limitations. Electrical stimulation can cause significant pain in the area of stimulation. Moreover, the spread of the stimulating current is not restricted to neural structures, and other structures such as surrounding musculature may be activated, which may be unpleasant. Therefore, electrical stimulation over skin surfaces with normal sensation is of limited value.

Similarly, other current methods to restore bladder and bowel function are invasive requiring surgery and outcomes are often poor. For example, a common approach to bladder dysfunction is the use of a catheter to empty the bladder. While effective, if this is not done often enough (due to poor sensation, scheduling) high pressures may damage the kidneys. In addition, even with scrupulous attention to sterile technique, UTIs are inevitable. Furthermore, for subjects who are tetraplegic, self-catheterization is impossible and the patient is dependent on a care provider.

As an alternative to self-catheterization or an indwelling (Foley) catheter, a suprapubic catheter can be placed through the abdominal wall into the bladder. Long-term complications include recurrent UTIs (21%), catheter blockage (25%) resulting in multiple accident and emergency attendance (43%). Despite this, the satisfaction rate was high (72%) and most patients (89%) prefer the SPC over the urethral catheter. Attempts to modify the increased sensory tone that appears to mediate neurogenic bladder have used sacral dorsal root rhizotomies. Rhizotomies of the S2-S5 may improve bladder function, but they negatively affect anal sphincter and sexual function. More limited S3 rhizotomy can be more bladder selective. In all cases, the technique is destructive and irreversible. Sacral rhizotomy and peripheral nerve stimulation also have been attempted (see below). Ventral root microanastomosis and the Xaio procedure have been shown to have variable effects. A major disadvantage of surgical procedures is that they are inherently destructive and irreversible.

Peripheral nerve stimulators have been used with variable success. The Finetech-Brindley posterior/anterior stimulator has been used since 1978 and a recent review indicated that 411 or 500 patients were pleased with the procedure. This procedure is often accompanied by dorsal root rhizotomy, unless genital sensation and reflex erections are present. The existing devices have the disadvantages of being invasive, producing a subset of the micturition behavior, and do not result in enduring plastic changes to the circuitry that allow patients to become device independent.

Similarly with respect to motor function, there are no known commercially available products to improve motor function through accessing the spinal cord. There are products that bypass the injured spinal cord such as the brain machine interface strategy (currently not commercially available) that detects the signals from the brain and translates those signals to a robotic device that can be controlled by the brain. Or FES devices that activate the muscles to move the arms or legs. Additionally there are wearable exoskeleton devices commercially available to allow standing and stepping with hand control.

Functional electrical stimulation FES can be used effectively for stereotyped movements such as improving foot drop. However, the complexity of useful hand movements that use the intrinsic and muscles has frustrated the efforts to use FES in SCI forearm and hand movement. Furthermore FES does nothing to improve volitional control. Brain-machine computer interface (BMI/BCI) has been explored to bypass the limb and use robotics to assist people with profound paralysis such as found in locked in syndrome (Clausen (2008) *Biotechnology J.* 3(12): 1493-1501). A handful of experimental successes have allowed subject to carry out simple tasks. These systems are not as yet portable and are technologically and surgically complex requiring electrodes on the cortex preventing widespread use. Additionally, this technique does not access or improve spared normal function.

The current state of upper limb management for spinal cord injury (SCI) patients is not ideal. There is complex neurophysiology related to the control of the upper limb orchestrated at the cervical spinal cord level Yet the present day solution is to address the symptoms of SCI at the muscles of the upper limb or to bypass them. This will not likely yield meaningful recovery of arm and hand function after SCI because the muscles do not possess complex processing ability that is necessary to perform coordinated volitional movements.

SUMMARY

In various embodiments methods and devices are provided to restore the function of the injured brain, spinal cord, nerve roots, or peripheral nerves thereby regaining motor function of the extremities and/or control over the bowel and/or bladder. This strategy can be used to rehabilitate individuals without previous motor function in extremities or without previous bowel or bladder control after an injury such as a stroke, TBI, multiple sclerosis, cauda equina syndrome, amyotrophic lateral sclerosis, or spinal cord injury. Moreover, it was surprisingly discovered that magnetic stimulation can restore subsequent volitional control of bladder and/or bowel.

Various embodiments contemplated herein may include, but need not be limited to, one or more of the following:

Embodiment 1: A method of facilitating voiding or control of bladder and/or bowel in a subject with a neuromotor disorder, said method comprising: providing magnetic stimulation of the spinal cord at a location, frequency and intensity sufficient to facilitate voiding or control of bladder and/or bowel.

Embodiment 2: The method of embodiment 1, wherein said method comprises facilitating voiding or control of bladder by providing magnetic stimulation of the spinal cord at a location, frequency and intensity sufficient to facilitate voiding or control of the bladder.

Embodiment 3: The method according to any one of embodiments 1-2, wherein said magnetic stimulation comprises stimulation at a frequency ranging from about 0.5 Hz up to about 15 Hz to induce micturition.

Embodiment 4: The method of embodiment 3, wherein said magnetic stimulation is at a frequency of about 1 Hz.

Embodiment 5: The method according to any one of embodiments 1-2, wherein said magnetic stimulation comprises stimulation at a frequency from about 20 Hz up to about 100 Hz to stop or prevent micturition.

Embodiment 6: The method of embodiment 5, wherein said magnetic stimulation is at a frequency of about 30 Hz.

Embodiment 7: The method according to any one of embodiments 1-6, wherein said magnetic stimulation comprises magnetic pulses ranging in duration from about 5 μs, or from about 10 μs, or from about 15 μs, or from about 20 μs up to about 500 μs, or up to about 400 μs, or up to about 300 μs, or up to about 200 μs, or up to about 100 μs. or up to about 50 μs.

Embodiment 8: The method of embodiment 7, wherein said magnetic pulses are about 25 μs in duration.

Embodiment 9: The method according to any one of embodiments 1-8, wherein said magnetic stimulation is monophasic.

Embodiment 10: The method according to any one of embodiments 1-9, wherein a single treatment of said magnetic stimulation comprises 1, or 2, or 3, or 4, or 5, or 6, or 7, or 8, or 9, or 10 or more continuous stimulation periods.

Embodiment 11: The method of embodiment 10, wherein a single treatment of said magnetic stimulation comprises about 3 continuous stimulation periods.

Embodiment 12: The method according to any one of embodiments 10-11, wherein said continuous stimulation periods range in duration from about 10 sec, or from about 20 sec, or from about 3 sec or from about 40 sec, or from about 50 sec, or from about 1 min, or from about 2 minutes up to about 10 minutes, or up to about 8 minutes, or up to about 6 minutes.

Embodiment 13: The method of embodiment 12, wherein said continues stimulation periods are about 4 minutes in duration.

Embodiment 14: The method according to any one of embodiments 10-13, wherein a delay between continuous stimulation periods ranges from about 5 sec, or from about 10 sec, or from about 15 sec, or from about 20 sec up to about 5 minutes, or up to about 4 minutes, or up to about 3 minutes, or up to about 2 minutes, or up to about 1 min, or up to about 45 sec, or up to about 30 sec.

Embodiment 15: The method of embodiment 14, wherein a delay between continuous stimulation periods is about 30 sec.

Embodiment 16: The method according to any one of embodiments 10-15, wherein said treatment is repeated.

Embodiment 17: The method of embodiment 16, wherein said treatment is repeated daily, or every 2 days, or every 3 days, or every 4 days, or every 5 days, or every 6 days, or every 7 days, or every 8 days, or every 9 days, or every 10 days, or every 11 days, or every 12 days, or every 13 days, or every 14 days.

Embodiment 18: The method according to any one of embodiments 16-17, wherein the treatment is repeated over a period of at least 1 week, or at least two weeks, or at least 3 weeks, or at least 4 weeks, or at least 5 weeks, or at least 6 weeks, or at least 7 weeks, or at least 8 weeks, or at least 9 weeks, or at least 10 weeks, or at least 11 weeks, or at least 12 weeks, or at least 4 months, or at least 5 months, or at least 6 months, or at least 7 months, or at least 8 months, or at least 9 months, or at least 10 months, or at least 11 months, or at least 12 months.

Embodiment 19: The method according to any one of embodiments 1-18, wherein treatment of said subject with said magnetic stimulation facilitates volitional voiding at a later time without magnetic stimulation.

Embodiment 20: The method according to any one of embodiments 16-19, wherein said treatment is repeated daily, or every 2 days, or every 3 days, or every 4 days, or every 5 days, or every 6 days, or every 7 days, or every 8 days, or every 9 days, or every 10 days, or every 11 days, or every 12 days, or every 13 days, or every 14 days until the subject obtains volitional control of micturation.

Embodiment 21: The method of embodiment 20, wherein said treatment is repeated daily, or every 2 days, or every 3 days, or every 4 days, or every 5 days, or every 6 days, or every 7 days, or every 8 days, or every 9 days, or every 10 days, or every 11 days, or every 12 days, or every 13 days, or every 14 days until the subject obtains their maximal volitional control of micturation.

Embodiment 22: The method of embodiment 20, wherein the frequency of treatment is reduced after the subject obtains volitional control of micturition.

Embodiment 23: The method of embodiment 21, wherein the frequency of treatment is reduced after the subject obtains maximal volitional control of micturition.

Embodiment 24: The method according to any one of embodiments 22-23, wherein the frequency of treatment is reduced to a level sufficient to maintain volitional control of micturition.

Embodiment 25: The method of embodiment 24, wherein the frequency of treatment is reduced to every three days, or to a weekly treatment, or to about every 10 days, or to about every 2 weeks.

Embodiment 26: The method according to any one of embodiments 1-25, wherein said magnetic stimulation is applied over the thoracic and/or lumbosacral spinal cord.

Embodiment 27: The method of embodiment 26, wherein said magnetic stimulation is applied over one or more regions selected from the group consisting of T1-T1, T1-T2, T1-T3, T1-T4, T1-T5, T1-T6, T1-T7, T1-T8, T1-T9, T1-T10, T1-T11, T1-T12, T2-T2, T2-T3, T2-T4, T2-T5, T2-T6, T2-T7, T2-T8, T2-T9, T2-T10, T2-T11, T2-T12, T3-T3, T3-T4, T3-T5, T3-T6, T3-T7, T3-T8, T3-T9, T3-T10, T3-T11, T3-T12, T4-T4, T4-T5, T4-T6, T4-T7, T4-T8, T4-T9, T4-T10, T4-T11, T4-T12, T5-T5, T5-T6, T5-T7, T5-T8, T5-T9, T5-T10, T5-T11, T5-T12, T6-T6, T6-T7, T6-T8, T6-T9, T6-T10, T6-T11, T6-T12, T7-T7, T7-T8, T7-T9, T7-T10, T7-T11, T7-T12, T8-T8, T8-T9, T8-T10, T8-T11, T8-T12, T9-T9, T9-T10, T9-T11, T9-T12, T10-T10, T10-T11, T10-T12, T11-T11, T11-T12, T12-T12, L1-L1, L1-L2, L1-L3, L1-L4, L1-L5, L1-S1, L1-S2, L1-S3, L1-S4, L1-55, L2-L2, L2-L3, L2-L4, L2-L5, L2-S1, L2-S2, L2-S3, L2-S4, L2-S5, L3-L3, L3-L4, L3-L5, L3-S1, L3-S2, L3-S3, L3-S4, L3-S5, L4-L4, L4-L5, L4-S1, L4-S2, L4-S3, L4-S4, L4-S5, L5-L5, L5-S1, L5-S2, L5-S3, L5-S4, L5-55, S1-S1, S1-S2, S1-S3, S1-S4, S1-S5, S2-S2, S2-S3, S2-S4, S2-S5, S3-S3, S3-S4, S3-S5, S4-S4, S4-S5, and S5-S6.

Embodiment 28: The method of embodiment 26, wherein said magnetic stimulation is applied over a region between T11 and L4.

Embodiment 29: The method of embodiment 28, wherein said magnetic stimulation is applied over one or more regions selected from the group consisting of T11-T12, L1-L2, and L2-L3.

Embodiment 30: The method of embodiment 28, wherein said magnetic stimulation is applied over L1-L2 and/or over T11-T12.

Embodiment 31: The method of embodiment 28, wherein said magnetic stimulation is applied over L1.

Embodiment 32: The method according to any one of embodiments 1-31, wherein said magnetic stimulation is applied at the midline of spinal cord.

Embodiment 33: The method according to any one of embodiments 1-32, wherein said magnetic stimulation produces a magnetic field of at least about 1 tesla, or at least about 2 tesla, or at least about 3 tesla, or at least about 4 tesla, or at least about 5 tesla.

Embodiment 34: The method according to any one of embodiments 1-2, or 10-33, wherein said magnetic stimulation is at a frequency of at least about 0.5 Hz, 1 Hz, or at least about 2 Hz, or at least about 3 Hz, or at least about 4 Hz, or at least about 5 Hz, or at least about 10 Hz, or at least about 20 Hz or at least about 30 Hz or at least about 40 Hz or at least about 50 Hz or at least about 60 Hz or at least about 70 Hz or at least about 80 Hz or at least about 90 Hz or at least about 100 Hz, or at least about 200 Hz, or at least about 300 Hz, or at least about 400 Hz, or at least about 500 Hz.

Embodiment 35: A method of facilitating voiding or control of bladder and/or bowel in a subject with a neuromotor disorder, said method comprising: providing transcutaneous electrical stimulation of the spinal cord at a location, frequency and intensity sufficient to facilitate voiding or control of bladder and/or bowel.

Embodiment 36: The method of embodiment 35, wherein said method comprises facilitating voiding or control of bladder by providing transcutaneous electrical stimulation of the spinal cord at a location, frequency and intensity sufficient to facilitate voiding or control of the bladder.

Embodiment 37: The method according to any one of embodiments 35-36, wherein said transcutaneous electrical stimulation comprises stimulation at a frequency of at least about 1 Hz, or at least about 2 Hz, or at least about 3 Hz, or at least about 4 Hz, or at least about 5 Hz, or at least about 10 Hz, or at least about 20 Hz or at least about 30 Hz or at least about 40 Hz or at least about 50 Hz or at least about 60 Hz or at least about 70 Hz or at least about 80 Hz or at least about 90 Hz or at least about 100 Hz, or at least about 200 Hz, or at least about 300 Hz, or at least about 400 Hz, or at least about 500 Hz, and/or at a frequency ranging from about 1 Hz, or from about 2 Hz, or from about 3 Hz, or from about 4 Hz, or from about 5 Hz, or from about 10 Hz, or from about 10 Hz, or from about 10 Hz, up to about 500 Hz, or up to about 400 Hz, or up to about 300 Hz, or up to about 200 Hz up to about 100 Hz, or up to about 90 Hz, or up to about 80 Hz, or up to about 60 Hz, or up to about 40 Hz, or from about 3 Hz or from about 5 Hz up to about 80 Hz, or from about 5 Hz to about 60 Hz, or up to about 30 Hz. In certain embodiments the transcutaneous stimulation is at a frequency ranging from about 20 Hz or about 30 Hz to about 90 Hz or to about 100 Hz.

Embodiment 38: The method according to any one of embodiments 35-37, wherein the transcutaneous electrical stimulation is provided on a high frequency carrier signal.

Embodiment 39: The method of embodiment 38, wherein the high frequency carrier signal ranges from about 3 kHz, or about 5 kHz, or about 8 kHz up to about 30 kHz, or up to about 20 kHz, or up to about 15 kHz.

Embodiment 40: The method according to any one of embodiments 38-39, wherein the carrier frequency amplitude ranges from about 30 mA, or about 40 mA, or about 50 mA, or about 60 mA, or about 70 mA, or about 80 mA up to about 300 mA, or up to about 200 mA, or up to about 150 mA.

Embodiment 41: The method according to any one of embodiments 38-40, wherein the transcutaneous electrical stimulation comprises a 10 kHz stimulus repeated at 1-40 times per second.

Embodiment 42: The method according to any one of embodiments 38-41, wherein said transcutaneous electrical stimulus is applied for 1 to 30 s, or for about 5 to 30 s, or for about 10 to about 30 s.

Embodiment 43: The method according to any one of embodiments 38—wherein said transcutaneous electrical stimulus is about 30 to about 100 mA.

Embodiment 44: The method according to any one of embodiments 38-, wherein said transcutaneous electrical stimulus is a high frequency stimulus at a duration ranging from about 0.1 up to about 2 ms, or from about 0.1 up to about 1 ms, or from about 0.5 ms up to about 1 ms, or for about 0.5 ms.

Embodiment 45: The method according to any one of embodiments 38-44, wherein said transcutaneous electrical stimulus comprises a constant-current bipolar rectangular stimulus.

Embodiment 46: The method according to any one of embodiments 38-45, wherein said transcutaneous electrical stimulus comprises a 10 kHz signal applied at 1 Hz.

Embodiment 47: The method according to any one of embodiments 35-46, wherein said transcutaneous electrical stimulation comprises pulses ranging in duration from about 5 μs, or from about 10 μs, or from about 15 μs, or from about 20 μs up to about 2 ms, or up to about 1 ms, or up to about 2 ms, or up to about 500 μs, or up to about 400 μs, or up to about 300 μs, or up to about 200 μs, or up to about 100 μs, or up to about 50 μs.

Embodiment 48: The method of embodiment 47, wherein said pulses are about 1 ms in duration.

Embodiment 49: The method according to any one of embodiments 35-48, wherein a single treatment of said transcutaneous electrical stimulation comprises 1, or 2, or 3, or 4, or 5, or 6, or 7, or 8, or 9, or 10 or more continuous stimulation periods.

Embodiment 50: The method of embodiment 49, wherein said treatment is repeated.

Embodiment 51: The method of embodiment 50, wherein said treatment is repeated daily, or every 2 days, or every 3 days, or every 4 days, or every 5 days, or every 6 days, or every 7 days, or every 8 days, or every 9 days, or every 10 days, or every 11 days, or every 12 days, or every 13 days, or every 14 days.

Embodiment 52: The method according to any one of embodiments 50-51, wherein the treatment is repeated over a period of at least 1 week, or at least two weeks, or at least 3 weeks, or at least 4 weeks, or at least 5 weeks, or at least 6 weeks, or at least 7 weeks, or at least 8 weeks, or at least 9 weeks, or at least 10 weeks, or at least 11 weeks, or at least 12 weeks, or at least 4 months, or at least 5 months, or at least 6 months, or at least 7 months, or at least 8 months, or at least 9 months, or at least 10 months, or at least 11 months, or at least 12 months.

Embodiment 53: The method according to any one of embodiments 35-52, wherein treatment of said subject with said transcutaneous electrical stimulation facilitates volitional voiding at a later time without transcutaneous electrical stimulation.

Embodiment 54: The method according to any one of embodiments 50-53, wherein said treatment is repeated daily, or every 2 days, or every 3 days, or every 4 days, or every 5 days, or every 6 days, or every 7 days, or every 8 days, or every 9 days, or every 10 days, or every 11 days, or every 12 days, or every 13 days, or every 14 days until the subject obtains volitional control of micturation.

Embodiment 55: The method of embodiment 54, wherein said treatment is repeated daily, or every 2 days, or every 3 days, or every 4 days, or every 5 days, or every 6 days, or every 7 days, or every 8 days, or every 9 days, or every 10 days, or every 11 days, or every 12 days, or every 13 days, or every 14 days until the subject obtains their maximal volitional control of micturation.

Embodiment 56: The method of embodiment 54, wherein the frequency of treatment is reduced after the subject obtains volitional control of micturition.

Embodiment 57: The method of embodiment 55, wherein the frequency of treatment is reduced after the subject obtains maximal volitional control of micturition.

Embodiment 58: The method according to any one of embodiments 56-57, wherein the frequency of treatment is reduced to a level sufficient to maintain volitional control of micturition.

Embodiment 59: The method according to any one of embodiments 35-58, wherein said transcutaneous electrical stimulation is applied over one or more regions selected from the group consisting of T1-T1, T1-T2, T1-T3, T1-T4, T1-T5, T1-T6, T1-T7, T1-T8, T1-T9, T1-T10, T1-T11, T1-T12, T2-T2, T2-T3, T2-T4, T2-T5, T2-T6, T2-T7, T2-T8, T2-T9, T2-T10, T2-T11, T2-T12, T3-T3, T3-T4, T3-T5, T3-T6, T3-T7, T3-T8, T3-T9, T3-T10, T3-T11, T3-T12, T4-T4, T4-T5, T4-T6, T4-T7, T4-T8, T4-T9, T4-T10, T4-T11, T4-T12, T5-T5, T5-T6, T5-T7, T5-T8, T5-T9, T5-T10, T5-T11, T5-T12, T6-T6, T6-T7, T6-T8, T6-T9, T6-T10, T6-T11, T6-T12, T7-T7, T7-T8, T7-T9, T7-T10, T7-T11, T7-T12, T8-T8, T8-T9, T8-T10, T8-T11, T8-T12, T9-T9, T9-T10, T9-T11, T9-T12, T10-T10, T10-T11, T10-T12, T11-T11, T11-T12, T12-T12, L1-L1, L1-L2, L1-L3, L1-L4, L1-L5, L1-S1, L1-S2, L1-S3, L1-S4, L1-S5, L2-L2, L2-L3, L2-L4, L2-L5, L2-S1, L2-S2, L2-S3, L2-S4, L2-S5, L3-L3, L3-L4, L3-L5, L3-S1, L3-S2, L3-S3, L3-S4, L3-S5, L4-L4, L4-L5, L4-S1, L4-S2, L4-S3, L4-S4, L4-S5, L5-L5, L5-S1, L5-S2, L5-S3, L5-S4, L5-S5, S1-S1, S1-S2, S1-S3, S1-S4, S1-S5, S2-S2, S2-S3, S2-S4, S2-S5, S3-S3, S3-S4, S3-S5, S4-S4, S4-S5, and S5-S6.

Embodiment 60: The method of embodiment 59, wherein said transcutaneous electrical stimulation is applied over a region between T11 and L4.

Embodiment 61: The method of embodiment 60, wherein said transcutaneous electrical stimulation is applied over one or more regions selected from the group consisting of T11-T12, L1-L2, and L2-L3.

Embodiment 62: The method of embodiment 60, wherein said transcutaneous electrical stimulation is applied over L1-L2 and/or over T11-T12.

Embodiment 63: The method of embodiment 60, wherein said transcutaneous electrical stimulation is applied over L1.

Embodiment 64: The method according to any one of embodiments 35-63, wherein said transcutaneous electrical stimulation is applied at the midline of spinal cord.

Embodiment 65: A method of facilitating voiding or control of bladder and/or bowel in a subject with a neuromotor disorder, said method comprising: providing magnetic stimulation in combination with electrical stimulation at one or more locations, frequencies, and intensities sufficient to facilitate voiding or control of bladder and/or bowel.

Embodiment 66: The method of embodiment 65, wherein said method comprises providing magnetic stimulation to said subject using a method according to any one of embodiments 1-34 in combination with electrical stimulation using a method according to any one of embodiments 35-64.

Embodiment 67: The method according to any one of embodiments 65-72, wherein said magnetic stimulation and said electrical stimulation occur simultaneously.

Embodiment 68: The method according to any one of embodiments 65-72, wherein said magnetic stimulation precedes said electrical stimulation.

Embodiment 69: The method according to any one of embodiments 65-72, wherein said magnetic stimulation follows said electrical stimulation.

Embodiment 70: The method according to any one of embodiments 65-69, wherein said combination of magnetic stimulation and electrical stimulation provides a synergistic effect.

Embodiment 71: A method of facilitating locomotor function in a subject with a neuromotor disorder, wherein said method comprises facilitating locomotor function by providing magnetic stimulation of the spinal cord at a location, frequency and intensity sufficient to facilitate locomotor function.

Embodiment 72: The method of embodiment 71, wherein said locomotor function comprises one or more functions selected from the group consisting of standing, stepping, sitting, laying down, stabilizing sitting posture, stabilizing standing posture.

Embodiment 73: The method according to any one of embodiments 71-72, wherein said magnetic stimulation is applied on the skin surface over a region of the spinal cord or spinal ganglion related to sympathetic and parasympathetic system that controls the lower limbs, pelvis, and/or trunk.

Embodiment 74: The method according to any one of embodiments 71-73, wherein said magnetic stimulation is applied over the thoracic and/or lumbosacral spinal cord, or over spinal ganglia related to sympathetic and parasympathetic system.

Embodiment 75: The method according to any one of embodiments 71-73, wherein said magnetic stimulation is applied over one or more regions selected from the group consisting of T1-T1, T1-T2, T1-T3, T1-T4, T1-T5, T1-T6, T1-T7, T1-T8, T1-T9, T1-T10, T1-T11, T1-T12, T2-T2, T2-T3, T2-T4, T2-T5, T2-T6, T2-T7, T2-T8, T2-T9, T2-T10, T2-T11, T2-T12, T3-T3, T3-T4, T3-T5, T3-T6, T3-T7, T3-T8, T3-T9, T3-T10, T3-T11, T3-T12, T4-T4, T4-T5, T4-T6, T4-T7, T4-T8, T4-T9, T4-T10, T4-T11, T4-T12, T5-T5, T5-T6, T5-T7, T5-T8, T5-T9, T5-T10, T5-T11, T5-T12, T6-T6, T6-T7, T6-T8, T6-T9, T6-T10, T6-T11, T6-T12, T7-T7, T7-T8, T7-T9, T7-T10, T7-T11, T7-T12, T8-T8, T8-T9, T8-T10, T8-T11, T8-T12, T9-T9, T9-T10, T9-T11, T9-T12, T10-T10, T10-T11, T10-T12, T11-T11, T11-T12, T12-T12, L1-L1, L1-L2, L1-L3, L1-L4, L1-L5, L1-S1, L1-S2, L1-S3, L1-S4, L1-55, L2-L2, L2-L3, L2-L4, L2-L5, L2-S1, L2-S2, L2-S3, L2-S4, L2-S5, L3-L3, L3-L4, L3-L5, L3-S1, L3-S2, L3-S3, L3-S4, L3-S5, L4-L4, L4-L5, L4-S1, L4-S2, L4-S3, L4-S4, L4-S5, L5-L5, L5-S1, L5-S2, L5-S3, L5-S4, L5-S5, S1-S1, S1-S2, S1-S3, S1-S4, S1-S5, S2-S2, S2-S3, S2-S4, S2-S5, S3-S3, S3-S4, S3-S5, S4-S4, S4-S5, and S5-S6.

Embodiment 76: The method according to any one of embodiments 71-75, wherein said method includes subjecting said subject to physical training that exposes said subject to relevant postural and locomotor or motor proprioceptive signals.

Embodiment 77: The method of embodiment 76, wherein the wherein the combination of said stimulation and physical training modulates in real time the electrophysiological properties of spinal circuits in said subject so they are activated by proprioceptive information derived from the region of the subject where in the region of the subject involved with one or more of standing, stepping, sitting, laying down, stabilizing sitting posture, and stabilizing standing posture.

Embodiment 78: The method according to any one of embodiments 76-77, wherein said physical training includes inducing a load bearing positional change.

Embodiment 79: The method of embodiment 78, wherein the load bearing positional change in said subject includes one or more of standing, stepping laying down, and sitting.

Embodiment 80: The method of embodiment 71, wherein said locomotor function comprises reaching and/or grasping and/or an increase in arm or grip strength and/or positional control of the arm and/or hand.

Embodiment 81: The method of embodiment 80, wherein said magnetic stimulation is applied on the skin surface over a region of the spinal cord that controls the upper limbs or hand.

Embodiment 82: The method according to any one of embodiments 80-81, wherein said magnetic stimulation is applied over the brain stem and/or cervical spinal cord.

Embodiment 83: The method according to any one of embodiments 80-81, wherein said magnetic stimulation is applied over one or more regions selected from the group consisting of C1-C1, C1-C2, C1-C3, C1-C4, C1-C7, C1-C6, C1-C7, C1-T1, C2-C2, C2-C3, C2-C4, C2-05, C2-C6, C2-C7, C2-T1, C3-C3, C3-C4, C3-05, C3-C6, C3-C7, C3-T1, C4-C4, C4-C5, C4-C6, C4-C7, C4-T1, C5-05, C5-C6, C5-C7, C5-T1, C6-C6, C6-C7, C6-T1, C7-C7, and C7-T1.

Embodiment 84: The method according to any one of embodiments 80-83, wherein said method includes subjecting said subject to physical training that exposes said subject to relevant postural and locomotor or motor proprioceptive signals.

Embodiment 85: The method of embodiment 84, wherein the combination of said stimulation and physical training modulates in real time the electrophysiological properties of spinal circuits in said subject so they are activated by proprioceptive information derived from the upper limbs and/or hand.

Embodiment 86: The method according to any one of embodiments 84-85, wherein said physical training includes hand contraction and/or upper limb movements against a resistance.

Embodiment 87: The method according to any one of embodiments 84-85, wherein said physical training includes inducing a load bearing positional change in the arm and/or hand.

Embodiment 88: The method of embodiment 87, wherein the load bearing positional change in said subject includes reaching and/or grasping.

Embodiment 89: The method according to any one of embodiments 84-85, wherein said physical training includes tracing a displayed pattern by hand manipulation of a hand controller.

Embodiment 90: The method according to any one of embodiments 76-79 or 84-89, wherein said physical training includes robotically guided training.

Embodiment 91: The method according to any one of embodiments 71-90, wherein said magnetic stimulation produces a magnetic field of at least 1 tesla, or at least 2 tesla, or at least 3 tesla, or at least 4 tesla.

Embodiment 92: The method according to any one of embodiments 71-91, wherein said magnetic stimulation is at a frequency of at least about 1 Hz, or at least about 2 Hz, or at least about 3 Hz, or at least about 4 Hz, or at least about 5 Hz, or at least about 10 Hz, or at least about 20 Hz or at least about 30 Hz or at least about 40 Hz or at least about 50 Hz or at least about 60 Hz or at least about 70 Hz or at least about 80 Hz or at least about 90 Hz or at least about 100 Hz, or at least about 200 Hz, or at least about 300 Hz, or at least about 400 Hz, or at least about 500 Hz.

Embodiment 93: The method according to any one of embodiments 71-91, wherein said magnetic stimulation is at a frequency ranging from about 1 Hz, or from about 2 Hz, or from about 3 Hz, or from about 4 Hz, or from about 5 Hz, or from about 10 Hz, or from about 10 Hz, or from about 10 Hz, up to about 500 Hz, or up to about 400 Hz, or up to about 300 Hz, or up to about 200 Hz up to about 100 Hz, or up to about 90 Hz, or up to about 80 Hz, or up to about 60 Hz, or up to about 40 Hz, or from about 3 Hz or from about 5 Hz up to about 80 Hz, or from about 5 Hz to about 60 Hz, or up to about 30 Hz.

Embodiment 94: The method according to any one of embodiments 71-91, wherein said magnetic stimulation is at a frequency ranging from about 20 Hz or about 30 Hz to about 90 Hz or to about 100 Hz.

Embodiment 95: The method according to any one of embodiments 1-94, wherein said magnetic stimulation is applied using a single coil stimulator.

Embodiment 96: The method according to any one of embodiments 1-94, wherein said magnetic stimulation is applied using a double coil stimulator.

Embodiment 97: The method according to any one of embodiments 1-96, wherein the stimulation applied by the subject.

Embodiment 98: The method according to any one of embodiments 1-96, wherein the stimulation is applied by medical care personnel.

Embodiment 99: The method according to any one of embodiments 1-98, wherein said subject is administered at least one monoaminergic agonist.

Embodiment 100: The method of embodiment 99, wherein said at least one monoaminergic agonist comprises an agent selected from the group consisting of a serotonergic drug, a dopaminergic drug, a noradrenergic drug, a GABAergic drug, and a glycinergic drug.

Embodiment 101: The method of embodiment 100, wherein said agent is selected from the group consisting of 8-hydroxy-2-(di-n-propylamino)tetralin (8-OH-DPAT), 4-(benzodioxan-5-yl)1-(indan-2-yl)piperazine (S15535), N-{2-[4-(2-methoxyphenyl)-1-piperazinyl]ethyl}-N-(2-pyridinyl)cyclo-hexanecarboxamide (WAY 100.635), Quipazine, Ketanserin, 4-amino-(6-chloro-2-pyridyl)-1 piperidine hydrochloride (SR 57227A), Ondanesetron, Buspirone, Methoxamine, Prazosin, Clonidine, Yohimbine, 6-chloro-1-phenyl-2,3,4,5-tetrahydro-1H-3-benzazepine-7,8-diol (SKF-81297), 7-chloro-3-methyl-1-phenyl-1,2,4,5-tetrahydro-3-benzazepin-8-ol (SCH-23390), Quinpirole, and Eticlopride.

Embodiment 102: The method of embodiment 100, wherein said monoaminergic agonist is buspirone.

Embodiment 103: The method according to any one of embodiments 1-102, wherein said subject is a non-human mammal.

Embodiment 104: The method according to any one of embodiments 1-102, wherein said subject is a human.

Embodiment 105: The method according to any one of embodiments 1-104, wherein said subject has a spinal cord injury.

Embodiment 106: The method of embodiment 105, wherein said spinal cord injury is clinically classified as motor complete.

Embodiment 107: The method of embodiment 105, wherein said spinal cord injury is clinically classified as motor incomplete.

Embodiment 108: The method according to any one of embodiments 1-103, wherein said subject has an ischemic brain injury.

Embodiment 109: The method of embodiment 108, wherein said ischemic brain injury is brain injury from stroke or acute trauma.

Embodiment 110: The method according to any one of embodiments 1-103, wherein said subject has a neurodegenerative pathology.

Embodiment 111: The method of embodiment 110, wherein said neurodegenerative pathology is associated with a condition selected from the group consisting of stroke, Parkinson's disease, Huntington's disease, Alzheimer's disease, amyotrophic lateral sclerosis (ALS), primary lateral sclerosis (PLS), dystonia, and cerebral palsy.

Embodiment 112: A magnetic stimulator configured to facilitating locomotor function and/or voiding or control of bladder and/or bowel in a subject with a neuromotor disorder, wherein said magnetic stimulator disposed over a region of the spinal cord, provides magnetic stimulation of the spinal cord at a frequency and intensity sufficient to facilitate locomotor function and/or voiding or control of bladder and/or bowel.

Embodiment 113: The magnetic stimulator embodiment 112, wherein said stimulator is configured to provide magnetic stimulation of the spinal cord at a location, frequency and intensity sufficient to facilitate locomotor function.

Embodiment 114: The magnetic stimulator of embodiment 113, wherein said locomotor function comprises one or more functions selected from the group consisting of standing, stepping, sitting, laying down, stabilizing sitting posture, stabilizing standing posture.

Embodiment 115: The magnetic stimulator according to any one of embodiments 113-114, wherein stimulator is configured to apply magnetic stimulation on the skin surface over a region of the spinal cord that controls the lower limbs, pelvis, and/or trunk.

Embodiment 116: The magnetic stimulator according to any one of embodiments 113-115, wherein said magnetic stimulator is configured to provide stimulation over the thoracic and/or lumbosacral spinal cord.

Embodiment 117: The magnetic stimulator according to any one of embodiments 113-115, wherein said magnetic stimulator is configured to apply stimulation over one or more regions selected from the group consisting of T1-T1, T1-T2, T1-T3, T1-T4, T1-T5, T1-T6, T1-T7, T1-T8, T1-T9, T1-T10, T1-T11, T1-T12, T2-T2, T2-T3, T2-T4, T2-T5, T2-T6, T2-T7, T2-T8, T2-T9, T2-T10, T2-T11, T2-T12, T3-T3, T3-T4, T3-T5, T3-T6, T3-T7, T3-T8, T3-T9, T3-T10, T3-T11, T3-T12, T4-T4, T4-T5, T4-T6, T4-T7, T4-T8, T4-T9, T4-T10, T4-T11, T4-T12, T5-T5, T5-T6, T5-T7, T5-T8, T5-T9, T5-T10, T5-T11, T5-T12, T6-T6, T6-T7, T6-T8, T6-T9, T6-T10, T6-T11, T6-T12, T7-T7, T7-T8, T7-T9, T7-T10, T7-T11, T7-T12, T8-T8, T8-T9, T8-T10, T8-T11, T8-T12, T9-T9, T9-T10, T9-T11, T9-T12, T10-T10, T10-T11, T10-T12, T11-T11, T11-T12, T12-T12, L1-L1, L1-L2, L1-L3, L1-L4, L1-L5, L1-S1, L1-S2, L1-S3, L1-S4, L1-55, L2-L2, L2-L3, L2-L4, L2-L5, L2-S1, L2-S2, L2-S3, L2-S4, L2-S5, L3-L3, L3-L4, L3-L5, L3-S1, L3-S2, L3-S3, L3-S4, L3-S5, L4-L4, L4-L5, L4-S1, L4-S2, L4-S3, L4-S4, L4-S5, L5-L5, L5-S1, L5-S2, L5-S3, L5-S4, L5-55, S1-S1, S1-S2, S1-S3, S1-S4, S1-S5, S2-S2, S2-S3, S2-S4, S2-S5, S3-S3, S3-S4, S3-S5, S4-S4, S4-S5, and S5-S6.

Embodiment 118: The magnetic stimulator embodiment 112, wherein said stimulator is configured to provide magnetic stimulation on the skin surface over a region of the spinal cord that controls the upper limbs or hand.

Embodiment 119: The magnetic stimulator according to any one of embodiments 112-118, wherein said magnetic stimulator is configured to apply magnetic stimulation over the brain stem and/or cervical spinal cord.

Embodiment 120: The magnetic stimulator according to any one of embodiments 112-118, wherein said magnetic stimulator is configured to apply magnetic stimulation over one or more regions selected from the group consisting of C1-C1, C1-C2, C1-C3, C1-C4, C1-C7, C1-C6, C1-C7, C1-T1, C2-C2, C2-C3, C2-C4, C2-C5, C2-C6, C2-C7, C2-T1, C3-C3, C3-C4, C3-05, C3-C6, C3-C7, C3-T1, C4-C4, C4-C5, C4-C6, C4-C7, C4-T1, C5-05, C5-C6, C5-C7, C5-T1, C6-C6, C6-C7, C6-T1, C7-C7, and C7-T1.

Embodiment 121: The magnetic stimulator of embodiment 112, wherein said magnetic stimulator is configured to facilitate voiding of bladder and/or bowel by providing magnetic stimulation of the spinal cord at a location, frequency and intensity sufficient to facilitate voiding of bladder and/or bowel.

Embodiment 122: The magnetic stimulator of embodiment 121, wherein said magnetic stimulator is configured to provide magnetic stimulation over the thoracic and/or lumbosacral spinal cord.

Embodiment 123: The magnetic stimulator of embodiment 121, wherein said magnetic stimulator is configured to provide magnetic stimulation over one or more regions selected from the group consisting of T1-T1, T1-T2, T1-T3, T1-T4, T1-T5, T1-T6, T1-T7, T1-T8, T1-T9, T1-T10, T1-T11, T1-T12, T2-T2, T2-T3, T2-T4, T2-T5, T2-T6, T2-T7, T2-T8, T2-T9, T2-T10, T2-T11, T2-T12, T3-T3, T3-T4, T3-T5, T3-T6, T3-T7, T3-T8, T3-T9, T3-T10, T3-T11, T3-T12, T4-T4, T4-T5, T4-T6, T4-T7, T4-T8, T4-T9, T4-T10, T4-T11, T4-T12, T5-T5, T5-T6, T5-T7, T5-T8, T5-T9, T5-T10, T5-T11, T5-T12, T6-T6, T6-T7, T6-T8, T6-T9, T6-T10, T6-T11, T6-T12, T7-T7, T7-T8, T7-T9, T7-T10, T7-T11, T7-T12, T8-T8, T8-T9, T8-T10, T8-T11, T8-T12, T9-T9, T9-T10, T9-T11, T9-T12, T10-T10, T10-T11, T10-T12, T11-T11, T11-T12, T12-T12, L1-L1, L1-L2, L1-L3, L1-L4, L1-L5, L1-S1, L1-S2, L1-S3, L1-S4, L1-S5, L2-L2, L2-L3, L2-L4, L2-L5, L2-S1, L2-S2, L2-S3, L2-S4, L2-S5, L3-L3, L3-L4, L3-L5, L3-S1, L3-S2, L3-S3, L3-S4, L3-S5, L4-L4, L4-L5, L4-S1, L4-S2, L4-S3, L4-S4, L4-S5, L5-L5, L5-S1, L5-S2, L5-S3, L5-S4, L5-S5, S1-S1, S1-S2, S1-S3, S1-S4, S1-S5, S2-S2, S2-S3, S2-S4, S2-S5, S3-S3, S3-S4, S3-S5, S4-S4, S4-S5, and S5-S6.

Embodiment 124: The magnetic stimulator of embodiment 121, wherein said magnetic stimulator is configured to provide magnetic stimulation over one or more regions selected from the group consisting of T11-T12, L1-L2, and L2-L3.

Embodiment 125: The magnetic stimulator of embodiment 121, wherein said magnetic stimulator is configured to provide magnetic stimulation over L1-L2 and/or over T11-T12.

Embodiment 126: The magnetic stimulator according to any one of embodiments 112-125, wherein said magnetic stimulator is configured to produce a magnetic field of at least 1 tesla, or at least 2 tesla, or at least 3 tesla, or at least 4 tesla.

Embodiment 127: The magnetic stimulator according to any one of embodiments 112-126, wherein said magnetic stimulator is configured to produce a stimulation at a frequency of at least about 1 Hz, or at least about 2 Hz, or at least about 3 Hz, or at least about 4 Hz, or at least about 5 Hz, or at least about 10 Hz, or at least about 20 Hz or at least about 30 Hz or at least about 40 Hz or at least about 50 Hz or at least about 60 Hz or at least about 70 Hz or at least about 80 Hz or at least about 90 Hz or at least about 100 Hz, or at least about 200 Hz, or at least about 300 Hz, or at least about 400 Hz, or at least about 500 Hz.

Embodiment 128: The magnetic stimulator according to any one of embodiments 112-126, wherein said magnetic stimulator is configured to produce a stimulation at a frequency ranging from about 1 Hz, or from about 2 Hz, or from about 3 Hz, or from about 4 Hz, or from about 5 Hz, or from about 10 Hz, or from about 10 Hz, or from about 10 Hz, up to about 500 Hz, or up to about 400 Hz, or up to about 300 Hz, or up to about 200 Hz up to about 100 Hz, or up to about 90 Hz, or up to about 80 Hz, or up to about 60 Hz, or up to about 40 Hz, or from about 3 Hz or from about 5 Hz up to about 80 Hz, or from about 5 Hz to about 60 Hz, or up to about 30 Hz.

Embodiment 129: The magnetic stimulator according to any one of embodiments 112-126, wherein said magnetic stimulator is configured to produce a stimulation at a frequency ranging from about 20 Hz or about 30 Hz to about 90 Hz or to about 100 Hz.

Embodiment 130: The magnetic stimulator according to any one of embodiments 112-129, wherein said magnetic comprises a single stimulation coil.

Embodiment 131: The magnetic stimulator according to any one of embodiments 112-129, wherein said magnetic stimulator comprises a double stimulation coil.

Embodiment 132: The magnetic stimulator according to any one of embodiments 112-131, wherein the stimulator is configured for application of the stimulation by the subject.

Embodiment 133: The magnetic stimulator according to any one of embodiments 112-131, wherein the stimulator is configured for application of the stimulation by medical care personnel.

Embodiment 134: A magnetic stimulator according to any one of embodiments 112-133, for use in facilitating locomotor function and/or voiding of bladder and/or bowel in a subject with a neuromotor disorder, by providing magnetic stimulation of the spinal cord at a location, frequency and intensity sufficient to facilitate locomotor function and/or voiding of bladder and/or bowel.

Definitions

As used herein "electrical stimulation" or "stimulation" means application of an electrical signal that may be either excitatory or inhibitory to a muscle or neuron and/or to groups of neurons and/or interneurons. It will be understood that an electrical signal may be applied to one or more electrodes with one or more return electrodes.

As used herein "magnetic stimulation" refers to use of a varying magnetic field to induce an electrical signal, e.g., in a neuron, that may be either excitatory or inhibitory to a muscle or neuron and/or to groups of neurons and/or interneurons.

As used herein "epidural" means situated upon the dura or in very close proximity to the dura. The term "epidural stimulation" refers to electrical epidural stimulation. In certain embodiments epidural stimulation is referred to as "electrical enabling motor control" (eEmc).

The term "transcutaneous stimulation" or "transcutaneous electrical stimulation" or "cutaneous electrical stimulation" refers to electrical stimulation applied to the skin, and, as typically used herein refers to electrical stimulation applied to the skin in order to effect stimulation of the spinal cord or a region thereof. The term "transcutaneous electrical spinal cord stimulation" may also be referred to as "tSCS". The term "pcEmc" refers to painless cutaneous electrical stimulation.

The term "motor complete" when used with respect to a spinal cord injury indicates that there is no motor function below the lesion, (e.g., no movement can be voluntarily induced in muscles innervated by spinal segments below the spinal lesion.

The term "monopolar stimulation" refers to stimulation between a local electrode and a common distant return electrode.

The term "co-administering", "concurrent administration", "administering in conjunction with" or "administering in combination" when used, for example with respect to transcutaneous electrical stimulation, epidural electrical stimulation, and pharmaceutical administration, refers to administration of the transcutaneous electrical stimulation and/or epidural electrical stimulation and/or pharmaceutical such that various modalities can simultaneously achieve a physiological effect on the subject. The administered modalities need not be administered together, either temporally or at the same site. In some embodiments, the various "treatment" modalities are administered at different times. In some embodiments, administration of one can precede administration of the other (e.g., drug before electrical and/or magnetic stimulation or vice versa). Simultaneous physiological effect need not necessarily require presence of drug and the electrical and/or magnetic stimulation at the same time or the presence of both stimulation modalities at the same time. In some embodiments, all the modalities are administered essentially simultaneously.

The phrase "spinal cord stimulation" as used herein includes stimulation of any spinal nervous tissue, including spinal neurons, accessory neuronal cells, nerves, nerve roots, nerve fibers, or tissues, that are associated with the spinal cord. It is contemplated that spinal cord stimulation may comprise stimulation of one or more areas associated with a cervical vertebral segment.

As used herein, "spinal nervous tissue" refers to nerves, neurons, neuroglial cells, glial cells, neuronal accessory cells, nerve roots, nerve fibers, nerve rootlets, parts of nerves, nerve bundles, mixed nerves, sensory fibers, motor fibers, dorsal root, ventral root, dorsal root ganglion, spinal ganglion, ventral motor root, general somatic afferent fibers, general visceral afferent fibers, general somatic efferent fibers, general visceral efferent fibers, grey matter, white matter, the dorsal column, the lateral column, and/or the ventral column associated with the spinal cord. Spinal nervous tissue includes "spinal nerve roots," that comprise any one or more of the 31 pairs of nerves that emerge from the spinal cord. Spinal nerve roots may be cervical nerve roots, thoracic nerve roots, and lumbar nerve roots.

DETAILED DESCRIPTION

Figure 1:
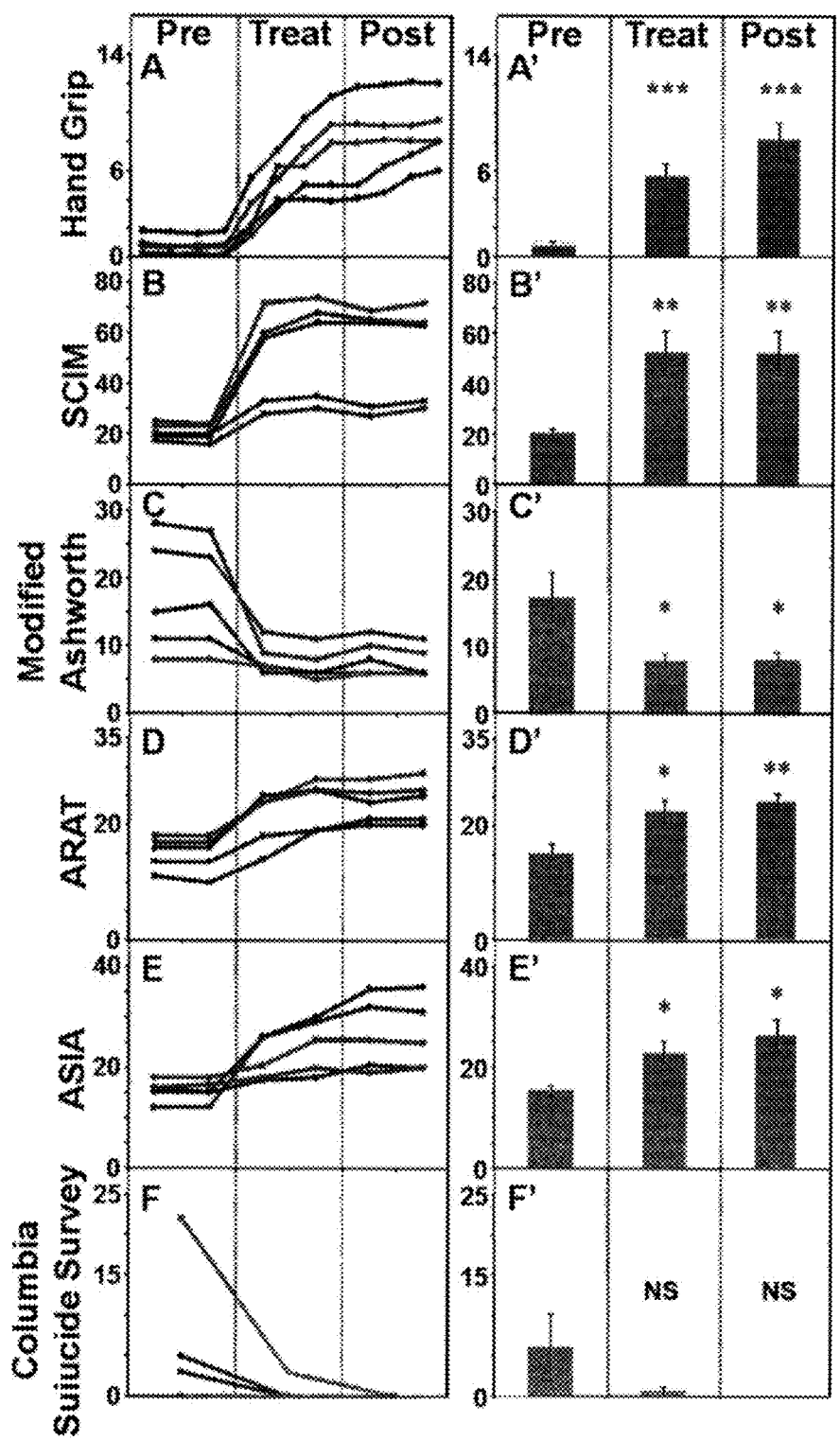
FIG. 1, panels A-F, illustrates magnetic neuromodulation of the cervical spinal cord in spinal cord injury (SCI). Five subjects with stable SCI (>1 year) were evaluated with a battery of tests once a week for 3 months to establish a pre-treatment baseline, with the last month shown here (Pre). Subjects were then treated weekly with electromagnetic spinal cord stimulation (EMSS) and tested weekly for a month (Treat). Subjects were then tested weekly for a month without treatment to determine the durability of the treatment (Post). Panel A, A': Handgrip. Panels B, B': Spinal Cord Independence Measure (SCIM). Panels C, C': Modified Ashworth. Panels D, D': Arm Reach Action Test (ARAT). Panels E, E': International Standards for Neurological Classification of Spinal Cord Injury (ISNCSCI) upper extremity motor exam of five muscles in each arm on a scale for 0-5 for a 50-point max. Panels F, F': Columbia Suicide Survey. Two Tailed Students T-test with Bonferroni post-hoc correction. * $p<0.05$;  $p<0.01$; * $p<0.001$. Device: MagPro (MagVenture, Atlanta) with Cool-B35 Butterfly Coil and Biphasic stimulation at 30 Hz.

In various embodiments methods and devices are provided to regain bladder control and/or to regain motor function in spinal cord injured subjects. Such subjects include, inter alia, subjects with injury to the central nervous system (including brain stem and/or spinal cord) or degenerative neuromotor conditions (e.g., stroke, TBI, MS, ALS, Parkinson's disease, Alzheimer's disease, and the like).

It was discovered that stimulation with devices that impart a magnetic field (e.g., at a frequency range from about 0.5 Hz up to about 100 Hz) can regulate bladder function. In particular, low frequency magnetic stimulation (e.g., 0.5 Hz up to about 20 Hz) can induce micturition, while higher frequency magnetic stimulation (e.g. 20 Hz or 30 Hz up to about 10 Hz or 100 Hz) can suppress micturition. More surprisingly it was discovered that repeated treatments with magnetic stimulation can over time increase volitional control of bladder function. Once volitional control of bladder function is realized, repeated periodic treatments (e.g., weekly, every 10 days, biweekly, etc.) can maintain this volitional bladder control.

It was also discovered that stimulation with devices that impart an electrical or magnetic field (e.g., at a frequency range from 5-100 Hz) of the cervical, and/or thoracic, and/or lumbar spinal cord, nerve roots, or combinations thereof can restore arm and leg movement (e.g., in subjects with a partial or full spinal cord injury). It was also discovered that, with training and repetition, the gains with stimulation can be hardwired and present even without stimulation. Additionally, it was discovered that serotonin agonists such as buspirone and the like can be used to further activate the spinal network to improve motor function.

Stimulation of the cervical, and/or thoracic, and/or lumbar spinal cord, nerve roots, or combinations thereof can be induced by epidural stimulation electrodes, non-invasive transcutaneous electrical stimulation, or magnetic stimulation.

Additionally, it was discovered that the stimulation methods described herein can be leveraged to regain motor function in subjects with injury to the central nervous system or degenerative neuromotor conditions, including, but not limited to stroke, TBI, MS, ALS, Parkinson's disease, Alzheimer's disease, and the like.

Without being bound to a particular theory, it is believed that enabling the spinal circuitry can produce a coordinated behavior that is more complete and physiologic than stimulation of individual nerve roots or the peripheral nerves. Moreover, the existing devices have the disadvantages of being invasive, producing a subset of the desired locomotor or micturition behavior, and do not result in enduring plastic changes to the circuitry that allow patients to become device independent.

By way of illustration, it is noted that medtronic markets the INTERSTIM® device for sacral neuromodulation with overactive bladder or fecal incontinence. This device can be effective, but there is a fundamental difference in the mechanism of action compared to the methods described herein. Neuromodulation of the sacral nerve roots, as with the Medtronic InterStim, attempts to produce appropriate behavior by altering the activity of the sacral nerves.

In contrast, the methods described herein alter the activity of the spinal circuitry. It is believed that enabling the spinal circuitry produces a coordinated behavior that is more complete and physiologically normative than stimulation of the peripheral nerves. Moreover, the existing devices have the disadvantages of being invasive, producing a subset of the micturition behavior, and do not result in enduring plastic changes to the circuitry that allow patients to become device independent.

Voiding of Bladder and/or Bowel.

As explained above, the orchestrated neuromuscular control of urinary bladder function by the sensory, motor and autonomic nervous systems can be impaired by degenerative or traumatic changes, such as multiple sclerosis, spinal cord injury, stroke. It was discovered that stimulation of the spinal cord and, optionally, associated nerve roots can restore voluntary control of bladder and/or bowel function.

In particular, it was discovered that non-invasive (e.g., magnetic or transcutaneous electrical) stimulation of the cervical, thoracic, lumbar (vertebral body designation) spinal cord and associated nerve roots and combination thereof, results in micturition and/or restoration of bowel function. In particular it was observed that electrical stimulation with (10 kHz constant-current bipolar rectangular stimulus) from a range of 1 Hz to 100 Hz enabled micturition and restoration of bowel function. It was also observed that stimulation with a magnetic stimulator, generating a magnetic field, within a range of 1 Hz to 100 Hz enabled micturition and restoration of bowel function.

Magnetic Stimulation to Restore Bladder/Bowel Function.

More generally, it was discovered that stimulation of the spinal cord with devices that impart a magnetic field (e.g., at a frequency range from about 0.5 Hz up to about 100 Hz) can regulate bladder function. In particular, low frequency magnetic stimulation (e.g., 0.5 Hz up to about 15 Hz) can induce micturition, while higher frequency magnetic stimulation (e.g. 20 Hz or 30 Hz up to about 100 Hz) can suppress micturition. Thus, for example, it was observed that at a low frequency (e.g., 1 Hz) the detrusor pressure increased with minimal or small change in urethral pressure so micturition seemed to be enhanced (which can be used to treat underactive and neurogenic bladder). At high frequency (e.g., 30 Hz) urethral pressure increased with no modification of detrusor pressure so urine can be retained (which can be used to treat overactive bladder or stress incontinence).

More surprisingly it was discovered that repeated treatments with magnetic stimulation can over time increase volitional control of bladder function. Once volitional control of bladder function is realized, repeated periodic treatments (e.g., weekly, every 10 days, biweekly, etc.) can maintain this volitional bladder control.

Accordingly, in various embodiments methods of facilitating voiding or control of bladder and/or bowel in a subject with a neuromotor disorder are provided where the methods involve providing magnetic stimulation of the spinal cord at a location, frequency and intensity sufficient to facilitate voiding or control of bladder and/or bowel. In certain embodiments the magnetic stimulation comprises stimulation at a frequency ranging from about 0.5 Hz up to about 15 Hz to induce micturition and in certain embodiments the magnetic stimulation is at a frequency of about 1 Hz. In certain embodiments the magnetic stimulation comprises stimulation at a frequency from about 20 Hz up to about 100 Hz to stop or prevent micturition and in certain embodiments, the magnetic stimulation is at a frequency of about 30 Hz.

In certain embodiments the magnetic stimulation comprises magnetic pulses ranging in duration from about 5 μs, or from about 10 μs, or from about 15 μs, or from about 20 μs up to about 1 ms, or up to about 750 μs, or up to about 500 μs, or up to about 400 μs, or up to about 300 μs, or up to about 200 μs, or up to about 100 μs. or up to about 50 μs. In certain embodiments the magnetic pulses are about 25 μs in duration.

In certain embodiments the magnetic stimulation is monophasic, while in other embodiments, the magnetic stimulation is biphasic.

In certain embodiments a single treatment of magnetic stimulation comprises 1, or 2, or 3, or 4, or 5, or 6, or 7, or 8, or 9, or 10 or more continuous stimulation periods. In various embodiments the continuous stimulation periods range in duration from about 10 sec, or from about 20 sec, or from about 3 sec or from about 40 sec, or from about 50 sec, or from about 1 min, or from about 2 minutes up to about 10 minutes, or up to about 8 minutes, or up to about 6 minutes. In certain embodiments the continuous stimulation periods are about 4 minutes in duration. In certain embodiments the delay between continuous stimulation periods ranges from about 2 sec, or from about 5 sec, or from about 10 sec, or from about 15 sec, or from about 20 sec up to about 5 minutes, or up to about 4 minutes, or up to about 3 minutes, or up to about 2 minutes, or up to about 1 min, or up to about 45 sec, or up to about 30 sec. In certain embodiments the delay between continuous stimulation periods is about 30 sec.

It was discovered that repeating the treatment can progressively increase subsequent volitional control of bladder function (e.g., permits volitional voiding at a later time without magnetic (or electrical) stimulation). Conversely removal of repetitive treatments can result in progressive loss of volitional control. Accordingly, in certain embodiments the treatment is repeated (e.g., repeated daily, or every 2 days, or every 3 days, or every 4 days, or every 5 days, or every 6 days, or every 7 days, or every 8 days, or every 9 days, or every 10 days, or every 11 days, or every 12 days, or every 13 days, or every 14 days). In certain embodiments the treatment is repeated over a period of at least 1 week, or at least two weeks, or at least 3 weeks, or at least 4 weeks, or at least 5 weeks, or at least 6 weeks, or at least 7 weeks, or at least 8 weeks, or at least 9 weeks, or at least 10 weeks, or at least 11 weeks, or at least 12 weeks, or at least 4 months, or at least 5 months, or at least 6 months, or at least 7 months, or at least 8 months, or at least 9 months, or at least 10 months, or at least 11 months, or at least 12 months. In certain embodiments the treatment is repeated daily, or every 2 days, or every 3 days, or every 4 days, or every 5 days, or every 6 days, or every 7 days, or every 8 days, or every 9 days, or every 10 days, or every 11 days, or every 12 days, or every 13 days, or every 14 days until the subject obtains volitional control of micturation. In certain embodiments the treatment is repeated daily, or every 2 days, or every 3 days, or every 4 days, or every 5 days, or every 6 days, or every 7 days, or every 8 days, or every 9 days, or every 10 days, or every 11 days, or every 12 days, or every 13 days, or every 14 days until the subject obtains their maximal volitional control of micturation.

In certain embodiments, once volitional control is achieved, the frequency of treatment can be reduced to a "maintenance" level. Typically, the frequency of treatment is is reduced to a level sufficient to maintain volitional control (e.g., a desired level of volitional control) of micturition. In certain embodiments the frequency of treatment is reduced to every three days, or to a weekly treatment, or to about every 10 days, or to about every 2 weeks.

In certain embodiments the magnetic stimulation is applied over the thoracic and/or lumbosacral spinal cord (e.g., over one or more regions selected from the group consisting of T1-T1, T1-T2, T1-T3, T1-T4, T1-T5, T1-T6, T1-T7, T1-T8, T1-T9, T1-T10, T1-T11, T1-T12, T2-T2, T2-T3, T2-T4, T2-T5, T2-T6, T2-T7, T2-T8, T2-T9, T2-T10, T2-T11, T2-T12, T3-T3, T3-T4, T3-T5, T3-T6, T3-T7, T3-T8, T3-T9, T3-T10, T3-T11, T3-T12, T4-T4, T4-T5, T4-T6, T4-T7, T4-T8, T4-T9, T4-T10, T4-T11, T4-T12, T5-T5, T5-T6, T5-T7, T5-T8, T5-T9, T5-T10, T5-T11, T5-T12, T6-T6, T6-T7, T6-T8, T6-T9, T6-T10, T6-T11, T6-T12, T7-T7, T7-T8, T7-T9, T7-T10, T7-T11, T7-T12, T8-T8, T8-T9, T8-T10, T8-T11, T8-T12, T9-T9, T9-T10, T9-T11, T9-T12, T10-T10, T10-T11, T10-T12, T11-T11, T11-T12, T12-T12, L1-L1, L1-L2, L1-L3, L1-L4, L1-L5, L1-S1, L1-S2, L1-S3, L1-S4, L1-55, L2-L2, L2-L3, L2-L4, L2-L5, L2-S1, L2-S2, L2-S3, L2-S4, L2-S5, L3-L3, L3-L4, L3-L5, L3-S1, L3-S2, L3-S3, L3-S4, L3-S5, L4-L4, L4-L5, L4-S1, L4-S2, L4-S3, L4-S4, L4-S5, L5-L5, L5-S1, L5-S2, L5-S3, L5-S4, L5-55, S1-S1, S1-S2, S1-S3, S1-S4, S1-S5, S2-S2, S2-S3, S2-S4, S2-S5, S3-S3, S3-S4, S3-S5, S4-S4, S4-S5, and S5-S6). In certain embodiments the magnetic stimulation is applied over a region between T11 and L4. In certain embodiments the magnetic stimulation is applied over one or more regions selected from the group consisting of T11-T12, L1-L2, and L2-L3. In certain embodiments the magnetic stimulation is applied over L1-L2 and/or over T11-T12. In certain embodiments the magnetic stimulation is applied over L1. In certain embodiments the magnetic stimulation is applied at the midline of spinal cord. In various embodiments the magnetic stimulation produces a magnetic field of at least about 0.5 tesla, or at least about 0.6 tesla, or at least about 0.7 tesla, or at least about 0.8 tesla, or at least about 0.9 tesla, or at least about 1 tesla, or at least about 2 tesla, or at least about 3 tesla, or at least about 4 tesla, or at least about 5 tesla. In certain embodiments the magnetic stimulation is at a frequency of at least about 0.5 Hz, 1 Hz, or at least about 2 Hz, or at least about 3 Hz, or at least about 4 Hz, or at least about 5 Hz, or at least about 10 Hz, or at least about 20 Hz or at least about 30 Hz or at least about 40 Hz or at least about 50 Hz or at least about 60 Hz or at least about 70 Hz or at least about 80 Hz or at least about 90 Hz or at least about 100 Hz, or at least about 200 Hz, or at least about 300 Hz, or at least about 400 Hz, or at least about 500 Hz.

Accordingly, in certain embodiments, methods of facilitating voiding of the bladder or bowel are provided where the methods involve providing magnetic stimulation of the spinal cord at a location, frequency and intensity sufficient to facilitate voiding of the bladder and/or bowel. In certain embodiments the spinal cord stimulation facilitates initiation of voiding of the bowel and/or bladder. In certain embodiments the spinal cord stimulation improves the efficacy of voiding of the bladder and/or bowel. In certain embodiments the spinal cord stimulation suppresses micturition. Also, in certain embodiments the magnetic stimulation is of a frequency and magnitude sufficient to restore volitional control of the bladder in the absence of stimulation.

Electrical Stimulation to Restore Bladder/Bowel Function.

Similarly, it was also observed that transcutaneous electrical stimulation can facilitate bladder and/or bowel control (see, e.g. Example 2). Transcutaneous electrical stimulation can readily be applied using an electrical stimulator coupled to electrodes that are applied to the surface of the subjects body (e.g., over the spinal cord at the regions described herein).

Suitable parameters for electrical stimulation and locations of such stimulation are discussed below and illustrated in Example 2.

Facilitation of Locomotor Function.

It was discovered that the following can be leveraged to regain motor function in spinal cord injured subjects which can be broadened to include any subjects with injury to the central nervous system or degenerative neuromotor conditions (stroke, TBI, MS, ALS, Parkinson's disease, Alzheimer's disease, and the like):

1. Stimulation with devices that impart an electrical or magnetic field (frequency range from 5-100 Hz) of the cervical, thoracic, and lumbar spinal cord, nerve roots, or combinations thereof can restore arm and leg movement;

2. With training and repetition, the gains with stimulation can be hardwired and present even without stimulation.

3. Serotonin agonist medication such as buspirone can be used as tool to further activate the spinal network to improve motor function.

In various embodiments stimulation of the above parameters of the various structures can be induced by epidural stimulation electrodes, non-invasive transcutaneous electrical stimulation, or magnetic stimulation, e.g., as described herein. Accordingly, in certain embodiments, methods of facilitating locomotor activity (e.g., standing, stepping, sitting, laying down, stabilizing sitting posture, stabilizing standing posture, arm motion, hand motion, griping, hand strength, and the like) are provided where the methods involve providing magnetic stimulation (or in certain embodiments, transcutaneous electrical or epidural electrical stimulation) of the spinal cord at a location, frequency and intensity sufficient to facilitate the desired locomotor activity. In certain embodiments the spinal cord stimulation facilitates standing, and/or stepping, and/or sitting, and/or postural changes. In certain embodiments the spinal cord stimulation facilitates motion of the arm or hand, gripping action and/or arm and/or hand strength.

Regions of Stimulation.

As noted above, in various embodiments one or more regions of the spinal cord are stimulated to facilitate locomotor function (e.g., standing, stepping, postural changes, arm and/or hand control, etc.), or to facilitate voiding of bowel and/or bladder. Depending on the desired function, in certain embodiments stimulation is applied to, or over, one or more regions of cervical spinal cord, and/or to or over one or more regions of the thoracic spinal cord, and/or to or over or one or more regions of the lumbosacral spinal cord.

For example, in certain embodiments, to facilitate locomotor activity such as standing, stepping, postural control, and the like, the methods may involve stimulating one or more regions of the thoracic and/or lumbosacral spinal cord.

In certain embodiments to facilitate locomotor activity such as control of the hand and/or arm and/or grasping, and the like, the methods may involve stimulating one or more regions of the cervical and/or thoracic spinal cord. Thus, for example, as demonstrated herein cervical spinal cord stimulation improves hand strength and hand and arm locomotor control.

In certain embodiments, to facilitate voiding of the bowel and/or bladder, the methods may involve stimulating one or more regions of the thoracic and/or lumbosacral spinal cord. For example, in certain embodiments, stimulation (e.g., magnetic stimulation) may be applied to or over one or more regions selected from the group consisting of T11-T12, L1-L2, and L2-L3. In certain embodiments stimulation (e.g., magnetic stimulation) may be applied to or over L1-L2 and/or T11-T12.

With respect to application of stimulation to the cervical spinal cord, illustrative regions include, but are not limited to one or more regions straddling or spanning a region selected from the group consisting of C1-C1, C1-C2, C1-C3, C1-C4, C1-C7, C1-C6, C1-C7, C1-T1, C2-C2, C2-C3, C2-C4, C2-05, C2-C6, C2-C7, C2-T1, C3-C3, C3-C4, C3-05, C3-C6, C3-C7, C3-T1, C4-C4, C4-05, C4-C6, C4-C7, C4-T1, C5-C5, C5-C6, C5-C7, C5-T1, C6-C6, C6-C7, C6-T1, C7-C7, and C7-T1.

With respect to application of stimulation to the thoracic spinal cord, illustrative regions include, but are not limited to one or more regions straddling or spanning a region selected from the group consisting of T1-T1, T1-T2, T1-T3, T1-T4, T1-T5, T1-T6, T1-T7, T1-T8, T1-T9, T1-T10, T1-T11, T1-T12, T2-T2, T2-T3, T2-T4, T2-T5, T2-T6, T2-T7, T2-T8, T2-T9, T2-T10, T2-T11, T2-T12, T3-T3, T3-T4, T3-T5, T3-T6, T3-T7, T3-T8, T3-T9, T3-T10, T3-T11, T3-T12, T4-T4, T4-T5, T4-T6, T4-T7, T4-T8, T4-T9, T4-T10, T4-T11, T4-T12, T5-T5, T5-T6, T5-T7, T5-T8, T5-T9, T5-T10, T5-T11, T5-T12, T6-T6, T6-T7, T6-T8, T6-T9, T6-T10, T6-T11, T6-T12, T7-T7, T7-T8, T7-T9, T7-T10, T7-T11, T7-T12, T8-T8, T8-T9, T8-T10, T8-T11, T8-T12, T9-T9, T9-T10, T9-T11, T9-T12, T10-T10, T10-T11, T10-T12, T11-T11, T11-T12, and T12-T12.

With respect to application of stimulation to the lumbosacral spinal cord, illustrative regions include, but are not limited to one or more regions straddling or spanning a region selected from the group consisting of L1-L1, L1-L2, L1-L3, L1-L4, L1-L5, L1-S1, L1-S2, L1-S3, L1-S4, L1-55, L2-L2, L2-L3, L2-L4, L2-L5, L2-S1, L2-S2, L2-S3, L2-S4, L2-S5, L3-L3, L3-L4, L3-L5, L3-S1, L3-S2, L3-S3, L3-S4, L3-S5, L4-L4, L4-L5, L4-S1, L4-S2, L4-S3, L4-S4, L4-S5, L5-L5, L5-S1, L5-S2, L5-S3, L5-S4, L5-55, S1-S1, S1-S2, S1-S3, S1-S4, S1-55, S2-S2, S2-S3, S2-S4, S2-S5, S3-S3, S3-S4, S3-S5, S4-S4, S4-S5, and S5-S6.

Methods of Stimulation.

Magnetic Stimulation.

In certain embodiments the methods described herein utilize magnetic stimulators for stimulation of the spinal cord (e.g., spinal circuits) to facilitate locomotor activity (e.g., standing, stepping, sitting, laying down, stabilizing sitting posture, stabilizing standing posture, arm motion, hand motion, griping, hand strength, and the like) and/or to induce or improve voiding of the bowel and/or bladder. Magnetic spinal cord stimulation is achieved by generating a rapidly changing magnetic field to induce a current at the region(s) of interest. In certain embodiments effective spinal cord stimulation typically utilizes a current transient of about $10^8$ A/s or greater discharged through a stimulating coil. The discharge current flowing through the stimulating coil generates magnetic lines of force. As the lines of force cut through tissue (e.g., the spinal cord or brain stem), a current is generated in that tissue. If the induced current is of sufficient amplitude and duration such that the cell membrane is depolarized, neural/neuromuscular tissue will be stimulated.

Since the magnetic field strength falls off with the square of the distance from the stimulating coil, the stimulus strength is at its highest close to the coil surface. The stimulation characteristics of the magnetic pulse, such as depth of penetration, strength and accuracy, depend on the rise time, peak electrical energy transferred to the coil and the spatial distribution of the field. The rise time and peak coil energy are governed by the electrical characteristics of the magnetic stimulator and stimulating coil, whereas the spatial distribution of the induced electric field depends on the coil geometry and the anatomy of the region of induced current flow.

In various embodiments the magnetic nerve stimulator will produce a field strength up to about 10 tesla, or up to about 8 tesla, or up to about 6 tesla, or up to about 5 tesla, or up to about 4 tesla, or up to about 3 tesla, or up to about 2 tesla, or up to about 1 tesla, or up to about 0.8 tesla, or up to about 0.6 tesla, or up to about 0.5 tesla. In certain embodiments the nerve stimulator produces pulses with a duration from about 5 μs, or from about 10 μs, or from about 15 μs, or from about 20 μs up to about 10 ms, or from about 25 μs up to about 500 μs, or from about 25 μs or to about 100 μs, or from about 100 μs up to about 1 ms.

In certain embodiments the magnetic stimulation is at a frequency of at least about 1 Hz, or at least about 2 Hz, or at least about 3 Hz, or at least about 4 Hz, or at least about 5 Hz, or at least about 10 Hz, or at least about 20 Hz or at least about 30 Hz or at least about 40 Hz or at least about 50 Hz or at least about 60 Hz or at least about 70 Hz or at least about 80 Hz or at least about 90 Hz or at least about 100 Hz, or at least about 200 Hz, or at least about 300 Hz, or at least about 400 Hz, or at least about 500 Hz.

In certain embodiments the magnetic stimulation is at a frequency ranging from about 0.5 Hz, or from about 1 Hz, or from about 2 Hz, or from about 3 Hz, or from about 4 Hz, or from about 5 Hz, or from about 10 Hz, or from about 10 Hz, or from about 10 Hz, up to about 500 Hz, or up to about 400 Hz, or up to about 300 Hz, or up to about 200 Hz up to about 100 Hz, or up to about 90 Hz, or up to about 80 Hz, or up to about 60 Hz, or up to about 40 Hz, or from about 3 Hz or from about 5 Hz up to about 80 Hz, or from about 5 Hz to about 60 Hz, or up to about 30 Hz.

In certain embodiments the magnetic stimulation is at a frequency ranging from about 20 Hz or about 30 Hz to about 90 Hz or to about 100 Hz.

In certain embodiments the magnetic stimulation is at a frequency, pulse width, and amplitude sufficient to initiate and/or improve standing, stepping, sitting, laying down, stabilizing sitting posture, stabilizing standing posture, arm motion, hand motion, stimulate gripping, improve hand strength, and the like, and/or to induce or improve voiding of the bowel and/or bladder. In certain embodiments the stimulation is at a frequency, pulse width, and amplitude sufficient to provide at least 30% emptying or at least 40% emptying, or at least 50% emptying, or at least 60% emptying, or at least 70% emptying, or at least 80% emptying, or at least 90% emptying, or at least 95% emptying, or at least 98% emptying of the bladder and/or bowel e.g., upon application of electrical stimulation as described herein.

Transcutaneous Electrical Stimulation.

In certain embodiments the methods described herein utilize transcutaneous electrical stimulation for stimulation of the spinal cord (e.g., spinal circuits) to facilitate locomotor activity (e.g., standing, stepping, sitting, laying down, stabilizing sitting posture, stabilizing standing posture, arm motion, hand motion, griping, hand strength, and the like) and/or to induce or improve voiding of the bowel and/or bladder. The use of surface electrode(s), can facilitates selection or alteration of particular stimulation sites as well as the application of a wide variety of stimulation parameters. Additionally surface stimulation can be used to optimize location for an implantable electrode or electrode array for epidural stimulation.

In various embodiments, the methods described herein involve transcutaneous electrical stimulation of the cervical spine or a region of the cervical spine and/or the thoracic spinal cord or a region of the thoracic spinal cord, and/or a region of the lumbosacral spinal cord as described herein to facilitate locomotor activity and/or voiding of the bowel and/or bladder (e.g., as described above).

In certain embodiments the transcutaneous stimulation is at a frequency of at least about 1 Hz, or at least about 2 Hz, or at least about 3 Hz, or at least about 4 Hz, or at least about 5 Hz, or at least about 10 Hz, or at least about 20 Hz or at least about 30 Hz or at least about 40 Hz or at least about 50 Hz or at least about 60 Hz or at least about 70 Hz or at least about 80 Hz or at least about 90 Hz or at least about 100 Hz, or at least about 200 Hz, or at least about 300 Hz, or at least about 400 Hz, or at least about 500 Hz.

In certain embodiments the transcutaneous stimulation is at a frequency ranging from about 1 Hz, or from about 2 Hz, or from about 3 Hz, or from about 4 Hz, or from about 5 Hz, or from about 10 Hz, or from about 10 Hz, or from about 10 Hz, up to about 500 Hz, or up to about 400 Hz, or up to about 300 Hz, or up to about 200 Hz up to about 100 Hz, or up to about 90 Hz, or up to about 80 Hz, or up to about 60 Hz, or up to about 40 Hz, or from about 3 Hz or from about 5 Hz up to about 80 Hz, or from about 5 Hz to about 60 Hz, or up to about 30 Hz. In certain embodiments the transcutaneous stimulation is at a frequency ranging from about 20 Hz or about 30 Hz to about 90 Hz or to about 100 Hz.

In certain embodiments the transcutaneous stimulation is applied at an intensity ranging from about 5 mA or about 10 mA up to about 500 mA, or from about 5 mA or about 10 mA up to about 400 mA, or from about 5 mA or about 10 mA up to about 300 mA, or from about 5 mA or about 10 mA up to about 200 mA, or from about 5 mA or about 10 mA to up about 150 mA, or from about 5 mA or about 10 mA up to about 50 mA, or from about 5 mA or about 10 mA up to about 100 mA, or from about 5 mA or about 10 mA up to about 80 mA, or from about 5 mA or about 10 mA up to about 60 mA, or from about 5 mA or about 10 mA up to about 50 mA.

In certain embodiments the transcutaneous stimulation is applied stimulation comprises pulses having a width that ranges from about 100 μs up to about 1 ms or up to about 800 μs, or up to about 600 μs, or up to about 500 μs, or up to about 400 μs, or up to about 300 μs, or up to about 200 μs, or up to about 100 μs, or from about 150 μs up to about 600 μs, or from about 200 μs up to about 500 μs, or from about 200 μs up to about 400 μs.

In certain embodiments the transcutaneous stimulation is at a frequency, pulse width, and amplitude sufficient to initiate and/or improve standing, stepping, sitting, laying down, stabilizing sitting posture, stabilizing standing posture, arm motion, hand motion, griping, hand strength, and the like) and/or to induce or improve voiding of the bowel and/or bladder. In certain embodiments the stimulation is at a frequency, pulse width, and amplitude sufficient to provide at least 30% emptying or at least 40% emptying, or at least 50% emptying, or at least 60% emptying, or at least 70% emptying, or at least 80% emptying, or at least 90% emptying, or at least 95% emptying, or at least 98% emptying of the bladder and/or bowel e.g., upon application of electrical stimulation as described herein.

In certain embodiments the transcutaneous stimulation is superimposed on a high frequency carrier signal. In certain embodiments the high frequency carrier signal ranges from about 3 kHz, or about 5 kHz, or about 8 kHz up to about 30 kHz, or up to about 20 kHz, or up to about 15 kHz. In certain embodiments the carrier signal is about 10 kHz. In certain embodiments the carrier frequency amplitude ranges from about 30 mA, or about 40 mA, or about 50 mA, or about 60 mA, or about 70 mA, or about 80 mA up to about 300 mA, or up to about 200 mA, or up to about 150 mA.

Accordingly, in certain embodiments, the transcutaneous stimulation is applied as a high frequency signal that is pulsed at a frequency ranging from about 1 Hz up to about 100 Hz as described above. In one illustrative but nonlimiting embodiment, the stimulation is a 1 Hz transcutaneous electrical stimulation evoked with a 10 kHz constant-current bipolar rectangular stimulus for 0.5 ms at 30 to 100 mA repeated at 1-40 times per second for 10 to 30 s. This results in a low (2% or less) duty cycle that is well tolerated. In certain embodiments the voltage is approximately 30 V at 100 mA. In certain embodiments each stimulation epoch is repeated 1-10, or 1-5 times per session, once per week for, e.g., 6-12 weeks.

Epidural Stimulation.

In various embodiments, the methods described herein involve epidural electrical stimulation for stimulation of the spinal cord (e.g., spinal circuits) to facilitate locomotor activity (e.g., standing, stepping, sitting, laying down, stabilizing sitting posture, stabilizing standing posture, arm motion, hand motion, griping, hand strength, and the like) and/or to induce or improve voiding of the bowel and/or bladder.

In certain embodiments, the epidural stimulation is at a frequency of at least about 1 Hz, or at least about 2 Hz, or at least about 3 Hz, or at least about 4 Hz, or at least about 5 Hz, or at least about 10 Hz, or at least about 20 Hz or at least about 30 Hz or at least about 40 Hz or at least about 50 Hz or at least about 60 Hz or at least about 70 Hz or at least about 80 Hz or at least about 90 Hz or at least about 100 Hz, or at least about 200 Hz, or at least about 300 Hz, or at least about 400 Hz, or at least about 500 Hz.

In certain embodiments, the epidural stimulation is at a frequency ranging from about 1 Hz, or from about 2 Hz, or from about 3 Hz, or from about 4 Hz, or from about 5 Hz, or from about 10 Hz, or from about 10 Hz, or from about 10 Hz, up to about 500 Hz, or up to about 400 Hz, or up to about 300 Hz, or up to about 200 Hz up to about 100 Hz, or up to about 90 Hz, or up to about 80 Hz, or up to about 60 Hz, or up to about 40 Hz, or from about 3 Hz or from about 5 Hz up to about 80 Hz, or from about 5 Hz to about 60 Hz, or up to about 30 Hz.

In certain embodiments, the epidural stimulation is at a frequency ranging from about 20 Hz or about 30 Hz to about 90 Hz or to about 100 Hz.

In certain embodiments the epidural stimulation is at a frequency, pulse width, and amplitude sufficient to initiate and/or improve standing, stepping, sitting, laying down, stabilizing sitting posture, stabilizing standing posture, arm motion, hand motion, stimulate gripping, improve hand strength, and the like, and/or to induce or improve voiding of the bowel and/or bladder. In certain embodiments the stimulation is at a frequency, pulse width, and amplitude sufficient to provide at least 30% emptying or at least 40% emptying, or at least 50% emptying, or at least 60% emptying, or at least 70% emptying, or at least 80% emptying, or at least 90% emptying, or at least 95% emptying, or at least 98% emptying of the bladder and/or bowel e.g., upon application of electrical stimulation as described herein.

In certain embodiments, the epidural stimulation is at an amplitude ranging from 0.5 mA, or from about 1 mA, or from about 2 mA, or from about 3 mA, or from about 4 mA, or from about 5 mA up to about 50 mA, or up to about 30 mA, or up to about 20 mA, or up to about 15 mA, or from about 5 mA to about 20 mA, or from about 5 mA up to about 15 mA.

In certain embodiments, the epidural stimulation is with pulses having a pulse width ranging from about 100 µs up to about 1 ms or up to about 800 µs, or up to about 600 µs, or up to about 500 µs, or up to about 400 µs, or up to about 300 µs, or up to about 200 µs, or up to about 100 µs, or from about 150 µs up to about 600 µs, or from about 200 µs up to about 500 µs, or from about 200 µs up to about 400 µs.

In certain embodiments the epidural stimulation is applied paraspinally over a cervical region identified above (e.g., over vertebrae spanning C0 to C8 or a region thereof, e.g., over a region spanning C3 to C4).

In certain embodiments, the epidural stimulation is applied via a permanently implanted electrode array (e.g., a typical density electrode array, a high density electrode array, etc.).

In certain embodiments, the epidural electrical stimulation is administered via a high density epidural stimulating array (e.g., as described in PCT Publication No: WO/2012/094346 (PCT/US2012/020112). In certain embodiments, the high density electrode arrays are prepared using microfabrication technology to place numerous electrodes in an array configuration on a flexible substrate. In some embodiments, epidural array fabrication methods for retinal stimulating arrays can be used in the methods described herein (see, e.g., Maynard (2001) *Annu. Rev. Biomed. Eng.*, 3: 145-168; Weiland and Humayun (2005) *IEEE Eng. Med. Biol. Mag.*, 24(5): 14-21, and U.S. Patent Publications 2006/0003090 and 2007/0142878). In various embodiments, the stimulating arrays comprise one or more biocompatible metals (e.g., gold, platinum, chromium, titanium, iridium, tungsten, and/or oxides and/or alloys thereof) disposed on a flexible material. Flexible materials can be selected from parylene A, parylene C, parylene AM, parylene F, parylene N, parylene D, other flexible substrate materials, or combinations thereof. Parylene has the lowest water permeability of available microfabrication polymers, is deposited in a uniquely conformal and uniform manner, has previously been classified by the FDA as a United States Pharmacopeia (USP) Class VI biocompatible material (enabling its use in chronic implants) (Wolgemuth, Medical Device and Diagnostic Industry, 22(8): 42-49 (2000)), and has flexibility characteristics (Young's modulus ~4 GPa (Rodger and Tai (2005) *IEEE Eng. Med. Biology*, 24(5): 52-57)), lying in between those of PDMS (often considered too flexible) and most polyimides (often considered too stiff). Finally, the tear resistance and elongation at break of parylene are both large, minimizing damage to electrode arrays under surgical manipulation. The preparation and parylene microelectrode arrays suitable for use in the epidural stimulation methods described herein is described in PCT Publication No: WO/2012/100260 (PCT/US2012/022257).

The electrode array may be implanted using any of a number of methods (e.g., a laminectomy procedure) well known to those of skill in the art. For example, in some embodiments, electrical energy is delivered through electrodes positioned external to the dura layer surrounding the spinal cord. Stimulation on the surface of the cord (subdurally) is also contemplated, for example, stimulation may be applied to the dorsal columns as well as to the dorsal root entry zone. In certain embodiments the electrodes are carried by two primary vehicles: a percutaneous lead and a laminotomy lead. Percutaneous leads can typically comprise two or more, spaced electrodes (e.g., equally spaced electrodes), that are placed above the dura layer, e.g., through the use of a Touhy-like needle. For insertion, the Touhy-like needle can be passed through the skin, between desired vertebrae, to open above the dura layer. An example of an eight-electrode percutaneous lead is an OCTRODE® lead manufactured by Advanced Neuromodulation Systems, Inc.

Laminotomy leads typically have a paddle configuration and typically possess a plurality of electrodes (for example, two, four, eight, sixteen. 24, or 32) arranged in one or more columns. An example of an eight-electrode, two column laminotomy lead is a LAMITRODE® 44 lead manufactured by Advanced Neuromodulation Systems, Inc. In certain embodiments the implanted laminotomy leads are transversely centered over the physiological midline of a subject. In such position, multiple columns of electrodes are well suited to administer electrical energy on either side of the midline to create an electric field that traverses the midline. A multi-column laminotomy lead enables reliable positioning of a plurality of electrodes, and in particular, a plurality of electrode rows that do not readily deviate from an initial implantation position.

Laminotomy are typically implanted in a surgical procedure. The surgical procedure, or partial laminectomy, typically involves the resection and removal of certain vertebral tissue to allow both access to the dura and proper positioning of a laminotomy lead. The laminotomy lead offers a stable platform that is further capable of being sutured in place.

In the context of conventional spinal cord stimulation, the surgical procedure, or partial laminectomy, typically involves the resection and removal of certain vertebral tissue to allow both access to the dura and proper positioning of a laminotomy lead. Depending on the position of insertion, however, access to the dura may only require a partial removal of the ligamentum flavum at the insertion site. In certain embodiments, two or more laminotomy leads are positioned within the epidural space of C1-C7 as identified above. The leads may assume any relative position to one another.

In various embodiments, the arrays are operably linked to control circuitry that permits selection of electrode(s) to activate/stimulate and/or that controls frequency, and/or pulse width, and/or amplitude of stimulation. In various embodiments, the electrode selection, frequency, amplitude, and pulse width are independently selectable, e.g., at different times, different electrodes can be selected. At any time, different electrodes can provide different stimulation frequencies and/or amplitudes. In various embodiments, different electrodes or all electrodes can be operated in a monopolar mode and/or a bipolar mode, using constant current or constant voltage delivery of the stimulation. In certain embodiments time-varying current and/or time-varying voltage may be utilized.

In certain embodiments, the electrodes can also be provided with implantable control circuitry and/or an implantable power source. In various embodiments, the implantable control circuitry can be programmed/reprogrammed by use of an external device (e.g., using a handheld device that communicates with the control circuitry through the skin). The programming can be repeated as often as necessary.

The epidural electrode stimulation systems described herein are intended to be illustrative and non-limiting. Using the teachings provided herein, alternative epidural stimulation systems and methods will be available to one of skill in the art.

Stimulators and Stimulation Systems.

Magnetic Stimulators.

Magnetic nerve stimulators are well known to those of skill in the art. Stimulation is achieved by generating a rapidly changing magnetic field to induce a current at the nerve of interest. Effective nerve stimulation typically requires a current transient of about $10^8$ A/s. In certain embodiments this current is obtained by switching the current through an electronic switching component (e.g., a thyristor or an insulated gate bipolar transistor (IGBT)).

Figure 9:
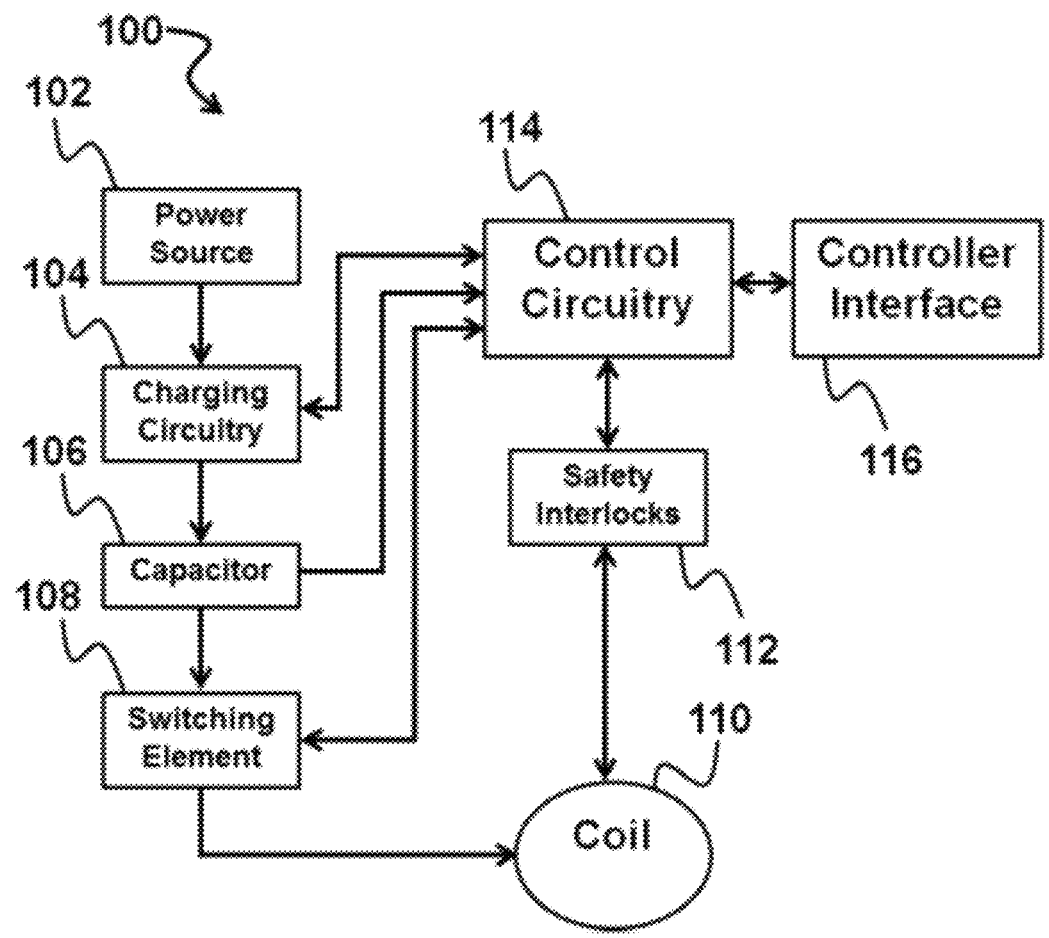
FIG. 9 shows a schematic illustration of one illustrative embodiment of a magnetic nerve stimulator.

FIG. 9 schematically shows one illustrative, but non-limiting embodiment of a magnetic stimulator. As shown therein, magnetic nerve stimulator 100 comprises two parts: a high current pulse generator producing discharge currents of, e.g., 5,000 amps or more; and a stimulating coil 110 producing magnetic pulses (e.g., with field strengths up to 4, 6, 8, or even 10 tesla) and with a pulse duration typically ranging from about 100 µs to 1 ms or more, depending on the stimulator type. As illustrated in FIG. 9, a voltage (power) source 102 (e.g., a battery) charges a capacitor 106 via charging circuitry 104 under the control of control circuitry 114 (e.g., a microprocessor) that accepts information such as the capacitor voltage, power set by the user, and various safety interlocks 112 within the equipment to ensure proper operation, and the capacitor is then connected to the coil via an electronic switching component 108 when the stimulus is to be applied. The control circuitry is operated via a controller interface 116 that can receive user input and/optionally signals from external sources such as internet monitors, health care professionals, and the like.

When activated, the discharge current flows through the coils inducing a magnetic flux. It is the rate of change of the magnetic field that causes the electrical current within tissue to be generated, and therefore a fast discharge time is important to stimulator efficiency.

As noted earlier the magnetic field is simply the means by which an electrical current is generated within the tissue, and that it is the electrical current, and not the magnetic field, that causes the depolarization of the cell membrane and thus the stimulation of the target nerve.

Since the magnetic field strength falls off with the square of the distance from the stimulating coil, the stimulus strength is at its highest close to the coil surface. The stimulation characteristics of the magnetic pulse, such as depth of penetration, strength and accuracy, depend on the rise time, peak electrical energy transferred to the coil and the spatial distribution of the field. The rise time and peak coil energy are governed by the electrical characteristics of the magnetic stimulator and stimulating coil, whereas the spatial distribution of the induced electric field depends on the coil geometry and the anatomy of the region of induced current flow.

The stimulating coils typically consist of one or more well-insulated copper windings, together with temperature sensors and safety switches.

In certain embodiments the use of single coils is contemplated. Single coils are effective in stimulating the human motor cortex and spinal nerve roots. To date, circular coils with a mean diameter of 80-100 mm have remained the most widely used magnetic stimulation. In the case of circular coils the induced tissue current is near z on the central axis of the coil and increases to a maximum in a ring under the mean diameter of coil.

A notable improvement in coil design has been that of the double coil (also termed butterfly or figure eight coil). Double coils utilize two windings, normally placed side by side. Typically double coils range from very small flat coils to large contoured versions. The main advantage of double coils over circular coils is that the induced tissue current is at its maximum directly under the center where the two windings meet, giving a more accurately defined area of stimulation.

The stimulating pulse may be monophasic, biphasic or polyphasic. Each of these has its own properties and so may be useful in particular circumstances. For neurology, single pulse, monophasic systems are generally employed; for rapid rate stimulators, biphasic systems are used as energy must be recovered from each pulse in order to help fund the next. Polyphasic stimulators are believed to have a role in a number of therapeutic applications.

Descriptions of magnetic nerve stimulators can be found, inter alia, in U.S. patent publications US 2009/0108969 A1, US 2013/0131753 A1, US 2012/0101326 A1, IN U.S. Pat.

Nos. 8,172,742, 6,086,525, 5,066,272, 6,500,110, 8,676, 324, and the like. Magnetic stimulators are also commercially availed from a number of vendors, e.g., MAGVENTURE®, MAGSTIM®, and the like.

Electrical Stimulators.

Any present or future developed stimulation system capable of providing an electrical signal to one or more regions of the cervical spinal cord may be used in accordance with the teachings provided herein. Electrical stimulation systems (e.g., pulse generator(s)) can be used with both transcutaneous stimulation and epidural stimulation.

In various embodiments, the system may comprise an external pulse generator for use with either a transcutaneous stimulation system or an epidural system. In other embodiments the system may comprise an implantable pulse generator to produce a number of stimulation pulses that are sent to the a region in proximity to the cervical spinal cord by insulated leads coupled to the spinal cord by one or more electrodes and/or an electrode array to provide epidural stimulation. In certain embodiments the one or more electrodes or one or more electrodes comprising the electrode array may be attached to separate conductors included within a single lead. Any known or future developed lead useful for applying an electrical stimulation signal in proximity to a subject's spinal cord may be used. For example, the leads may be conventional percutaneous leads, such as PISCES® model 3487A sold by Medtronic, Inc. In some embodiments, it may be desirable to employ a paddle-type lead.

Any known or future developed external or implantable pulse generator may be used in accordance with the teachings provided herein. For example, one internal pulse generator may be an ITREL® II or Synergy pulse generator available from Medtronic, Inc, Advanced Neuromodulation Systems, Inc.'s GENESIS™ pulse generator, or Advanced Bionics Corporation's PRECISION™ pulse generator. One of skill in the art will recognize that the above-mentioned pulse generators may be advantageously modified to modulate locomotor function and/or bladder and/or bowel control in accordance with the teachings provided herein.

In certain embodiments systems can employ a programmer coupled via a conductor to a radio frequency antenna. This system permits attending medical personnel to select the various pulse output options after implant using radio frequency communications. While, in certain embodiments, the system employs fully implanted elements, systems employing partially implanted elements may also be used in accordance with the teachings provided herein.

In one illustrative, but non-limiting system, a control module is operably coupled to a signal generation module and instructs the signal generation module regarding the signal to be generated. For example, at any given time or period of time, the control module may instruct the signal generation module to generate an electrical signal having a specified pulse width, frequency, intensity (current or voltage), etc. The control module may be preprogrammed prior to implantation or receive instructions from a programmer (or another source) through any known or future developed mechanism, such as telemetry. The control module may include or be operably coupled to memory to store instructions for controlling the signal generation module and may contain a processor for controlling which instructions to send to signal generation module and the timing of the instructions to be sent to signal generation module.

In certain embodiments, the controller alters and/or locomotor function and/or initiates or facilitates voiding of the bladder and/or bowel on demand.

In various embodiments, leads are operably coupled to signal generation module such that a stimulation pulse generated by signal generation module may be delivered via electrodes.

While in certain embodiments, two leads are utilized, it will be understood that any number of one or more leads may be employed. In addition, it will be understood that any number of one or more electrodes per lead may be employed. Stimulation pulses are applied to electrodes (which typically are cathodes) with respect to a return electrode (which typically is an anode) to induce a desired area of excitation of electrically excitable tissue in a region of the cervical spine. A return electrode such as a ground or other reference electrode can be located on same lead as a stimulation electrode. However, it will be understood that a return electrode may be located at nearly any location, whether in proximity to the stimulation electrode or at a more remote part of the body, such as at a metallic case of a pulse generator. It will be further understood that any number of one or more return electrodes may be employed. For example, there can be a respective return electrode for each cathode such that a distinct cathode/anode pair is formed for each cathode.

In various embodiments, the independent electrodes or electrodes of electrode arrays are operably linked to control circuitry that permits selection of electrode(s) to activate/stimulate and/or controls frequency, and/or pulse width, and/or amplitude of stimulation. In various embodiments, the electrode selection, frequency, amplitude, and pulse width are independently selectable, e.g., at different times, different electrodes can be selected. At any time, different electrodes can provide different stimulation frequencies and/or amplitudes. In various embodiments, different electrodes or all electrodes can be operated in a monopolar mode and/or a bipolar mode, using, e.g., constant current or constant voltage delivery of the stimulation.

In one illustrative but non-limiting system a control module is operably coupled to a signal generation module and instructs the signal generation module regarding the signal to be generated. For example, at any given time or period of time, the control module may instruct the signal generation module to generate an electrical signal having a specified pulse width, frequency, intensity (current or voltage), etc. The control module may be preprogrammed prior to use or receive instructions from a programmer (or another source). Thus, in certain embodiments the pulse generator/controller is configurable by software and the control parameters may be programmed/entered locally, or downloaded as appropriate/necessary from a remote site.

In certain embodiments the pulse generator/controller may include or be operably coupled to memory to store instructions for controlling the stimulation signal(s) and may contain a processor for controlling which instructions to send for signal generation and the timing of the instructions to be sent.

While in certain embodiments, two leads are utilized to provide transcutaneous or epidural stimulation, it will be understood that any number of one or more leads may be employed. In addition, it will be understood that any number of one or more electrodes per lead may be employed. Stimulation pulses are applied to electrodes (which typically are cathodes) with respect to a return electrode (which typically is an anode) to induce a desired area of excitation of electrically excitable tissue in one or more regions of the spine. A return electrode such as a ground or other reference electrode can be located on same lead as a stimulation electrode. However, it will be understood that a return electrode may be located at nearly any location, whether in proximity to the stimulation electrode or at a more remote part of the body, such as at a metallic case of a pulse generator. It will be further understood that any number of one or more return electrodes may be employed. For example, there can be a respective return electrode for each cathode such that a distinct cathode/anode pair is formed for each cathode.

EXAMPLES

The following examples are offered to illustrate, but not to limit the claimed invention.

Example 1

Accessing Spinal Networks to Enable Locomotor Function

FIG. 1 illustrates magnetic neuromodulation of the cervical spinal cord in SCI. Five subjects with stable SCI (>1 year) were evaluated with a battery of tests once a week for 3 months to establish a pre-treatment baseline, with the last month shown here (Pre). Subjects were then treated weekly with EMSS and tested weekly for a month (Treat). Subjects were then tested weekly for a month without treatment to determine the durability of the treatment (Post). Panel A shows a direct measure of the force generated by subjects with their dominant hand (handgrip strength). Individuals all had improved performance of various magnitudes. As shown in A' subjects had an average of 5-fold improvement in strength that was highly significant. Panel B shows a Spinal Cord Independence Measure (SCIM) which is a 17-item measure of 0-100 with a Minimally Clinical Important Difference of 4 points. There may be two classes of response in this measure. B* Subjects had ~30 point increase indicating a robust clinical improvement which was significant. Panel C shows a modified Ashworth that provides a measure of spasticity of 1-4 on ten muscles for a 40-point max. All subjects had improvement in overall spasticity in arms and legs, although subject C had modest improvements. C' average spasticity was reduced by half. Panel D shows the results of an Arm Reach Action Test (ARAT) which is a 19-item measure of 0-60. D' Subjects had ~50% increase in performance on this measure. E. International Standards for Neurological Classification of Spinal Cord Injury (ISNCSCI) upper extremity motor exam of five muscles in each arm on a scale for 0-5 for a 50-point max. Minimally Clinical Important Difference is 1 point. E' Subjects had ~30% improvements. F. Columbia Suicide Survey. Subject C had substantial suicidality that was reduced. F' no subjects reported suicidality by the last month of the study. Two Tailed Students T-test with Bonferroni post-hoc correction. *p<0.05; p<0.01; *p<0.001. Device: MagPro (MagVenture, Atlanta) with Cool-B35 Butterfly Coil and Biphasic stimulation at 30 Hz.

Figure 2:
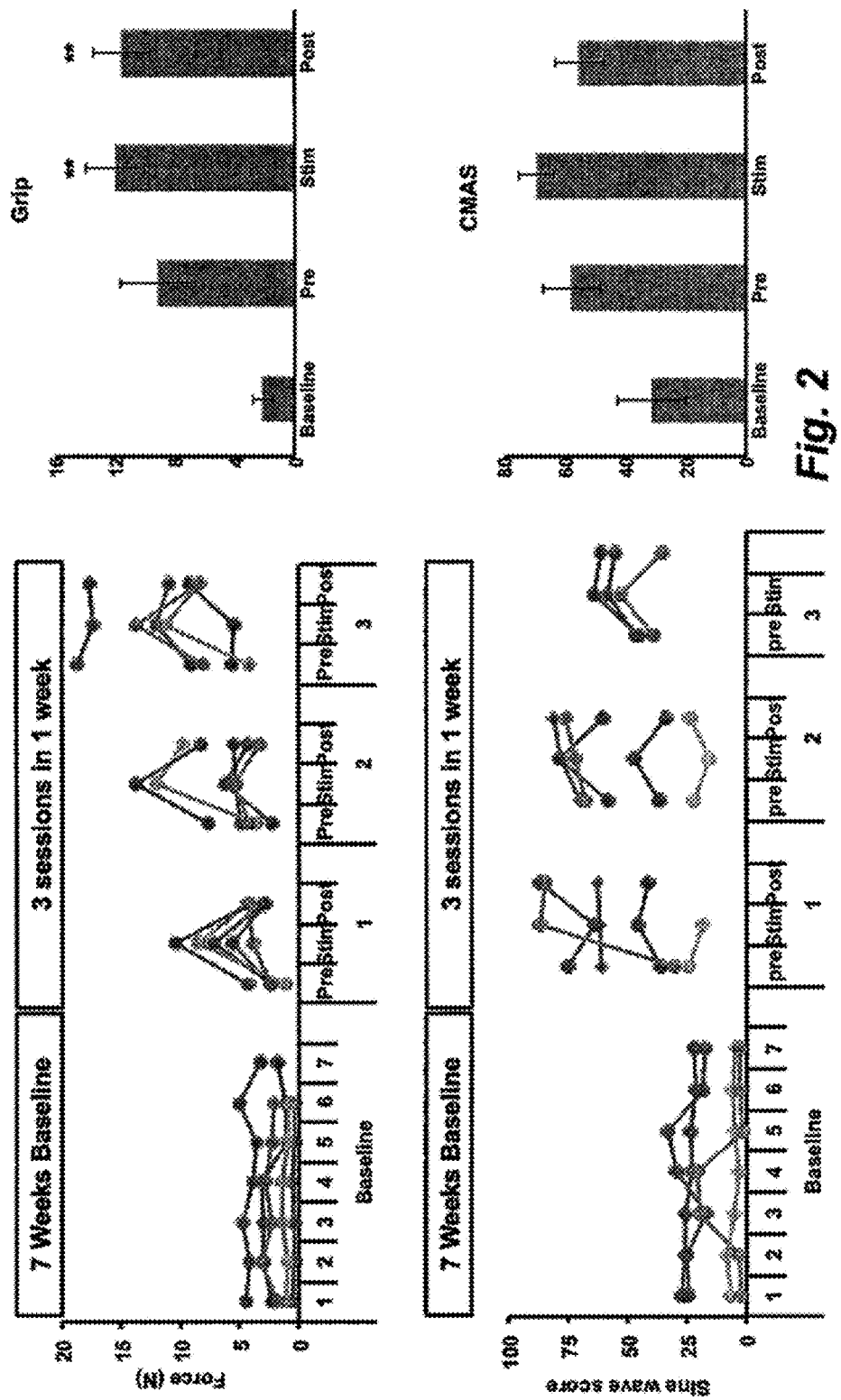
FIG. 2 shows that buspirone (BUS)+EMSS can act rapidly. In a separate cohort, we established baseline function for 7 weeks followed by treatment with BUS treatment. Two Tailed Students T-test with Bonferroni post-hoc correction. * $p<0.05$;  $p<0.01$; * $p<0.001$. Device: MagPro (MagVenture, Atlanta) with Cool-B35 Butterfly Coil and Biphasic stimulation at 30 Hz.

FIG. 2 shows that BUS+EMSS can act rapidly. In a separate cohort, we established baseline function for 7 weeks followed by treatment with BUS treatment. E MSS was conducted on day 3, 5, and 7 of BUS treatment. A. In grip strength, a rapid and significant increase in grip was seen even in the first session. A'. By the last session, as summarized, there was a robust increase in grip strength both before and after stimulation. B. In a measure of precision hand movements where a subject follows a sine wave on a screen by moving a pointer, substantial increases were seen in the first session. B'. Although not reaching significance, these data appear to trend towards improvement. Two Tailed Students T-test with Bonferroni post-hoc correction. *p<0.05; p<0.01; *p<0.001. Device: MagPro (MagVenture, Atlanta) with Cool-B35 Butterfly Coil and Biphasic stimulation at 30 Hz.

Figure 3:
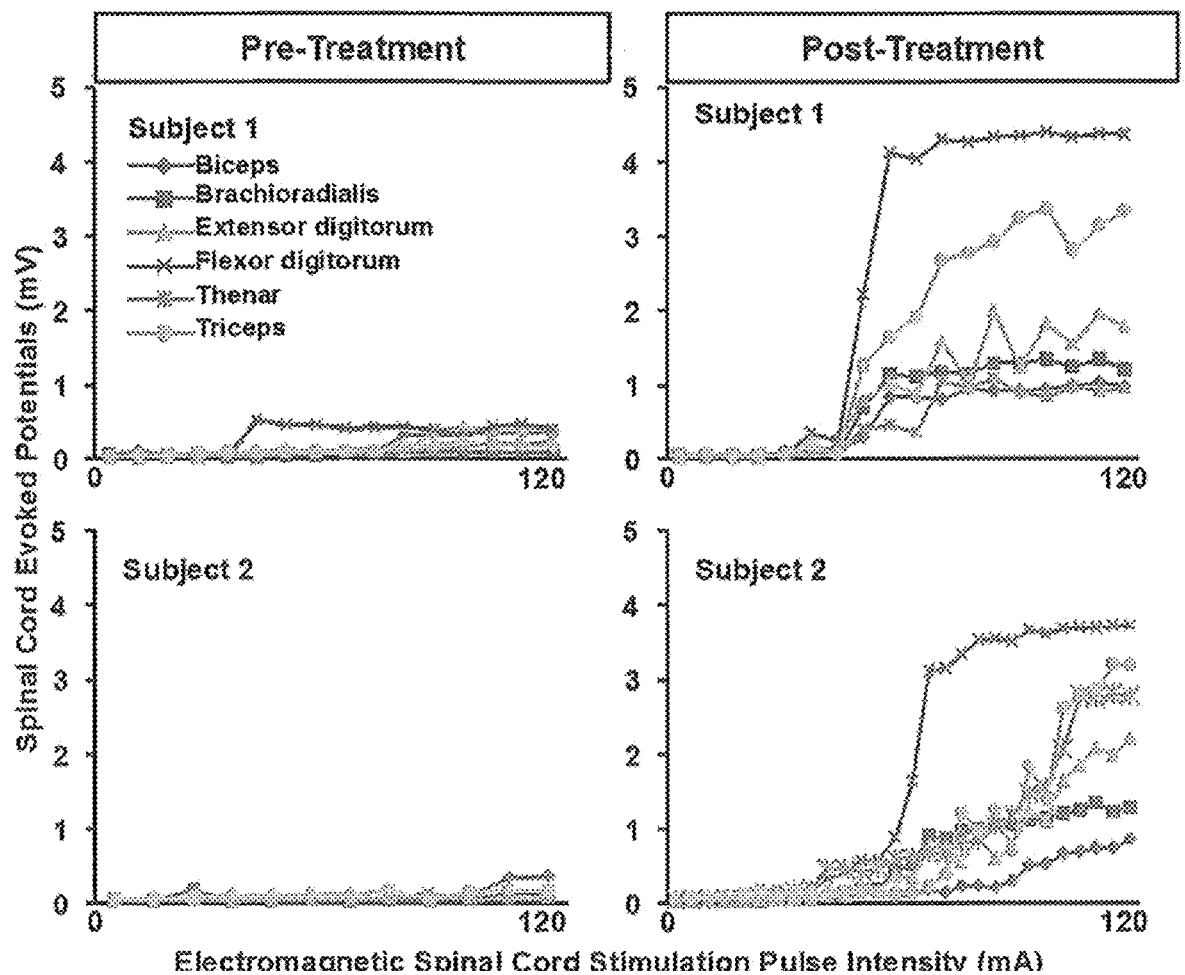
FIG. 3 illustrates the effect of EMSS treatment on spinal cord evoked potentials.

FIG. 3 illustrates the effect of EMSS treatment on spinal cord evoked potentials. Subjects with stable cervical SCI were evaluated for their ability to produce Spinal Cord Evoked Potentials (SCEPs) with EMSS pre- and post-treatment. The Y-axis indicates the size of the evoked potential measured by EMG at the relevant muscle. The X-axis is increasing stimulation intensity with EMSS. In the right panels, two subjects were evaluated before treatment. Both subjects have some activity at all the motor pools evaluated, although not apparent at this scale. In the left panels, the same two subjects were evaluated post-treatment. A large treatment effect is seen in the SCEPs reflecting changes in spinal cord circuitry related to motor function. This technique can be used to measure the inherent segmental responsiveness of the cord. This technique does not require volitional control of the segmental levels in question and is therefore well suited to evaluating subjects with paralysis.

Example 2

Transcutaneous Electrical Stimulation to Promote Recovery of Bladder Function After Spinal Cord Injury Catheter associated urinary tract infections are the most common healthcare related infection (Klevens et al. (2007) *Public health reports* 122: 160-166; Hidron et al. (2008) *J. Soc. Hosp. Epidemol. Am.* 29: 996-1011) affecting individuals dependent reliant upon catheterization to void their bladder due to neurological disease or trauma. Individuals with spinal cord injury experience high rates of urinary tract infections, obstructive uropathies, and reduced quality of life scores (Manack et al. (2011) *Neurol. Urodynam.* 30: 395-401; Anderson (2004) *J. Neurotrauma*, 21: 1371-1383; Nicolle (2014) *Curr. Infect. Dis. Rep.*, 16: 390) due to neurogenic bladder dysfunction, which can also present in other conditions, e.g. multiple sclerosis (Mahajan et al. (2014) *Int.* 1 MS Care, 16: 20-25). Neuromodulatory strategies to activate bladder function by electrically stimulating peripheral nerves and/or muscles (Bartley et al. (2013) *Nat. Rev. Urol.*, 10: 513-521; Brindley (1974) *J. Physiol.*, 237: 15P-16P), or alter bladder innervation to effect a permissive neurologic tone, e.g. Brindley rhizotomy (Van Kerrebroeck et al. (1996) *J. Urol.*, 155: 1378-1381), only modestly recapitulate the orchestrated sequence of muscle contraction and relaxation that occurs during normal micturition (Seth et al. (2013) *Handbook Clin. Neurol.*, 117: 111-117).

We report bladder function improvements in two patients participating in research of non-invasive electrical stimulation of the lumbosacral spinal cord to improve leg motor function (Gorodnichev et al. (2010) *Fiziologiia cheloveka*, 36: 95-103; Lu et al. (2015) *Front. Mol. Neurosci.* 8:25). Urodynamic studies demonstrated that transcutaneous electrical stimulation focused on the lumbosacral spinal cord resulted in sufficient voiding to reduce or eliminate catheterization. This intervention resulted in improved quality of life and independence while reducing urinary tract infections. Here we report these fortuitous observations in five subjects and case reports of two subjects specifically treated to affect bladder function.

Case Report

Figure 4:
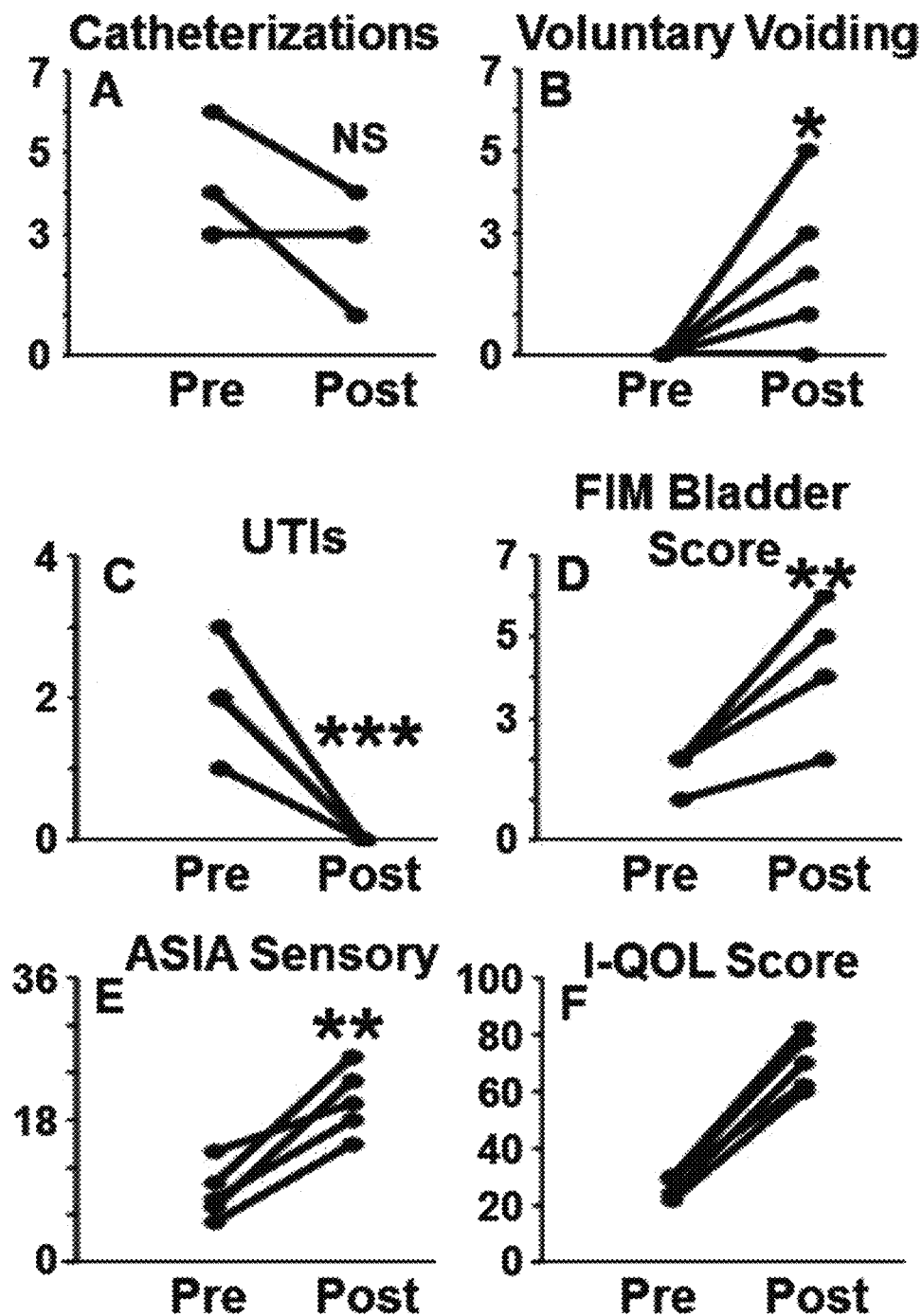
FIG. 4, panels A-F, show observed improvements in bladder function. Five subjects with complete motor SCI (ASIA B, 36-46 months, 3 cervical 2 thoracic) underwent transcutaneous lumbosacral stimulation to improve lower limb function. Baseline bladder function was assessed prior to and again after 6 months of stimulation trials. Panel A) Daily catheterizations trend towards being reduced. Panel B) 4 of 5 subjects acquired the ability to voluntarily void one or more times daily. Panel C) 5 of 5 subjects had no UTIs for 6 months. Panel D) FIM bladders score (max=7) was increased in all subjects. Panel E) The ASIA sensory score (max=36) was significantly increased in all subjects. Panel F) Critically, there was an increase in the I-QOL score (max=100) indicating a profound improvement in the quality of life reported by these subjects. Catheterizations and voluntary voiding are per day; UTI's are per 6 months. Student's two-tailed T-test *=$p<0.05$, =$p<0.01$, *=$p<0.001$ with Bonferonni post-hoc correction.

The use of transcutaneous electrical stimulation of the spinal cord is part of a clinical research protocol on the evaluation and treatment of patients with spinal cord injury (Protocol 11-001720) that was approved by the institutional review board of the University of California, Los Angeles. Informed consent was obtained from each patient. During the course of these studies, we observed urination in subjects. We began monitoring bladder function by diary and observed significant improvements in bladder function, independence, and quality of life (FIG. 4, panel A). Based on these findings, we pursued more formal study of two individuals (FIG. 4, panel B, and 5).

Patient 1

Here we describe a 45-year-old male cattleman who fell from a horse in 2011. In the emergency department, the patient had no movement or sensation below thoracic (T) level 3. Imaging in emergency department showed sternal fracture, a left pneumothorax, as well as MRI-confirmed complete obliteration of the spinal canal at T3. Testing at admission was ASIA A score. Stabilization was performed with posterior fusion and instrumentation at T1 to T5. Postoperative care consisted of conventional standard of care rehabilitation at outpatient centers. After 3 years of rehabilitation he had no motor function of trunk or leg muscles, a flaccid anal sphincter, and no voluntary bladder contraction by urodynamic study. Sensation was abnormal below T4. He was reliant on clean intermittent catheterization (CIC) and a bowel protocol. He experienced urination accidents approximately twice a week and UTIs approximately once a month.

Figure 5:
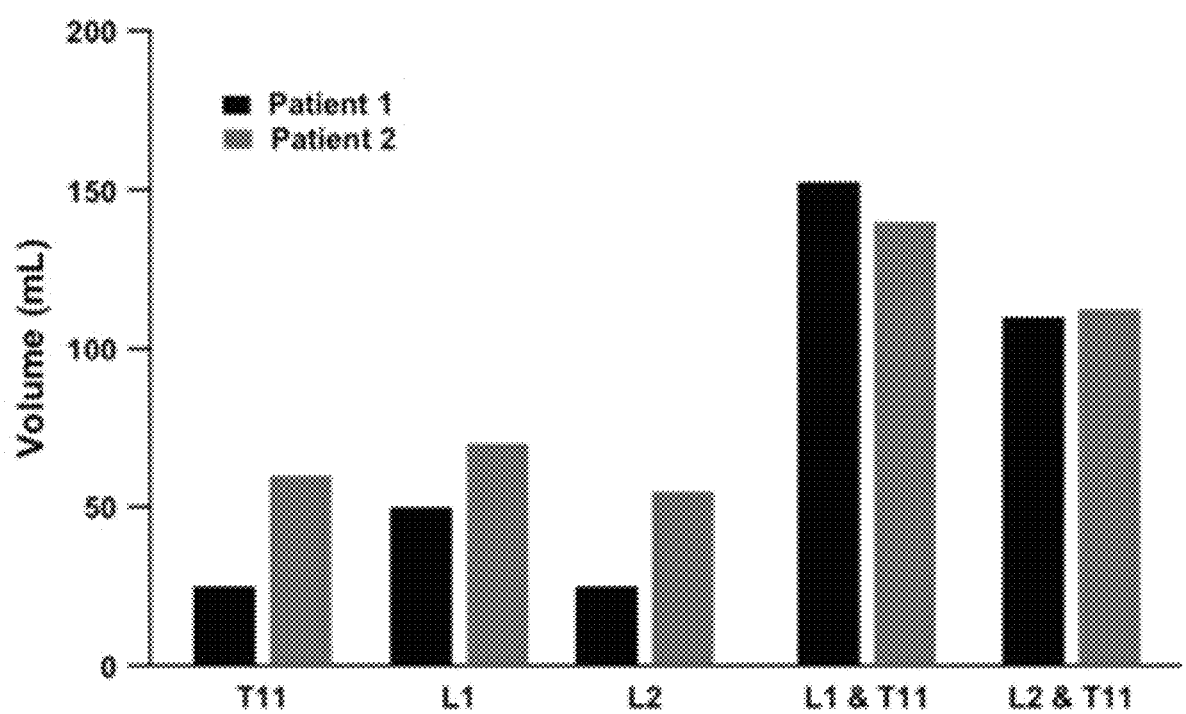
FIG. 5 shows voiding volumes due to transcutaneous spinal cord stimulation. When 5 milliseconds of 10 kHz stimulation is applied every second, voluntary micturition can be enabled in catheterization-dependent spinal cord injured subjects. Stimulation of either lower thoracic or upper lumbar region is modestly effective, while stimulation of both thoracic and lumbar regions simultaneously shows greatly improved voiding function.

While investigating lumbosacral stimulation to improve leg motor function, involuntary bladder voiding was observed in Patient 1 that suggested that this neuromodulation acted on sensory and/or motor centers in the spinal cord affecting bladder function. The subject was then asked to keep a bladder function diary to monitor this side effect (FIG. 4). Subsequently, we began transcutaneous stimulation of Patient 1 over the lumbosacral cord to evaluate voiding, specifically. We observed that the patient was able to void volitionally in the presence of specific stimulation parameters (FIG. 5).

A stimulation protocol was developed and administered once-a-week for six weeks, with urinary flow measurements collected. Patient 1 underwent urodynamic studies prior to, and at the conclusion of, the six-week protocol (FIG. 5).

Figure 6:
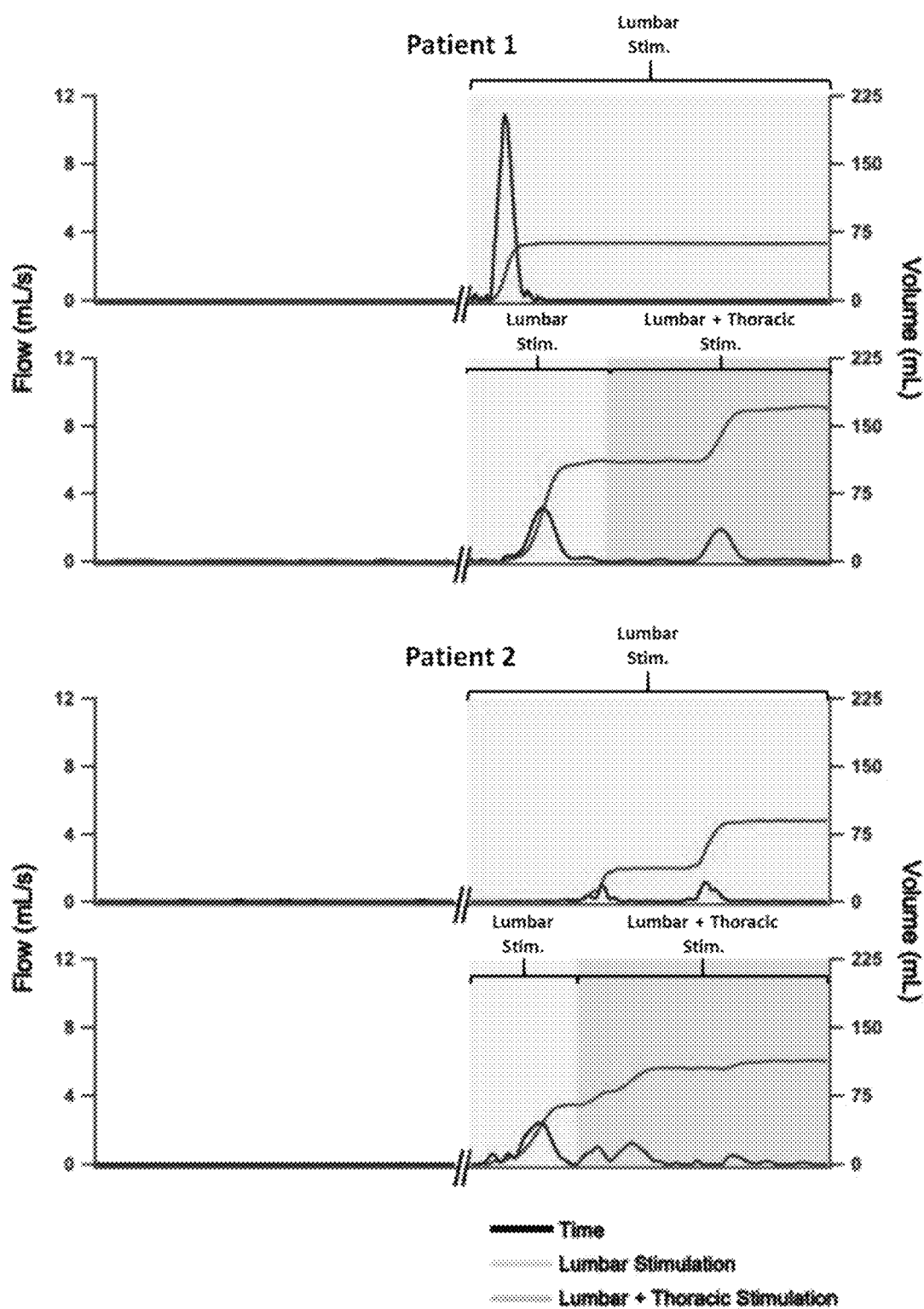
FIG. 6 shows a voiding cystometrogram of two subjects with transcutaneous spinal cord stimulation. Two representative cystometrogram of three subjects are shown in early (top) and late (bottom) voiding trials within the 2 month time frame. Subjects were asked to void without stimulation for 10 minutes, in which no volitional voiding was observed. Subsequently, voiding was observed with stimulation. Higher volume of voiding is observed in later trials and with multi-site stimulation. Shaded regions represent lumbar stimulation or lumbar and thoracic stimulation as shown. Flow in milliliters per second is represented in dotted line while total volume voided in milliliters is in solid line.
Figure 7:
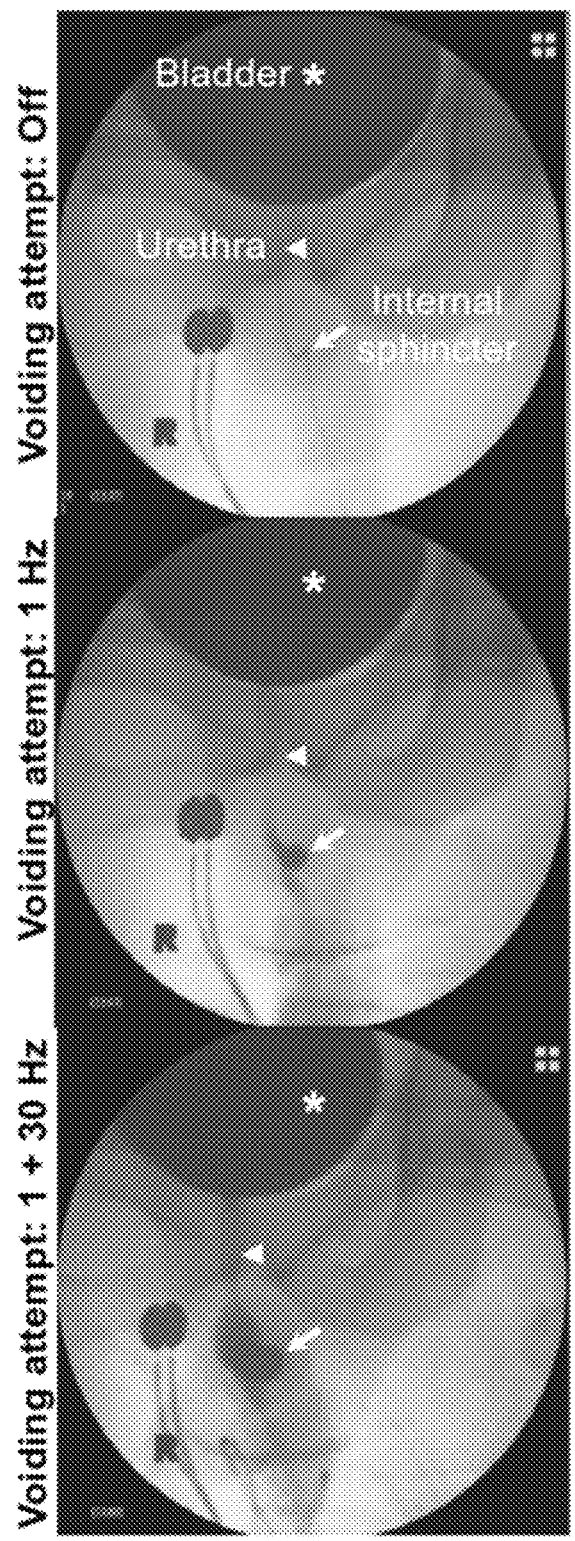
FIG. 7 shows representative video urodynamic of a representative subject. Video urodynamic testing was conducted on subject in two separate occasions separated by 14 days. Patient was instructed to void voluntarily (left panel) and void voluntarily with stimulation (right panel). With stimulation, the subject was able to void in both occasions. However, in the later session, the subject was able to void even in the setting of no stimulation. In successful voiding, fluoroscope image demonstrates urine flow with opening of the internal sphincter and contrast material in the urethra. In all voids, there is concomitant rise in detrusor and bladder pressure coincident with urine flow. Stimulation was at 1 Hz with a 10 kHz carrier frequency.

Prior to the stimulation protocol, no volitional voiding was present. We performed stimulation while monitoring intravesicular, intra-abdominal and detrusor pressures, and flow rate, to evaluate the subject's ability to void volitionally in the presence or absence of transcutaneous spinal cord stimulation. In the presence of 1 ms of 10 kHz stimulation once per second at L1 the subject was able to reach flow rates of greater than 10 mL per second (FIG. 6). This flow rate was under volitional control and corresponded with increased vesicular, and not increased abdominal, pressure.

This subject had reductions in daily catheterizations and UTIs. The subject also had increased voluntary voiding, FIM bladder score, ASIA sensory improvements, and I-QOL score (FIG. 4, Panel B).

Patient 1 has recently reported that catheterization is not required in the morning and no UTIs have been observed over six months of follow up care.

Patient 2

Patient 2 is a 58-year-old male who suffered a cervical spinal cord injury from a bicycle accident in 2009. He underwent T1-6 pedicle screw fixation and arthrodesis for T3-T4 dislocation and subluxation resulting in a motor-complete spinal cord injury (ASIA-B) below the T3-T4 level. He also underwent occiput to C4 arthrodesis for C1 burst fracture, odontoid fracture and cervical instability. He was reliant on CIC and bowel protocol. He had approximately 1 weekly urinary accident and a UTI approximately every 2-3 months. He had no motor function of trunk or leg muscles, and no voluntary bladder contraction by urodynamic study.

Patient 2 underwent the same training protocol as Subject 1. Prior to training, no volitional voiding was present. In the presence of 1 ms of 10 kHz stimulation once per second at L1 the subject was able to reach flow rates of 4.5 mL per second.

This subject had reductions in daily catheterizations and UTIs. The subject also had increased voluntary voiding, FIM bladder score, ASIA sensory improvements, and I-QOL score (FIG. 4, panel b).

Patient 2 has recently reported that catheterization is not required in the morning and no UTIs have been observed during six months of follow up. Furthermore, urodynamics performed 6 months after this protocol cessation revealed some capacity for volitional voiding.

Methods

Stimulation:

Transcutaneous stimulation of the lumbosacral spinal cord was performed using a KULON stimulator (St. Petersburg State University of Aerospace Instrumentation, St. Petersburg, Russia) 11. The stimulation was applied with a 2.5 cm round electrodes (Lead-Lok, Sandpoint, United States) placed midline on the skin between the spinous processes of T11 and T12 and S1 as a cathode and two 5.0×10.2 $cm^2$ rectangular plates made of conductive plastic (Ambu, Ballerup, Germany) placed symmetrically on the skin over the iliac crests as anodes. The micturition was evoked with a 10 kHz constant-current bipolar rectangular stimulus for 0.5 ms at 30 to 100 mA repeated at 1-40 times per second for 10 to 30 s. This results in a low (2% or less) duty cycle that is well tolerated. Voltage was approximately 30 V at 100 mA. Each stimulation epoch was repeated 1-5 times per session, once per week for 6-12 weeks.

Bladder Training Sessions:

A uroflow system was used to measure total voided volume and flow rate, consisting of ATmega168 microcontroller (Atmel Corporation, San Jose, Calif.), AD620 amplifier (Analog Devices, Norwood, Mass.), strain gauge taken from an American Weigh AMW-1000 scale (American Weigh Scale, Norcross, Ga.), and a 1 L graduated cylinder. Data acquisition software was written in Python. The data was subsequently filtered and processed using MatLab. The uroflow device was calibrated before every session, and the final voided volume reading consistently matched the amount of volume in the graduated cylinder.

Urodynamics Testing:

Pressure-void volume studies were conducted using the Aquarius XT system (Laborie Medical Technologies, Toronto, Ontario; please note that the system wasn't able to record flow measurements because patient was in supine position). The patient was placed in supine position and the bladder completely emptied by insertion of Foley catheter. External electrodes were placed to measure EMG activity of external sphincter. Two electrodes for transcutaneous electrical stimulation were placed on spinal cord vertebral levels T11 and L1 as cathodes. Two ground electrodes were placed on iliac crests bilaterally as anodes. The bladder-filling phase started with a slow instillation speed of 30-50 ml/min. Anatomical shape and size of the bladder, as well as vesicoureteral reflux, was assessed by fluoroscopic images. The filling continued until the patient felt fullness in the bladder; and/or blood pressure increases by >10 mmHg; and/or 400 ml fluid volume in the bladder. When the bladder was full, the patient was asked to cough to assess leakage, and abdominal pressure increase due to diaphragm contraction. Then the patient was asked to volitionally void for 5 minutes. The voided urine volume was be collected in a graduated urinal. Then 10 kHz stimulation was applied every second on proximal lumbar level (L1-L2), while the patient attempted to void volitionally. The vesicular, abdominal and detrusor pressure was measured. After observing a substantial increase in vesicular pressure, a 1 ms 10 kHz stimulation at 30 Hz was applied to T11-T12 (in addition to the 1 Hz stimulation at L1-L2), while the patient was trying to void. The voided volume was collected and the residual volume was measured by using a Foley catheter to empty the bladder. The stimulation time with every combination was less than 2 minutes and maximum of four combinations were tried in each session.

Discussion

The coordinated neuromuscular control of urinary bladder function by the sensory, motor, and autonomic nervous systems can be impaired by degenerative or traumatic changes, such as multiple sclerosis or spinal cord injury (Ginsberg (2013) *Am. J. Manag. Care,* 19: s191-196). Here we show that transcutaneous stimulation of the spinal cord can enable volitional micturition in catheterization-dependent individuals with spinal cord injury.

It has been observed that isolated regions of the lumbosacral cord contain neural circuitries to carry out complex motor behaviors (Hidron et al. (2008) *J. Soc. Hosp. Epidemol. Am.* 29: 996-1011; Alaynick et al. (2011) *Cell,* 146: 178-178.e.1; Sugaya and De Groat (1994) *Am. J. Physiol.,* 266: R658-667). Motor behaviors in animals and human subjects with chronic paralysis from spinal cord injury have shown improvements with invasive stimulation, including some volitional movements (Harkema et al. (2011) *Lancet* 377: 1938-1947; Angeli et al. (2014) *Brain,* 137: 1394-1409). It has been shown that motor commands can be transmitted through the commissural projections of propriospinal pathway, which can be trained to improve voluntary corticospinal control on lower extremity (Alaynick et al. (2011) *Cell,* 146: 178-178.e.1). This may apply to bladder control, which is supported by the observation that subjects can regain volitional micturition requiring micturition centers of the brain under conscious control communicating to spinal micturition centers (Edgerton and Harkema (2011) *Expert Rev. Neurotherap.* 11: 1351-1353). Minimally, the stimulation used in the present report ( )Gorodnichev et al. (2010) *Fiziologiia cheloveka,* 36: 95-103 appears to facilitate activation of autonomic and somatic motor neurons below the level of injury (Alaynick et al. (2011) *Cell,* 146: 178-178.e.1). Empirically, we speculate that previously subthreshold descending corticospinal and reticulospinal projections are activated during volitional micturition. Subjects also reported sensations of urgency that were not present before intervention suggesting facilitation of ascending spinothalamic pathways. We believe that because the stimulation produces coordinated activity it is activating central pattern generating interneuron circuitry in the cord (Lu et al. (2015) Front. Mol. Neurosci. 8:25; Alaynick et al. (2011) *Cell,* 146: 178-178.e.1), although peripheral afferents and efferent pathways are likely activated due to the imprecise delivery of transcutaneous electrical stimulation.

Transcutaneous electrical stimulation of nerves has been reported for several indications (Doucet et al. (2012) *Yale J. Biol. Med.* 85: 201-215), however investigators have not focused on the central nervous system for safety issues or because the amount of energy required to reach deeper structures resulted in intolerable pain. We observe that this stimulation paradigm can modulate neural function at subthreshold levels (Gad et al. (2013) *J. Neuroengin. Rehab.* 10: 108) and is tolerated in both patients and intact subjects; perhaps due to the waveform or relatively small fraction of time that energy is delivered.

Dysfunctions in the autonomic nervous system negatively affect vascular tone (Gefen (2014) *Ostomy/Wound Manag.* 60: 34-45), diaphoresis (Fast (1977) *Arch. Phys. Med. Rehab.* 58: 435-437), and immune function (Leicht et al. (2013) *Exer. Immunol. Rev.* 19: 144-163). These changes, in combination with bowel and bladder incontinence, set the stage for skin breakdown and ulcers in addition to UTIs (Eves and Rivera (2010) *Home Healthcare Nurse* 28: 230-241). Along with autonomic dysreflexia (Vaidyanathan et al. (2012) *Int. J. Emerg. Med.* 5: 6), these issues result is the majority of morbidity and mortality in individuals with spinal cord injury (Trautner and Darouiche (2002) *J. Spinal Cord Med.* 25:2 77-283). Further study of transcutaneous stimulation is useful in the context of urogenital disorders, bowel function, as well as skeletal motor function.

Example 3

Effect of Transcutaneous Magnetic Stimulation on Restoration of Bladder Functions in Chronic Spinal Cord Injured Patients This example describes a pilot clinical study of motor complete spinal cord injured subjects with neurogenic bladder. We demonstrate that the micturition circuit within the spinal cord can be neuromodulated with non-invasive magnetic stimulation to enable and restore bladder function.

Urinary dysfunction is a top quality of life complaints from chronic spinal cord injured (SCI) individuals. We tested the hypothesis that non-invasive, transcutaneous magnetic spinal cord stimulation (TMSCS) could modulate and improve bladder function in individuals with SCI. Five individuals with American Spinal Injury Association (ASIA) grade AB chronic SCIs and detrusor sphincter dyssynergia (DSD), who were dependent on cauterization, were enrolled in this prospective interventional study in which each subject was blinded to treatment and acted as his own control. After a two-week assessment to determine optimal stimulation characteristics, each patient received sixteen weeks of weekly TMSCS with the optimal stimulation frequency and then received "sham" weekly stimulation for six weeks while bladder function was monitored. Bladder function was assessed with urodynamic studies. As described in detail below, bladder function improved in all five subjects, but, in this study, only during and after with the low frequency (e.g., 1 Hz) stimulation. All subjects achieved volitional urination, even when stimulation was not present. After 16 weeks of TMSCS, the subjects needed fewer catheterization per day (6.6/day to 2.4/day, p=0.04); could urinate voluntarily (0 cc/day to 1120 cc/day, p=0.03); had an increase in bladder capacity (244 ml to 404 ml, p=0.02); could generate significant stream velocities (0 cc/sec to 9.3 cc/sec, p<0.001) and enjoyed a higher quality of life (i-QOL rose from 47 to 82, p=0.007).

Figure 8:
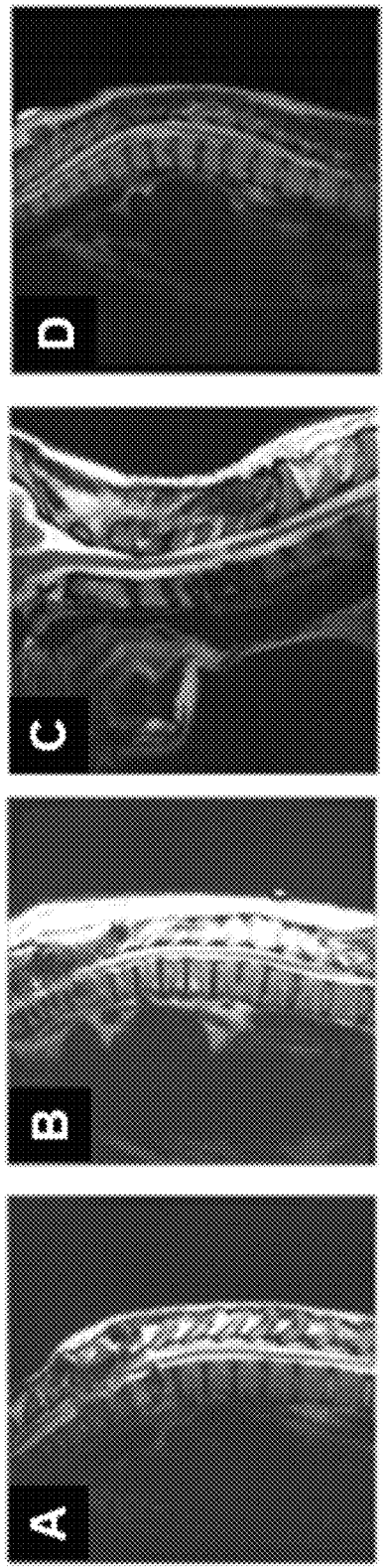
FIG. 8 shows MM imaging in four of SCI subjects. Sagittal MRI showing the approximate location (spinal cord segment) of the cervical or thoracic spinal cord injury in subjects A-D: A(T3-4); B(T3-T4); C(C5-C6); D(T5-T6). Normal tissue at the injury site is replaced by a high or mixed intensity signal representing a glial scar. Spinal cord tissue distal and proximal to the injury site appears intact without any evidence of progressive post-traumatic syrinx formation or ongoing compressive lesion. Image artifact from the instrumentation distorting the spinal cord image can be visualized.

Magnetic energy, acting through Faraday's law, generates an electromotive force that can be used to modulate neuronal circuits, and with focused FIG. 8 coils, the energy can be targeted to some extent. Magnetic stimulation is not only completely non-invasive, but also painless. Transcranial magnetic stimulation (TMS) has been used extensively to activate cortical circuits, and TMS is currently approved for migraine treatment (Zhu and Marmura (2016) *Curr. Neurol. Neurosci. Rep.* 16: 11). However, it has also been used to modulate neuronal functions in a variety of settings from depression (Perera et al. (2016) *Brain Stim.*, 9: 336-346) to restoration of motor function after ischemic stroke (Kim et al. (2016) *J. Stroke*, 18: 220-226).

Figure 10:
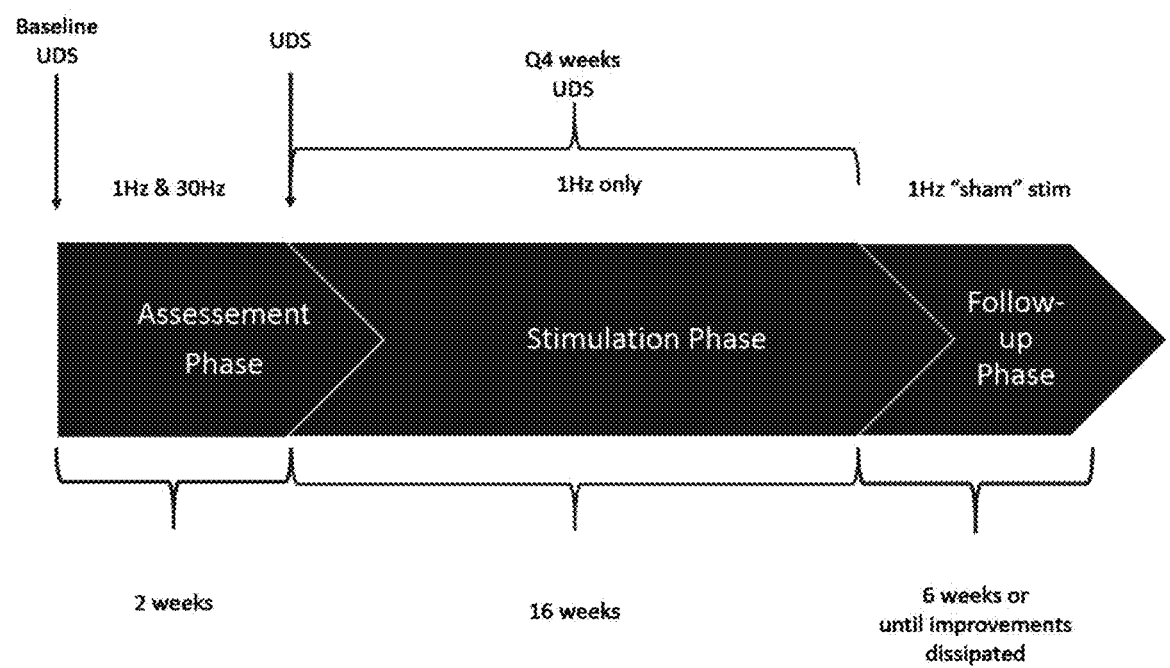
FIG. 10 shows an overview of the study. There were three phases of the study: assessment, stimulation and follow-up. The time frame for each is shown in the flow chart. During the assessment phase, each subject received stimulation with both 1 Hz and 30 Hz for 2 weeks and underwent urodynamic testing (UDS) to determine the optimal frequency based on the changes in urethral and detrusor pressures during micturition attempts with either stimulating frequency. The 1 Hz stimulation frequency reduced urethral pressure and increased detrusor pressure in all subjects more effectively than 30 Hz stimulation. Therefore, each subject used 1 Hz during the stimulation phase when he received weekly stimulation treatment for 16 weeks. During the follow-up phase, the subject received "sham" stimulation at <5% intensity in order to blind each subject to the change in stimulation treatment. The follow-up phase lasted 6 weeks or until each subject's urological improvements completely dissipated.

In the current study, we attempted to combine the benefits of neuromodulation of the spine described above and the ease of administration of transcutaneous magnetic stimulation to improve bladder function. Because of the close proximity of motor pools for lower extremity movements and motor pools for bladder and sphincter contractions, we hypothesized that we could use transcutaneous magnetic spinal cord stimulation (TMSCS) to modulate micturition in chronic SCI subjects to achieve sufficient voluntary voiding to reduce or eliminate the need for bladder catheterization.
Materials and Methods.
  Subject Selection:
  This was a pilot, prospective, interventional study with five enrolled subjects. All aspects of the study were approved by the UCLA IRB (IRB #14-000932). The inclusion criteria for the study were male age 18-75, a stable spinal cord injury between the C2-T8 levels present for greater than 1 year, and a documented history of neurogenic bladder requiring intermittent catheterization. Each subject was also required to have at least three prior urodynamic studies to confirm the diagnosis of neurogenic bladder with detrusor sphincter dyssynergia (DSD). Patients with a history of severe autonomic dysreflexia were excluded from the study because of safety concerns. Any patient who was ventilator dependent, abusing drugs, had musculoskeletal dysfunction (i.e., unstable fractures), cardiopulmonary diseases, active infections or ongoing depression requiring treatment was excluded from the study. Last, patients with a history of bladder botox injection or bladder/sphincter surgeries were excluded.
  Intervention (FIG. 10):
  Each study subject underwent baseline urodynamic testing (UDS) at the beginning of the study to confirm the diagnosis of a neurogenic bladder with DSD and establish baseline bladder functions. Next, each subject underwent two weeks of transcutaneous magnetic stimulation at both 1 Hz and 30 Hz frequency over the lumbar spine (described below). Each subject then underwent another UDS to determine the optimal stimulation frequency (the characteristics of optimal stimulation are defined below). Once the optimal frequency was established (and it turned out that 1 Hz was optimal in all five subjects), each subject subsequently received weekly transcutaneous lumbar spinal cord magnetic stimulation for a total of 16 weeks (described below). Each subject also received urodynamic testing once every four weeks to monitor progress and insure that bladder function was not further impaired. After the initial four-week stimulation period, each subject was asked to attempt volitional urination for 5-10 minutes prior to bladder catheterization. This 16-week period of transcutaneous magnetic stimulation of the spine constituted the bladder rehabilitation. Each subject was given a urine/stool specimen collection pan (Medline DYND36600H, Mundelein, Ill.) to record any volitional urinary output. They were instructed to record in the diary the output and residual urine in the bladder after every attempt to urinate voluntarily. Furthermore, they were asked to record any other changes that they may have noticed in the diary throughout the study period. Subjects were tracked after the completion of the 16 week bladder rehabilitation for six weeks or until their urologic improvements completely dissipated. During the follow-up period, sham transcutaneous magnetic stimulation (sham) was employed at reduced intensity (5%) that replicated the auditory, partial sensory, and mechanical cues of real stimulation. Each subject was instructed to continue to attempt to urinate voluntarily as he had during the stimulation phase, and each subject continued to keep a detailed urological lifestyle diary until the end of the follow-up phase.

The volitional micturition output and residual amount along with the number of catheterizations per day were recorded in the diary throughout the study period. The subjects were trained and the accuracy of their reporting was verified prior to start of the study. Each subject was also given an incontinence quality of life (iQOL) questionnaire to complete prior to the start of the study and at the end of the 16-week treatment stimulation. iQOL has been validated in multiple urological quality of life studies in patients with SCI (Jo et al. (2016) *Pain Physician*, 19: 373-380; Patrick et al. (1999) *Eur. Urol.*, 36: 427-435).
  Blinding:
  Subjects were blinded during the "sham" stimulations of the follow-up phase. Normally, subjects perceived a non-painful tingling sensation during stimulation, but were blinded to the exact stimulation parameters, as were the research staff members conducting the tests by using a research coil (with identical sham and treatment faces) which allows for experimenter and subject blinding, thus double-blinded study design. The staff member responsible for the control of the stimulator was not blinded as the stimulation parameters were manipulated during each session; however, this person did not interact with the subject (resided behind a curtain), and each staff member was instructed to follow the same script when administering the various tasks regardless of the particular stimulation values used.
  Urodynamic Testing:
  We employed a commercially available urodynamic machine (Laborie Aquarius® XT, Laborie International, Mississauga, ON, Canada) for all the urodynamic testing. Prior to the urodynamic testing, each subject's bladder was emptied by direct catheterization. The volume of urine was recorded. The patient was then placed in a supine position and a triple lumen catheter (TLC-7M, Laborie International, Mississauga, ON, Canada) was inserted. Two needle recording electrodes (1512A-M, Laborie International, Mississauga, ON, Canada) were inserted bilaterally into the perineum muscle approximately halfway between the base of the scrotum and anus and 1 cm lateral to the midline. An EMG grounding pad was placed on the knee joint. A rectal catheter (RPC-9, Laborie International, Mississauga, ON, Canada) was inserted to record abdominal pressure. The subject was then placed a left decubitus position. A condom catheter was used to collect any urine output, which was directed through a funnel into a graduated cylinder (DIS173, Laborie International, Mississauga, ON, Canada) on a scale (UROCAP IV, Laborie International, Mississauga, ON, Canada) to record the volume of urine produced and the stream velocity.
  Transcutaneous Magnetic Stimulation:
  A MagVenture Magnetic Stimulator (MagPro R30, Atlanta, Ga.) with research an active/placebo FIG. 8 research coil (Cool-B65 A/P Coil) was used for all transcutaneous magnetic stimulation sessions. The spinous processes of the lower vertebrae in each subject were palpated, and thoracic 11 to lumbar 4 vertebrae were marked, and the coil was centered along the midline at the L1 vertebral level during the stimulation. We used monophasic, single pulse, continuous, magnetic stimulation with pulse duration of 250 ps. Each stimulation session consisted of three 4-min continuous stimulation periods with a 30 second break between each stimulation period for a total of 13 minutes (a total of 12 minutes of stimulation plus 1 minute of breaks). For the first two weeks, each subject initially underwent stimulation at 1 Hz and 30 Hz frequencies (week one: 1 Hz/30 Hz/1 Hz, and week two: 30 Hz/1 Hz/30 Hz) until the optimal frequency was determined for the patient at the first follow up UDS after the $2^{nd}$ week of stimulation. Changes in urethral and detrusor pressures during micturition attempts were measured during both low frequency stimulation (1 Hz) and high frequency stimulation (30 Hz). The stimulation frequency that resulted in the combination of increased detrusor pressure and decreased urethral pressure during attempted micturition (hence, promoting bladder emptying) was selected as optimal. The intensity of stimulation was selected based on the maximal tolerable intensity for each subject (usually around 40-50% of the maximal field strength of 2 Tesla). Once the optimal frequency was determined, all subjects received the optimal stimulation frequency only for the remaining 16-week bladder rehabilitation sessions.

Electrophysiology:

At the end of the study, the following electrophysiological data were obtained on each subject prior to stimulation, during and after low frequency (1 Hz) and high frequency (30 Hz) transcutaneous magnetic stimulation: bulbocavernosus reflex (BCR), electromyography (EMG) and spinal evoked potentials (SEP) bilaterally in the pelvic floor and in the vastus lateralis, gastrocnemius, gluteus and hamstring muscles.

Pelvic floor EMGs were obtained using needle electrodes (Laborie 1512A-M, Laborie International, Mississauga, ON, Canada). All other muscle EMGs were obtained with 1 inch surface pad electrodes (MultiBioSensors, El Paso, Tex.).

The BCR was obtained by using ring stimulating electrodes (Cadwell 302243-200, Cadwell Industries, Kennewick, Wash.) that were stimulated with a monophasic electric pulse at 1.5 Hz, pulse width 0.2 ms and intensity at three times the sensory threshold (or 35 mA if the subject had no sensation). 100 pulses were given for each BCR session.

Recording, amplification and digitization of all data were done using and RZ2 amplifier and a PZ5-32 TDT digitizer (Tucker Davis Technologies, Alachua, Fla.) with a 60 Hz notch filter and band pass filtering to exclude frequencies<3 Hz and >200 Hz.

Data Analysis:

All electrophysiological data from the TDT system (Tucker Davis Technologies, Alachua, Fla.) were exported to a personal computer and analyzed in MatLab (Matlab2015b, MathWorks, Natick, Mass.). The BCR amplitudes and latency were calculated for every single electrical pudendal stimulation. SEP (if present) were identified in the continuous recording of lower extremity EMGs.

Urodynamic data were exported from the Laborie system to a personal computer and analyzed in Microsoft Excel (Excel2010, Microsoft, Redmond, Wash.). The changes in urethral pressure (Pura) and detrussor pressure (Pdet) were measured and compared during baseline and during attempted micturition.

Statistical significance was assessed with Analysis of Variance (ANOVA) and paired Student's T-test using R 3.25 (www.r-project.org) and Graphpad Prism (Graphpad Software, La Jolla, Calif.), respectively.

Results.

Figure 11:
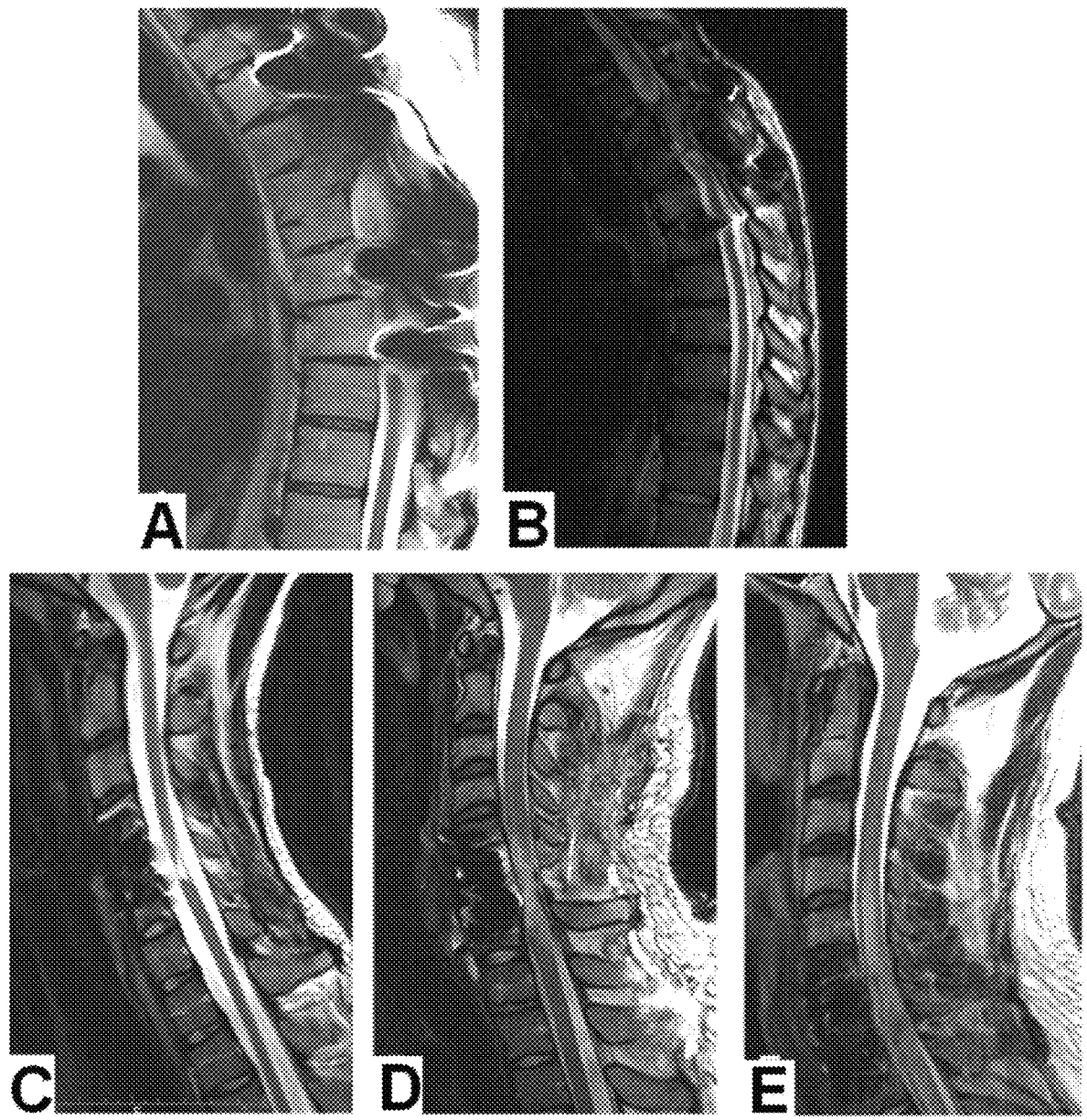
FIG. 11, panels A-E shows T2-weighted MRI imaging showing the degree of SCI in all five subjects enrolled in the study.

The demographic information for all five enrolled subjects is shown in Table 1. The magnetic resonance images (MRI) indicating the level and extent of SCI for each of the five subjects are shown in FIG. 11. The average chronicity of injury was 8.8±7.5 years. None of the five subjects had been able to void voluntarily since the time of injury (four to 22 years) as shown in at least three prior urodynamic studies. Two subjects (C & D) were taking low dose anti-cholinergic drugs for detrusor hyperactivity and bladder spasms. The anti-cholinergic medications were tapered off at the end of the assessment phase. All five subjects remained off any forms of anti-cholinergic medicines at the end of the 16 weeks of bladder rehabilitations and experienced no significant bladder spasms or enuresis.

TABLE 1

Demographic information on all five study subjects; the length of stimulation until volitional micturition is the number of weeks of stimulation necessary before each subject could initiate voluntary urination; decay/length of the effect duration is the number of weeks after the termination of the magnetic stimulation that each subject was able to void any amount voluntarily.

| Subject # | Gender | Age | Injury level | ASIA Grade | Injury Year | Mechanism of Injury | Length of stimulation until volitional micturation | Decay/Length of the effect duration (weeks) |
|---|---|---|---|---|---|---|---|---|
| A | M | 42 | T4 | A | 1994 | MVA | 4 | 4 |
| B | M | 43 | T4 | A | 2012 | Wrestling | 6 | 3 |
| C | M | 22 | C5 | B | 2009 | Football | 5 | 3 |
| D | M | 25 | C6 | B | 2009 | MVA | 5 | 4 |
| E | M | 23 | C7 | A | 2012 | MVA | 8 | 2 |

All five subjects achieved at least some volitional urination following 16 weeks of bladder rehabilitation. No one achieved any volitional urination until at least 4 weeks (12 min×1 Hz=720 pulses/week×4 weeks=2880 pulses) after the initiation of the stimulation. The average length of stimulation until the initiation of volitional micturition was 5.6±1.5 weeks. The average time that volitional micturition was maintained after the termination of stimulation was 3.2±0.8 weeks.

After 16 sessions of weekly transcutaneous stimulation, all five subjects achieved volitional micturition with an average flow stream velocity of 9.3±1.1 ml/s. Daily clean intermittent catheterization (CIC) decreased from 6.6 times per day at baseline to 2.4 times per day at the conclusion of the 16 week bladder rehabilitation. Bladder capacity as measured during UDS increased from 244 to 404 ml. While all five subjects had improvements in urinary functions and were able to achieve volitional micturition, their response to the transcutaneous stimulations varied (A>D>B=C>E). This variation did not appear to be the result of difference in their ASIA classification. (Table 2).

Figure 15:
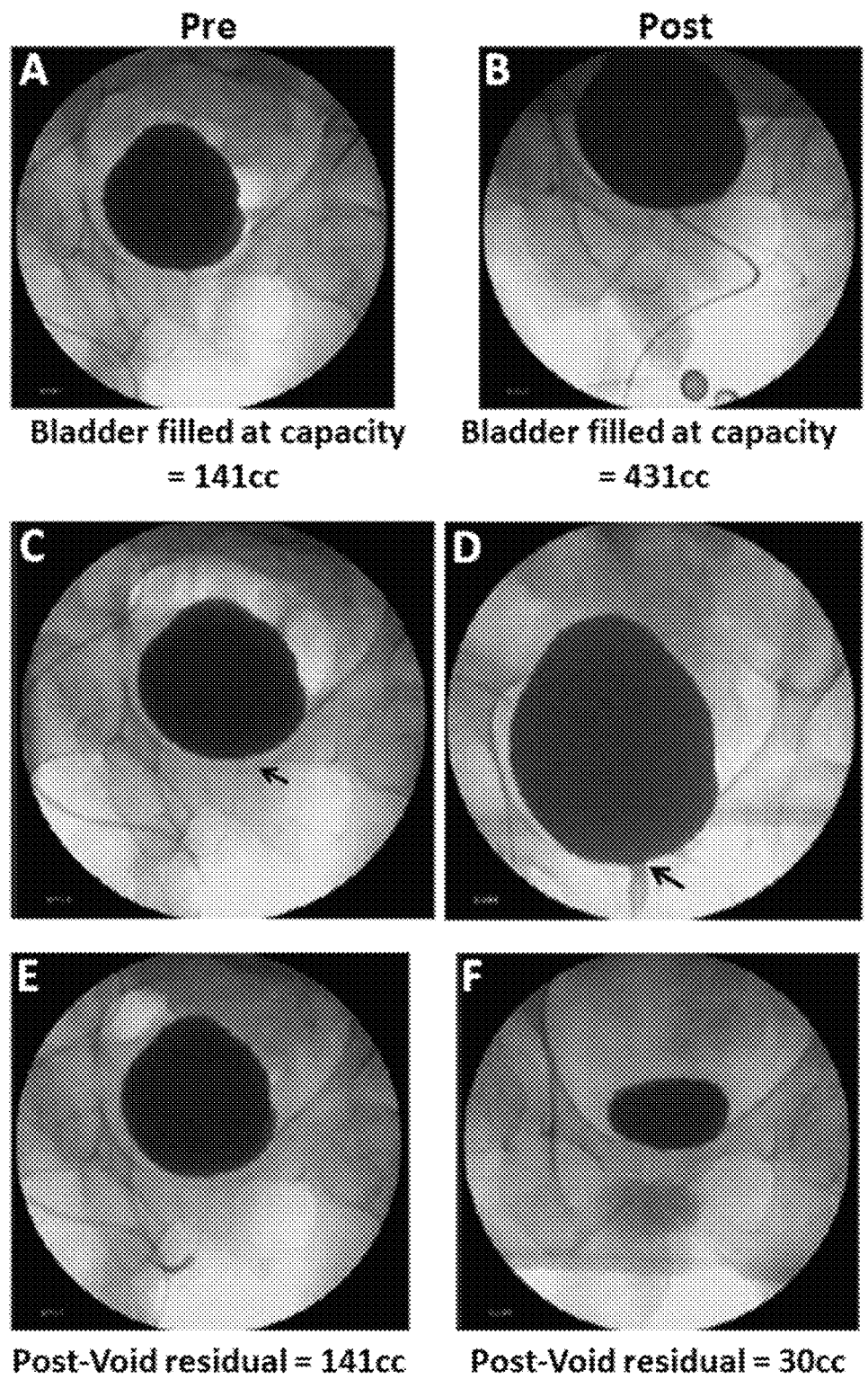
FIG. 15, panels A-F, shows an example of video urodynamics from patient A. Panels A, C, and E=pre-stimulation baseline. Panels B, D, and F=16-week post-transcutaneous magnetic stimulation. Panels A and B show the bladder capacity, notice the significant increase in the capacity after bladder rehabilitation. Panels C and D panels show the initiation of volitional voiding and opening the bladder neck (black arrow) on the right middle panel. Panels E and F show the post-void residuals for each UDS.

It is important to note that improvements in urinary function were not instantaneous. Rather, progressive improvement became apparent over the course of the study. This pattern of improvement is illustrated in FIG. 15. When we looked at the urethral and bladder pressures during volitional urination attempts over the 16-week course of rehabilitation, we saw that initially there was little (if any) sustained bladder contraction and persistently elevated ure-

TABLE 2

Urinary variables for all five study subjects. All five subjects achieved voluntary micturition; CIC = clean intermittent catheterization; pre = before the 16 week bladder rehabilitation; post = at the conclusion of the 16 week bladder rehabilitation; Ave = average; SD = standard deviation.

| Subject | CIC/day Pre | CIC/day Post | Volitional Void (Y/N) | Stream Velocity (ml/s) | Bladder Capacity Pre (ml) | Bladder Capacity Post (ml) | Daily Voiding Volume Post (ml) |
|---|---|---|---|---|---|---|---|
| A | 9 | 0 | Y | 10 | 141 | 431 | 2000 |
| B | 6 | 3 | Y | 10 | 238 | 462 | 700 |
| C | 6 | 3 | Y | 10 | 270 | 351 | 800 |
| D | 6 | 1 | Y | 8 | 215 | 325 | 1800 |
| E | 6 | 5 | Y | 8 | 354 | 452 | 300 |
| Ave | 6.6 | 2.4 | — | 9.3 | 244 | 404 | 1120 |
| SD | 1.3 | 1.9 | — | 1.1 | 78 | 62 | 740 |

Figure 12:
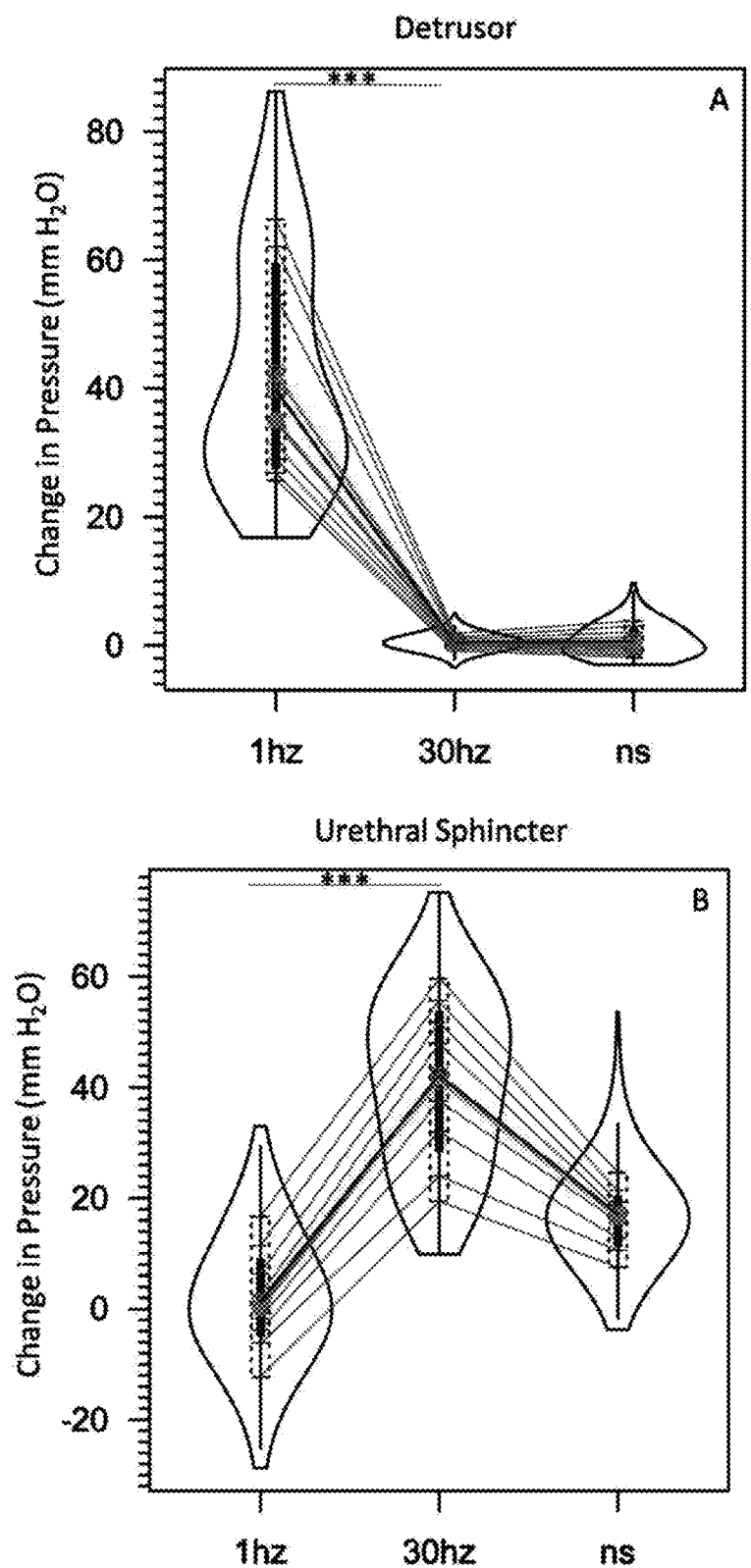
FIG. 12, panels A and B show violin plots of change in pressure during urination attempt (mm $H_2O$), by stimulation condition for detrusor and urethral sphincters obtained at the conclusion the assessment phase. Each violin shows mean and median (heavy horizontal lines), standard deviation (heavy vertical bars) and deciles (in light grey) using a kernel density estimator. For labeled "Detrusor" (panel A) the 1 Hz condition resulted in a mean pressure change of 42.3±17.3 mm $H_2O$, while the no-stimulation (ns) and the 30 Hz conditions showed mean pressure changes of 0.5±1.1 and 0.8±2.4 mm H2O, respectively. For "Urethral sphincter" (panel B), the 1 Hz condition resulted in a mean pressure change of 1.4±10.9 mm H2O while in the no-stimulation and 30 Hz conditions, the mean pressure changes were 41.1±15.0 and 16.7±7.8 mm $H_2O$, respectively. Analyses of variance (ANOVA) and Tukey HSD post-hoc testing were used to examine the differences between conditions in each of the two measures. In both instances, 1 Hz condition differed from both the non-stimulated condition and the 30 Hz condition ($p<0.0001$), but the latter two did not differ from one another. ***=$p<0.0001$.

Analysis of the urethral (Pura) and detrusor pressures (Pdet) obtained during urodynamic testing during volitional micturition attempts revealed a statistically significant difference between high and low frequency transcutaneous magnetic stimulation protocols (FIG. 12). In all five individuals, stimulation at a low frequency resulted in sustained increases in detrusor pressure and minimal/no effect on the urethral pressure. Stimulation at high frequency, however, had the opposite effect: urethral pressure increased significantly, but detrusor pressure was not modified by 30 Hz stimulation. Because increasing bladder pressure while simultaneously decreasing urethral pressure simulates normal micturition, these differences allowed us to narrow the therapeutic stimulation to the low frequency setting only in all five subjects.

Figure 13:
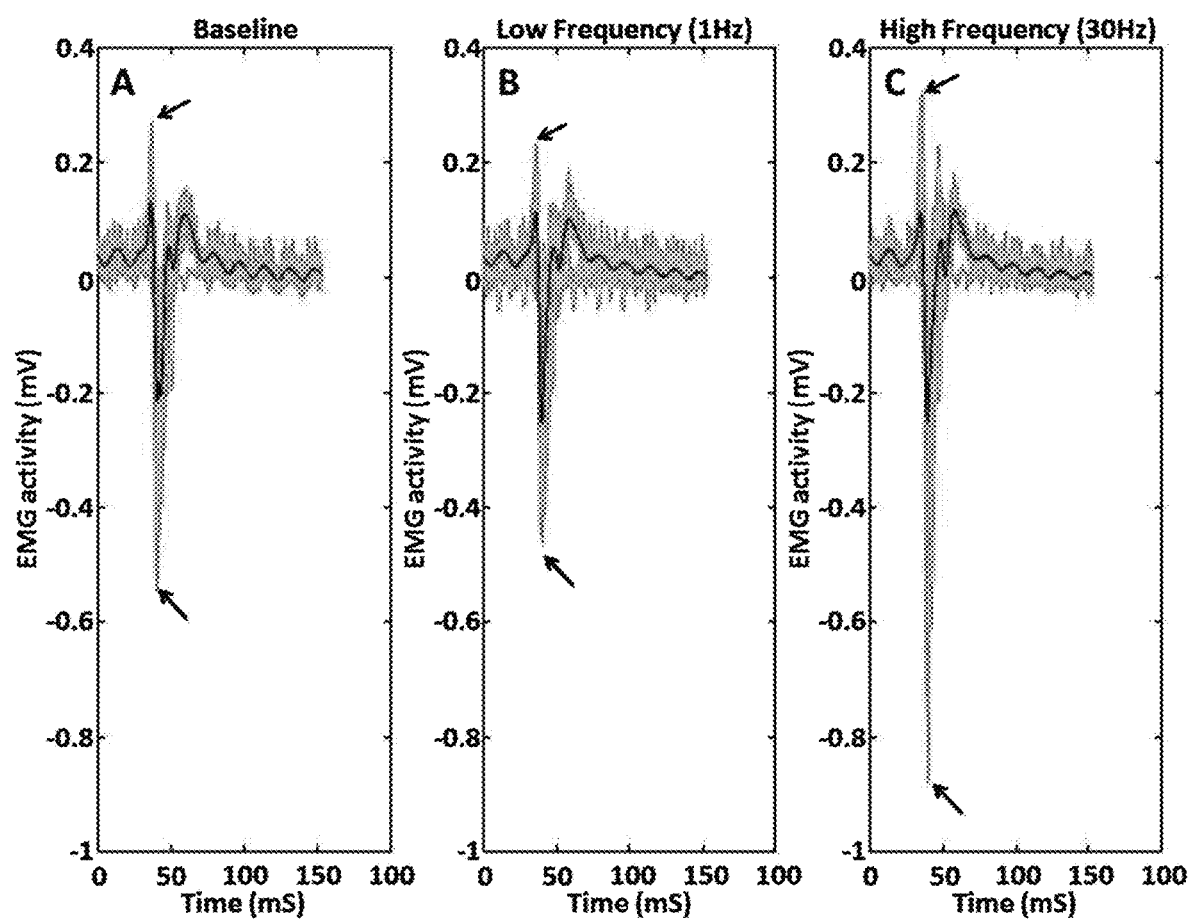
FIG. 13, panels A-D shows the change in BCR amplitude, which is measured from the perineal muscle EMG during low frequency (1 Hz) and high frequency (30 Hz) transcutaneous magnetic stimulation of the spinal cord at the end of the assessment phase. Panels A, B, and C show an example of the BCR EMG activity from subject C at non-stimulation baseline (panel A), after low frequency stimulation (panel B) and after high frequency stimulation (panel C) respectively; gray shading=individual electrical recordings; dark line=average. Panel D=amplitude changes in all five subjects. Note a significantly greater reduction of BCR amplitude after low frequency stimulation when compared to high frequency stimulation. Student's t-test: ***=$p<0.0001$, N=100. BCR=bulbocavernosus reflex.

The bulbocavernosus reflex (BCR) is dµVisinhibited and pathologically hyperactive after SCI, like other spinal motor reflexes below the level of SCI. Low frequency transcutaneous magnetic stimulation significantly reduced the BCR amplitude in all five subjects. In contrast, high frequency stimulation resulted in either further increased amplitude or no significant change (FIG. 13). The average BCR latency was $35.2 \pm 5.3$ ms, which is similar to the latency of the BCR in normal individuals (Granata et al. (2013) Funct. Neurol., 28: 293-295). The baseline amplitude, however, ranged from 490-3800 ˆV; amplitudes that are about 10-100 times greater than those of normal individuals Granata et al. (2013) Funct. Neurol., 28: 293-295). During low frequency stimulation, the BCR amplitude was significantly decreased to between 440-3100 ˆV compared to the unstimulated baseline (an average reduction of 28%, $p<0.0001$). High frequency stimulation did not alter the BCR amplitude from baseline, which ranged between 475-3700 µV ($p=0.61$).

Figure 14:
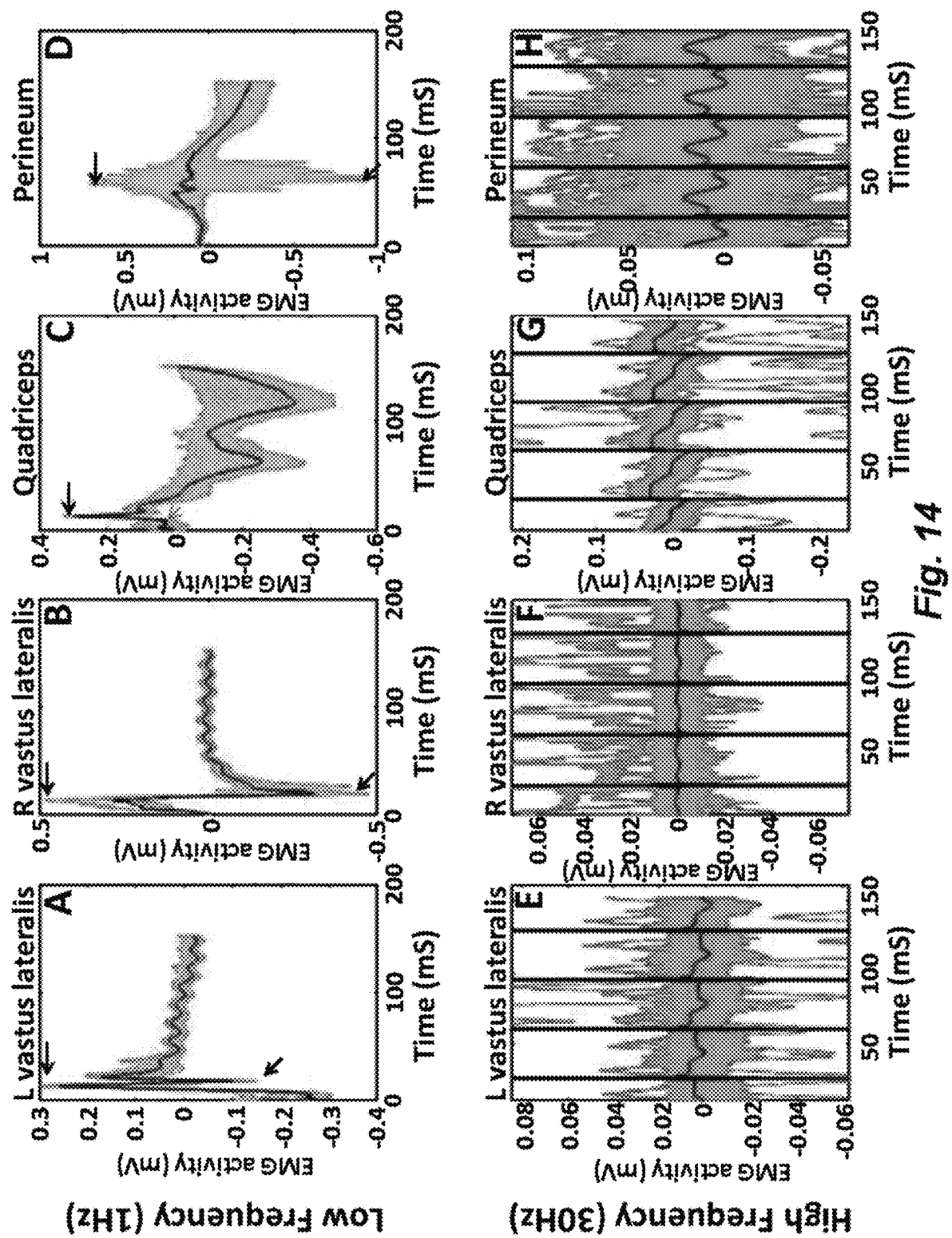
FIG. 14, panels A-H, shows EMG recording from various lower extremity muscle groups (vastus lateralis, quadriceps and perineum) measured during transcutaneous magnetic spinal cord stimulation at low frequency (1 Hz, upper panel) or high frequency (30 Hz, lower panel) obtained at the end of the assessment phase. The stimulator was centered at L1 vertebrate level. The first stimulation pulse occurred 5 ms before the start of EMG capturing. During 30 Hz stimulation (panels E-H), there were 4 additional stimulation pulses that were captured during the 150 ms EMG window. These are indicated by the vertical black bars. For panels A-D, gray shading=individual electrical recordings, dark line=average over all trials. For panels E-H, gray shading=individual electrical recordings, black line=average over all trials. Note the evoked potentials recorded during low frequency stimulation (panels A-D) around 20-25 mV. No such evoked potentials were noted with high frequency stimulations (panels E-H) even though the y-axis scale has been expanded to try to detect evoked potentials. N=240.
Figure 16:
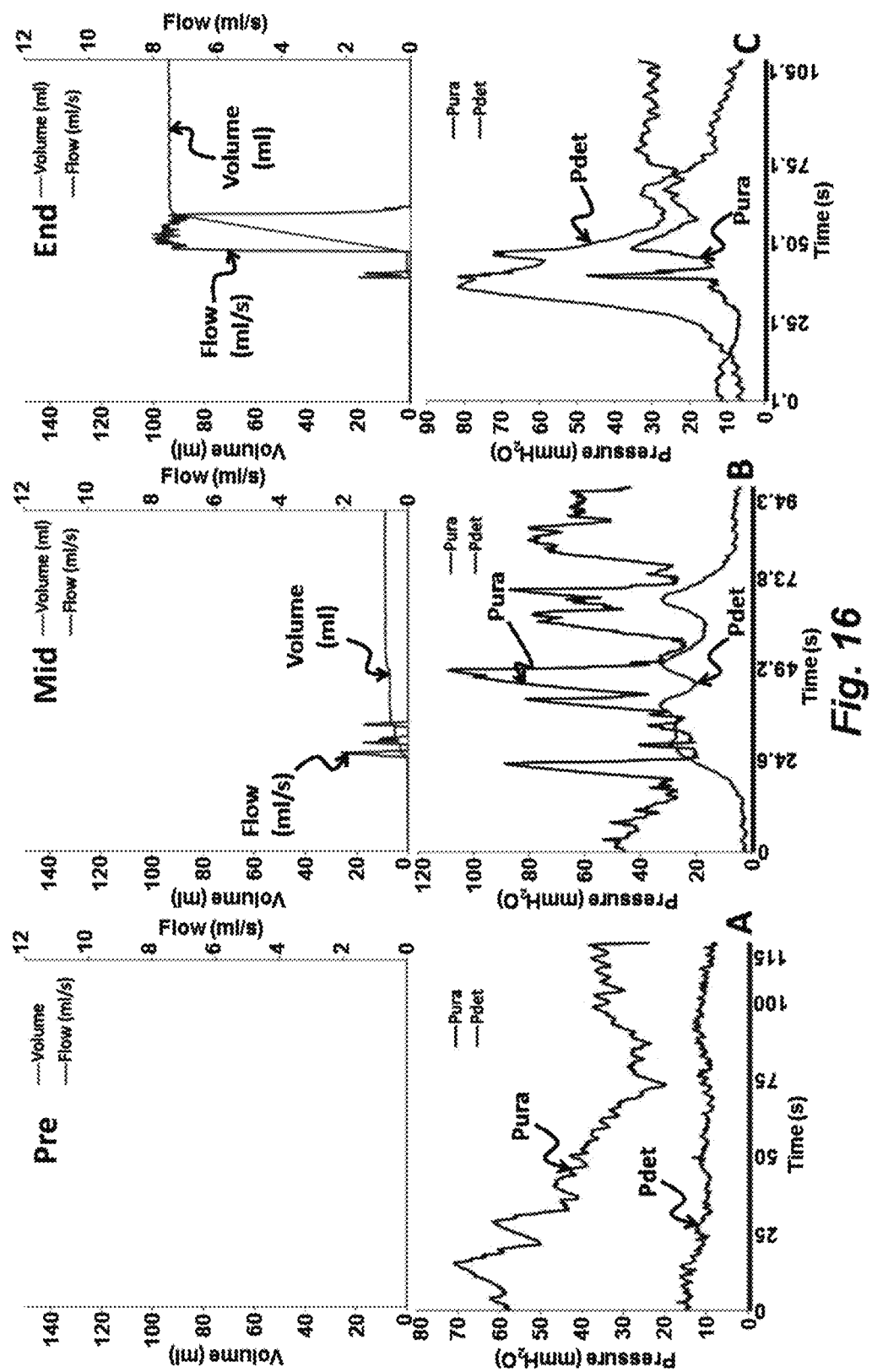
FIG. 16, panels A-C, shows an example of urodynamic testing for subject B at three stages of the 16-week stimulation period. Top panel=urine flow; bottom panel=urodynamic pressure monitoring. Panel A) Pre=baseline/before stimulation; Panel B) Mid=after 6 weeks of stimulation; Panel C) End=after 16 weeks of stimulation. Notice the urethral (Pura) and detrusor pressures (Pdet) crossed during volitional micturition (lower panel C), at which point urine flow was achieved.
Figure 17:
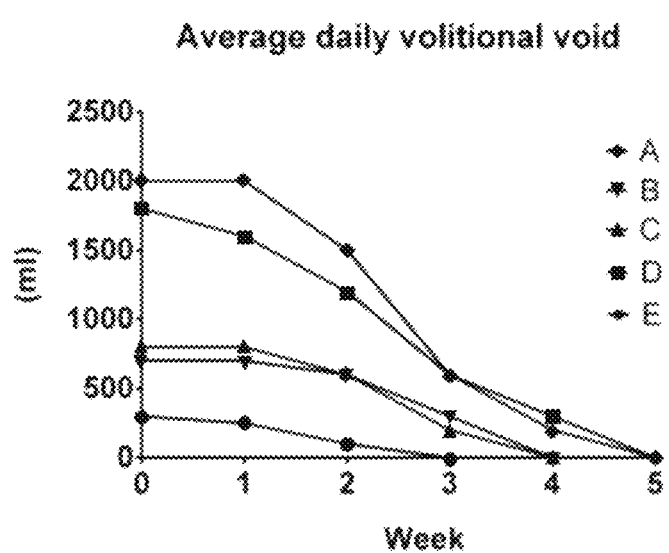
FIG. 17 shows the average daily volitional micturition volume for all five subjects after the termination of effective stimulation (Week 0). Note that the effect of previous lumbar magnetic stimulation lasted for about 1-2 weeks after the termination of transcutaneous magnetic stimulation, then the average daily volitional voiding amount declined rapidly back to the baseline (unable to void voluntarily).

Interestingly, during low frequency transcutaneous magnetic stimulation, we were also able to generate spinal cord evoked potentials in selected lower extremity muscle groups (quadriceps femoris and vastus lateralis); whereas we were unable to detect any spinal evoked potentials at higher stimulation frequencies (FIG. 14).

thral pressures. Upon completion of some (>4 weeks) of the stimulations sequences, the subjects became better able to generate more sustained bladder contractions; however, they still had persistent detrusor sphincter dyssynergia (DSD) as evident by further elevation of urethral pressures. At the end of the 16 week rehabilitation period, the subjects showed sustained bladder contractions with high detrusor pressures and reduced urethral pressures, which stayed below the bladder pressure during the entire course of urination. This resulted in higher urine flow velocity and significantly higher urination volume at the end of the rehabilitation period (FIG. 16.) The improvement following stimulation was not permanent. The effects were maintained for about 2 weeks after the study and then slowly tapered off. No subject maintained the urological functional improvements five weeks after the last stimulation. Follow up diary entries revealed that the ability to void voluntarily rapidly decayed in all five subjects after the cessation of effective stimulation (FIG. 17).

Figure 18:
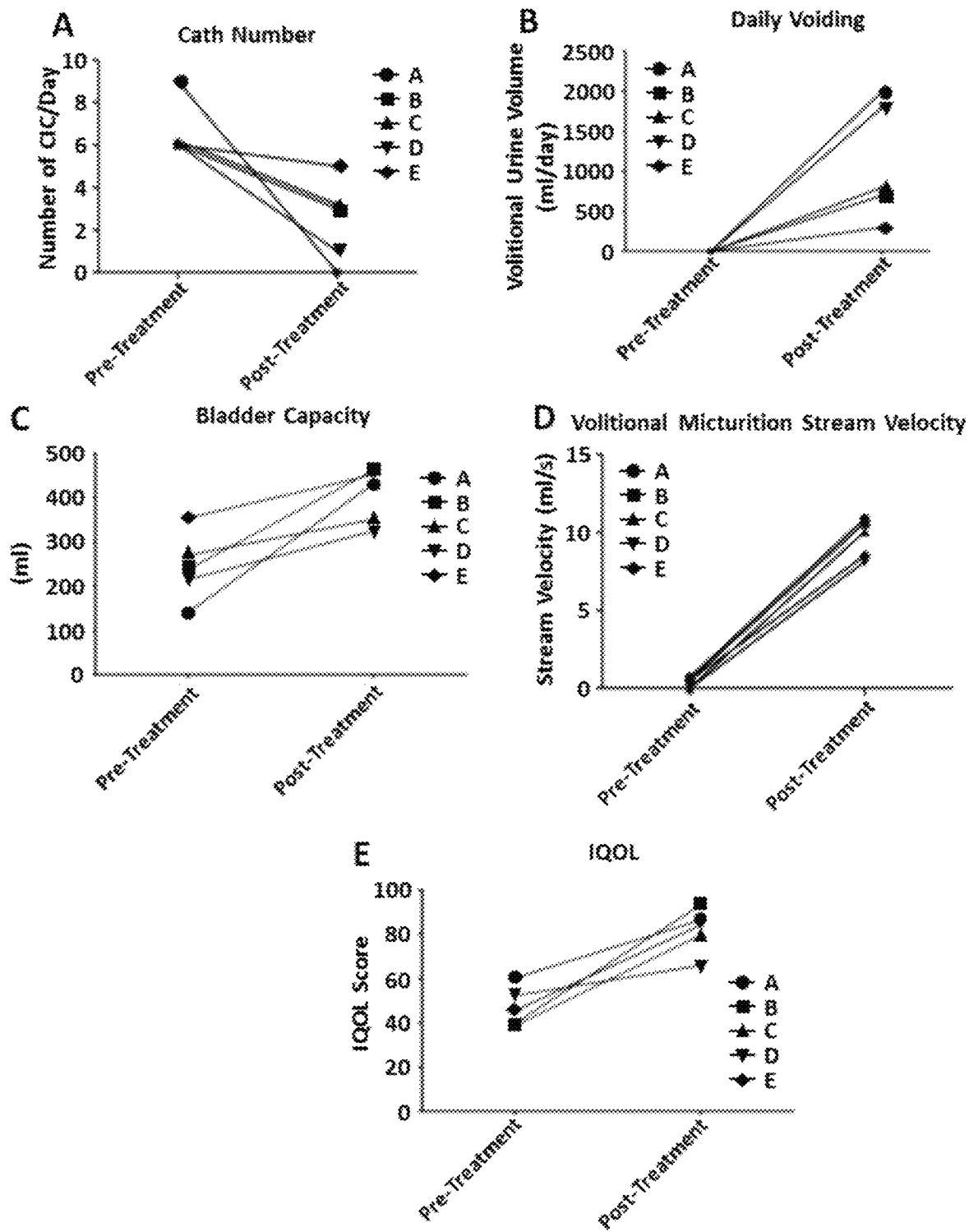
FIG. 18, panels A-E, shows a summary of urological functions for all five subjects; all changes were statistically significant when tested with paired t-tests. Panel A) The number of necessary catheterizations (CIC) per day decreased for all five individuals from 6.6±1.3 to 2.4±1.9, p=0.04. Panel B) The daily volitional voiding amount increased in all five individuals from 0±0 ml to 1120±740 ml, p=0.03. Panel C) The bladder capacity increased from 243±78 ml to 404±62 ml, p=0.02. Panel D) The stream velocity increased for all five individuals from 0±0 ml/s to 9.3±1.1 ml/s, p<0.001. Panel E) The quality of life as measured by iQOL questionnaire increased from 47±9 to 82±10, p=0.007.

At the end of 16 weeks of transcutaneous magnetic stimulation, the subjects needed fewer CIC per day (from 6.6/day at baseline to 2.4/day, $p=0.04$); were able to volitionally urinate (from 0 cc/day to 1120 cc/day, $p=0.03$); had an increased bladder capacity (from 244 ml to 404 ml, $p=0.02$); were able to generate significant stream velocities (from 0 cc/sec to 9.3 cc/sec, $p<0.001$) and enjoyed a much higher quality of life as measured by i-QOL (47 to 82, $p=0.007$, FIG. 18).

We observed no significant adverse events including no episodes of autonomic dysreflexia or priapism. In addition, subjects reported in the diaries increased erection frequency, intensity and duration, and improved bowel function. Two of the subjects were able to have daily bowel movements without any form of assistance; two subjects were able to have bowel movements with minimal assistance; and one subject noted no change in bowel function. All of the subjects reported improved posture reflected by improved ease of lateral transfer and increased duration of standing with and without assistance that correlated precisely with improved volitional bladder control. This was noted both by the subjects in their diaries and by the physical therapists during each subject's motor rehabilitation sessions. The only negative effect reported by the subjects was increased lower extremity spasms; however, the spasms remained tolerable.

Discussion

Micturition, particularly voluntary micturition, requires complex, orchestrated neuromuscular control of the urinary bladder by sensory, motor and autonomic systems. In normal individuals, this control is achieved through fronto-pontine-spinal cord projections. The parasympathetic nervous system originates from the S2-4 spinal cord level and reaches the bladder via pelvic splanchnic nerves. When activated, these nerves facilitate detrusor contraction and inhibit urethral sphincter contraction. Sympathetic control of the bladder originates in the intermediolateral cell column from T11-L2 and reaches the bladder through synapses in prevertebral ganglia in the inferior mesenteric and hypogastric plexi, which project to the bladder via hypogastric nerves and inhibit bladder contraction and stimulate urethral sphincter activity. Somatic innervation of the external (striated muscle) sphincter originates from Onuf's nucleus in the ventral horn of the sacral spinal cord and allows voluntary micturition when it is relaxed or inhibited. In spinal cord injured individuals, however, there is a lack of coordination among the parasympathetic, sympathetic and somatic nerve activities controlling bladder function. As a consequence, bladder pressure is elevated, and the bladder cannot be completely emptied so that post-void residuals are increased. Overtime, the constantly elevated bladder pressure results in vesicular hypertrophy and decreased bladder capacity. This often results in a need for an increased number of catheterizations each day, which increases the risk and frequency of infection and traumatic injury to the urethra. Not surprisingly, lower urinary tract dysfunction is consistently ranked as the number one negative symptom in many quality of life surveys among spinal cord injured patients (Simpson et al. (2012) *J. Neurotrauma*, 29: 1548-1555).

Recently, it has been observed that isolated regions of lumbosacral spinal cord contain circuitries that are capable of carrying out complex motor activities (Lu et al. (2015) *Front. Mol. Neurosci.* 8: 25; Alaynick et al. (2011) *Cell* 146: 178-178.e171; Sugaya et al. (1994) *Am. J. Physiol.*, 266: R658-667). Furthermore, it is clear that the spinal cord injury in most ASIA A SCI subjects is not anatomically complete, and the spinal circuitries usually remain intact, especially those below the level of the spinal cord injury. In both animal and human subjects with chronic paralysis from SCI, motor movements have improved after invasive, epidural, electrical stimulations (Harkema et al. (2011) *Lancet*, 377: 1938-1947; Angeli et al. (2014) *Brain*, 137: 1394-1409). Multiple studies have also employed TMS, which is approved by the Food and Drug Administration (FDA) for treatment of migraine, and has been used to treat stroke and SCI patients for neuropathic pain, muscular spasticity and somatomotor training (Nardone et al. (2016) *Brain Res. Bull.*, 124: 144-149; Nardone et al. (2016) *Spinal Cord, doi:* 10.1038/sc.2016.87; Awad et al. (2015) *World Neurosurg.* 83: 232-235). Electromagnetic peripheral nerve modulation has even been used to attenuate visceral sensitivity in patients with irritable bowel syndrome (Algladi et al. (2015) *Pain*, 156: 1348-1356). To date however, there is no report using magnetic stimulation to modulate spinal cord functions in human subjects. In this study, we hypothesized that the spinal micturition circuitry remains intact in SCI subjects, and since these circuits are semiautonomous, we would be able to leverage the patterned muscle activities controlled by these circuits and activate or modulate them using transcutaneous magnetic stimulation over the lumbar spine. We demonstrated that the application of completely non-invasive transcutaneous magnetic stimulation at thoracolumbar level restored bladder function in individuals with chronic SCI. These early results are encouraging. All five subjects were able to achieve volitional micturition. Four out of five subjects (80%) were able to decrease the number of CIC required each day by at least 50%. One subject (20%) was able to void normally without any catheterization while another subject (20%) only needed one catheterization each day.

There have been other attempts to restore urination in SCI patients, specifically using multiple peripheral nerve stimulations. The targets were the pudendal nerve, pelvic nerve, hypogastric nerve and tibial nerve (Schneider et al. (2015) *Eur. Urol.*, 68: 859-867; Kennelly et al. (2011) *J. Spinal Cord Med.* 34: 315-321; Burks et al. (2010) *Urol. Clin. North Am.* 37(4): 559-565; Spinelli et al. (2005) *Neurol. Urodynam.* 24: 305-309). Stimulation of these nerves did not consistently improve bladder function in patients with chronic SCI (Schurch et al. (2003) *World J. Urol.*, 20: 319-322). Furthermore, sacral nerve modulation requires electrode implantation, which is invasive and risky (Bielefeldt (2016) *World J Gastrointest Pharmacol Ther.* 7(2): 294-305; Zeiton et al. (2016) *Int. J. Colorectal Dis.*, 31: 1005-1010; Eldabe, et al. (2015) *Pain Med.* 17(2): 325-336). Transcutaneous magnetic stimulation differs in that it is non-invasive and painless in the SCI patients. In addition, our findings indicate that transcutaneous magnetic stimulation is more consistent and more effective than epidural stimulation of selected peripheral nerves.

The transcutaneous magnetic stimulation that we employed appears to allow volitional activation of a sequence or pattern of parasympathetic activation and sympathetic and somatic muscle inhibition. While the precise mechanism remains unknown, the coordinated activity of detrusor and sphincter muscles suggests to us that the magnetic stimulation works by activating central pattern generating circuits within the lumbosacral spinal cord and does not rely on just the activation of the peripheral nerves alone. This central pattern generator seems to balance and coordinate parasympathetic, sympathetic and somatic motor activity to enhance micturition. This hypothesis receives support from the finding that transcutaneous magnetic stimulation at 1 Hz resulted in micturition, which decreased urethral pressure and increased detrusor pressure, as opposed to the enhanced storage of urine within the bladder that occurred during stimulation at 30 Hz, which increased urethral pressure and decreased detrusor pressure. The different stimulation frequencies seemed to elicit different bladder behaviors as if different CPGs or different aspects of a micturition CPG were activated. Consistent with such an idea, low frequency magnetic peripheral nerve stimulation of the pudendal or sacral nerves, which would not activate a micturition CPG, but would tend to increase urethral pressures without a coordinated effect on detrusor pressure, has been used to treat incontinence and overactive bladder (Lim et al. (2015) *Trials* 16: 279; Schober et al. (2015) *J. Urol.*, 194: 1721-1726). Furthermore, the apparent requirement for a cumulative effect of magnetic spinal cord stimulation on the emergence of effective bladder function (no subject experienced symptomatic micturition improvement until at least 4 weeks after the onset of the bladder rehabilitation) also supports our theory of activating a CPG and not just activation of peripheral nerves or direct activation of motor neurons. This cumulative effect is also consistent with our earlier findings using epidural electric stimulations in motor function restoration in which an average of 3-5 sessions/weeks were required before the improvements in motor functions were seen (Lu et al. (2016) *Neurorehabil. Neural Rep.* 30(10): 951-962).

The modifications in the BCR during magnetic stimulation also support the hypothesis that we accessed the micturition spinal circuitry rather than direct motor neuron stimulation, as modifications of a polysynaptic reflex such as BCR require more than simple motor neuron stimulation. BCR amplitudes for our subjects at baseline were 10 to 100 times greater than those in normal individuals. This observation suggests that SCI subjects have decreased supraspinal inhibition of the BCR polysynaptic reflex. During low frequency stimulation, the amplitude of the BCR decreased, and this implied greater inhibition of the BCR polysynaptic reflex (likely via spinal circuitry). However, high frequency stimulation did not decrease the BCR amplitude. (FIG. 13) We hypothesize that the decrease in BCR amplitudes in chronic SCI during low frequency magnetic stimulation may be the result of decreased spinal motor neuron hyperactivity, as if magnetic stimulation had restored or permitted more effective spinal motor neuron inhibition.

We also observed significantly different effects on bladder function during magnetic stimulation with low frequency (1 Hz) or high frequency (30 Hz) stimulation. When low frequency stimulation (1 Hz) was present during urination attempts, we observed an increase in bladder contraction and simultaneously a minimal change or an inhibition of urethral sphincter contraction, which resulted in effective micturition. Conversely, we observed a minimal effect on bladder contractions and an increase in urethral sphincter contractions during urination attempts during high frequency stimulation (30 Hz), and as a consequence, increased urine storage (FIG. 12).

There were also differences in lower extremity muscle group EMG activities during low (1 Hz) and high frequency (30 Hz) stimulations. We observed evoked potentials in multiple lower extremity muscle groups during 1 Hz stimulation, but no evoked EMG activity during 30 Hz stimulations (FIG. 14). The evoked potentials during low frequency stimulation are evidence that spinal motor circuits are intact, and also evidence that the bladder responses were not secondary to peripheral nerve stimulation or direct muscle stimulation as those would not result in evoked potentials. We hypothesize that the improved coordination among muscles used during voiding during low frequency magnetic stimulation may be the result of decreased external sphincter motor pool hyperactivity or may reflect modulation of supraspinal inputs such that the supraspinal signal(s) initiating micturition were better able to effect volitional urination.

Other possible mechanisms whereby magnetic stimulation may alter neuronal function include modulation of the spinal interneurons via dorsal root ganglion (DRG) or dorsal column stimulation, which is a putative mechanism of action for epidural spinal cord stimulation (Ramasubbu et al. (2013) *Curr. Pain Headache Rep.*, 17: 315). Transcutaneous magnetic stimulation may also modulate responses within the sympathetic chain and sacral parasympathetic centers and facilitate the process of micturition. Furthermore, it seems likely that our repeat transcutaneous magnetic stimulation resulted in remodeling of the spinal circuitry. This seems likely to us in that the effect of lumbar transcutaneous magnetic stimulation was not immediately effective and the benefit decayed slowly—suggesting that some relatively slow neuronal or circuit remodeling was occurring. This phenomenon is well recognized in TMS studies, specifically with low frequency (1 Hz) stimulation (O'Shea et al. (2007) *Neuron*, 54: 479-490; Lee et al. (2003) *J. Neurosci.*, 23: 5308-5318).

Our subjects were able to urinate voluntarily in between treatment sessions when magnetic stimulation was not present. Therefore, we believe that the magnetic stimulation enabled the residual connections between the supraspinal centers and the spinal urinary CPGs to initiate and control volitional micturition. Our findings suggest that neural pathways between a lumbosacral micturition center and supraspinal micturition center(s) that were not effective after injury can be enabled following several sessions of stimulation—bladder rehabilitation seemed to enhance the function of residual volitional circuits since the improvements in bladder function did not require active magnetic stimulation at the time of volitional activation of bladder emptying. We believe that transcutaneous magnetic stimulation raised the activation state (or reduced inhibition) of the micturition circuit, which is consistent with our previous findings using epidural stimulation to enhance motor function recovery (Lu et al. (2016) *Neurorehabil. Neural Repair.* 30(10): 951-962). We hypothesize that in the presence of magnetic stimulation; the dormant or inadequate volitional pathways to spinal cord CPGs were enabled and sufficiently plastic to be susceptible to neuromodulation so that volitional control of semiautonomous bladder function was relearned or recovered even when magnetic stimulation was not present. Moreover, once this supraspinal to spinal communication had been activated, it remained enabled so long as the subject received some minimal amount of stimulation during each weekly treatment session. These results and our previous study of locomotion (Id.) provide two examples of the capacity of neuromodulation of spinal circuits to enable volitional control of motor functions below the level of SCI.

The benefits of transcutaneous magnetic stimulation were not permanent. All five subjects lost their micturition ability soon after the termination of transcutaneous magnetic stimulation (Table 1 and FIG. 17). We hypothesize that the magnetic stimulation resulted in activation of the existing/preserved spinal micturition circuitry, but this state of heightened susceptibility to volitional activation did not seem to persist. It is, apparently, insufficient simply to activate bladder emptying voluntarily after transcutaneous magnetic stimulation of the spine ceased—some aspect of magnetic stimulation of the lumbar spine was necessary between periods of volitional bladder emptying to maintain a heightened activation state within the lumbar micturition circuit(s). The heightened activation state is likely to reflect some aspect of neuronal plasticity within the lumbar spine since the onset of volitional control and the decay of volitional control of bladder function both required weeks to appear and disappear. The decrement in micturition function (FIG. 17) indicate that a rehabilitation regimen that is conducted in a physical therapy/rehabilitation center once every two weeks may be sufficient to maintain voluntary micturition.

It is also interesting that we saw a variation of responses among our five subjects. While we do not have a precise explanation, we do know that the variation was not a result of differences among the ASIA grade (Subject A, B, E were ASIA A, but subject A improved much more than the other two). We believe the reasons for the variation are multifactorial. First and perhaps most importantly, our subjects (and all SCI individuals) have variable amounts of residual spinal function. The current ASIA classification system is not sophisticated enough to address the subtleties of residual spinal functions among subjects. At this time, no classification system or imaging modality allows one to assess the exact extent and severity of each individual's SCI and residual spinal circuitry. The other major source of variation among the subjects results from differences among each individual's effort and motivation during urination and bladder rehabilitation.

Regardless of the precise mechanism, our results, while still early, are highly encouraging. We were able to enable paraplegic individuals with injuries classified as ASIA A, who had been unable to urinate for as long as 28 years, to void voluntarily after 4 weeks of completely non-invasive transcutaneous magnetic stimulation. We were also able to decrease the frequency of bladder spasms, increase the bladder storage capacity to normal levels and significantly decrease the number of self-catheterizations. There were, in addition, unexpected ancillary benefits.

Bowel function improved and erections were more frequent. Both findings imply that other lumbar circuits were also altered and placed in a state of heightened accessibility to volitional control. Moreover, the combination of improved urinary function, improved bladder function and improved sexual function led to significantly improved quality of life ratings by the subjects (FIG. 18). Thus, transcutaneous magnetic stimulation might be used to improve the quality of life and independence in such patients, while simultaneously reducing the potential for urinary tract infections associated with repeated self-catheterization.

The main limitations of our study are its small size and the lack of proof of the actual mechanism of action. As this is a pilot study, we plan to continue to expand the study and enroll additional subjects. Further studies will focus on the molecular and cellular processes that follow magnetic stimulation to investigate the precise mechanism of action of magnetic stimulation.

Conclusions.

Urinary dysfunction is consistently the top negative factor in SCI patients' quality of life. Management of urinary dysfunction in SCI patients remains a difficult task despite many technological advancements. Most of the current treatment options are invasive and not very effective. We used a non-invasive, transcutaneous magnetic stimulator in the thoraco-lumbar region to deliver weekly low frequency magnetic stimulation in five subjects with chronic SCI to modulate and restore bladder function. Each subject was able to achieve some level of volitional urination: one subject was able to completely eliminate catheterization and one other subject only needing one catheterization per day during the period of study. While the exact mechanism of action remains unknown, it is clear that transcutaneous magnetic spinal cord stimulation modulated the complex behavior required to empty the bladder rather than just activating multiple peripheral nerves. Because the benefit that we observed was the result of cumulative stimulation and was delayed until at least four weeks of lumbar stimulation had been given, improved bladder function seemed to be derived from enhanced communication of volitional control to the lumbar spine, which coordinated bladder activity (increased stimulation of detrusor muscle and inhibition of the urethral muscle and external sphincter). These findings seem best explained by a permissive effect of transcutaneous magnetic stimulation that enhances activation of the spinal cord micturition circuitry. Future studies with more subjects will be needed to validate the effectiveness of transcutaneous magnetic spinal cord stimulation in restoring bladder function in chronic SCI patients.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of facilitating voiding or control of bladder and/or bowel in a subject with a neuromotor disorder, said method comprising:
providing a plurality of treatments comprising magnetic stimulation of the thoracic and/or lumbosacral spinal cord at a location, a frequency and an intensity sufficient to alter the activity of spinal circuitry, rather than peripheral nerve or muscle stimulation, wherein the altered activity of spinal circuitry provides volitional voiding or control of bladder and/or bowel, wherein said plurality of treatments are provided at a treatment frequency of at least one treatment or more per week;
reducing the treatment frequency of said treatments after said subject retains volitional voiding or control between treatments in the plurality of treatments even when magnetic stimulation is not present; and
wherein said frequency ranges from 0.5 Hz up to 100 Hz, said magnetic stimulation is applied over one or more regions selected from the group consisting of T11-T12, L1-L2, and L2-L3; and treatment gains in the volitional voiding or control of bladder and/or bowel from the magnetic stimulation are hardwired and present even without magnetic stimulation.

2. The method of claim 1, wherein said magnetic stimulation comprises stimulation at a frequency ranging from 0.5 Hz up to 20 Hz to induce micturition.

3. The method of claim 1, wherein said magnetic stimulation comprises stimulation at a frequency from 20 Hz up to 100 Hz to suppress micturition.

4. The method of claim 1, wherein said magnetic stimulation comprises magnetic pulses ranging in duration from 5 µs up to 500 µs.

5. The method of claim 1, wherein a single treatment of said magnetic stimulation comprises 1, or 2, or 3, or 4, or 5, or 6, or 7, or 8, or 9, or 10 or more periods of continuous magnetic stimulation and where there are two or more periods of continuous magnetic stimulation, the periods are separated by delay times in which there is no magnetic stimulation.

6. The method of claim 5, wherein each of said period(s) of continuous stimulation independently ranges in duration from 10 seconds up to 10 minutes.

7. The method of claim 5, wherein a single treatment comprises two or more periods of continuous magnetic stimulation separated by a delay period(s) where said delay periods independently range in duration from 5 seconds up to 5 minutes.

8. The method of claim 7, wherein said treatment frequency is daily or weekly over a period of time of at least 4 weeks.

9. The method of claim 8, wherein said treatment frequency is weekly.

10. The method of claim 9, where said treatment comprises at least three stimulation periods with a break of 30 seconds between each stimulation period.

11. The method of claim 9, where said subject obtains voluntary control of bladder and/or bowel after 16 weeks of weekly treatment.

12. The method of claim 7, wherein said treatment frequency is daily, or every 2 days, or every 3 days, or every 4 days, or every 5 days, or every 6 days, or weekly until the subject obtains volitional control of micturition.

13. The method of claim 12, wherein said treatment frequency is daily, or every 2 days, or every 3 days, or every 4 days, or every 5 days, or every 6 days, or weekly until the subject obtains their maximal volitional control of micturition.

14. The method of claim 13, wherein the treatment frequency is reduced after the subject obtains maximal volitional control of micturition.

15. The method of claim 14, wherein the treatment frequency is reduced to a level sufficient to maintain volitional control of micturition.

16. The method of claim 15, wherein the treatment frequency is reduced to every three days, or to a weekly treatment, or to every 10 days, or to every 2 weeks.

17. The method of claim 1, wherein said magnetic stimulation is applied over one or more regions selected from the group consisting of T1-T1, T1-T2, T1-T3, T1-T4, T1-T5, T1-T6, T1-T7, T1-T8, T1-T9, T1-T10, T1-T11, T1-T12, T2-T2, T2-T3, T2-T4, T2-T5, T2-T6, T2-T7, T2-T8, T2-T9, T2-T10, T2-T11, T2-T12, T3-T3, T3-T4, T3-T5, T3-T6, T3-T7, T3-T8, T3-T9, T3-T10, T3-T11, T3-T12, T4-T4, T4-T5, T4-T6, T4-T7, T4-T8, T4-T9, T4-T10, T4-T11, T4-T12, T5-T5, T5-T6, T5-T7, T5-T8, T5-T9, T5-T10, T5-T11, T5-T12, T6-T6, T6-T7, T6-T8, T6-T9, T6-T10, T6-T11, T6-T12, T7-T7, T7-T8, T7-T9, T7-T10, T7-T11, T7-T12, T8-T8, T8-T9, T8-T10, T8-T11, T8-T12, T9-T9, T9-T10, T9-T11, T9-T12, T10-T10, T10-T11, T10-T12, T11-T11, T11-T12, T12-T12, L1-L1, L1-L2, L1-L3, L1-L4, L1-L5, L1-S1, L1-S2, L1-S3, L1-S4, L1-S5, L2-L2, L2-L3, L2-L4, L2-L5, L2-S1, L2-S2, L2-S3, L2-S4, L2-S5, L3-L3, L3-L4, L3-L5, L3-S1, L3-S2, L3-S3, L3-S4, L3-S5, L4-L4, L4-L5, L4-S1, L4-S2, L4-S3, L4-S4, L4-S5, L5-L5, L5-S1, L5-S2, L5-S3, L5-S4, L5-S5, S1-S1, S1-S2, S1-S3, S1-S4, S1-S5, S2-S2, S2-S3, S2-S4, S2-S5, S3-S3, S3-S4, S3-S5, S4-S4, S4-S5, and S5-S6.

18. The method of claim 1, wherein said magnetic stimulation is applied over a region between T11 and L4.

19. The method of claim 18, wherein said magnetic stimulation is applied over L1 L2 and/or over T11-T12.

20. The method of claim 1, wherein said magnetic stimulation produces a magnetic field of at least 1 tesla, or at least 2 tesla, or at least 3 tesla, or at least 4 tesla, or at least 5 tesla.

21. The method of claim 1, wherein said subject is administered at least one monoaminergic agonist.

22. The method of claim 1, wherein:
said subject has a spinal cord injury; or
said subject has an ischemic brain injury; or
said subject has a neurodegenerative pathology.

23. The method of claim 1, wherein said volitional voiding or control of bladder and/or bowel improves over a period ranging from 4 to 16 weeks after initiating said treatments.

24. The method of claim 23, wherein said treatment frequency is weekly for at least 16 weeks.

25. The method of claim 1, wherein said subject has sustained voluntary bladder contraction with increased detrusor pressure during micturition, in the absence of magnetic stimulation.

26. The method of claim 1, wherein said subject has reduced urethral pressure that stays below bladder pressure during entire course of micturition without magnetic stimulation.

27. The method of claim 1, wherein said subject retains volitional bladder control for at least 2 weeks without magnetic stimulation.

* * * * *